(12) United States Patent
Nakagawa et al.

(10) Patent No.: US 12,105,013 B2
(45) Date of Patent: Oct. 1, 2024

(54) CURABLE RESIN COMPOSITION, METHOD FOR PRODUCING CURABLE RESIN COMPOSITION, AND METHOD FOR MEASURING SURFACE TACKINESS OF VISCOELASTIC MATERIAL

(71) Applicant: NICHIA CORPORATION, Anan (JP)

(72) Inventors: Yasunobu Nakagawa, Himeji (JP); Takeshi Yoshida, Ohtake (JP); Satoru Ogawa, Anan (JP); Masafumi Kuramoto, Anan (JP); Masahide Bando, Anan (JP)

(73) Assignee: NICHIA CORPORATION, Anan (JP)

( * ) Notice: Subject to any disclaimer, the term of this patent is extended or adjusted under 35 U.S.C. 154(b) by 871 days.

(21) Appl. No.: 16/598,641

(22) Filed: Oct. 10, 2019

(65) Prior Publication Data
US 2020/0049618 A1 Feb. 13, 2020

Related U.S. Application Data

(62) Division of application No. 15/630,559, filed on Jun. 22, 2017, now Pat. No. 10,488,325.

(30) Foreign Application Priority Data

Jun. 23, 2016 (JP) ................................ 2016-124804

(51) Int. Cl.
*C08L 83/04* (2006.01)
*C09J 183/04* (2006.01)
*C09J 183/06* (2006.01)
*G01N 19/04* (2006.01)
*G01N 33/44* (2006.01)
*H01L 33/56* (2010.01)
*C08G 77/20* (2006.01)
*C08G 77/50* (2006.01)

(52) U.S. Cl.
CPC .............. *G01N 19/04* (2013.01); *C08L 83/04* (2013.01); *C09J 183/04* (2013.01); *C09J 183/06* (2013.01); *G01N 33/442* (2013.01); *G01N 33/445* (2013.01); *H01L 33/56* (2013.01); *C08G 77/20* (2013.01); *C08G 77/50* (2013.01)

(58) Field of Classification Search
CPC ....................................................... C08L 83/04
See application file for complete search history.

(56) References Cited

U.S. PATENT DOCUMENTS

| | | | |
|---|---|---|---|
| 5,438,863 A | 8/1995 | Johnson | |
| 9,056,985 B2* | 6/2015 | Ko | ........................... C08L 83/04 |
| 10,556,993 B2* | 2/2020 | Mizunashi | ............ H01L 23/296 |
| 2012/0172544 A1 | 7/2012 | Liang et al. | |
| 2012/0184663 A1* | 7/2012 | Hamamoto | ............. C08L 83/04 |
| | | | 525/478 |
| 2014/0031734 A1 | 1/2014 | Saxena et al. | |
| 2015/0126700 A1 | 5/2015 | Kamuro et al. | |
| 2015/0340299 A1* | 11/2015 | Nakagawa | ............. C08G 77/50 |
| | | | 524/588 |

FOREIGN PATENT DOCUMENTS

| | | |
|---|---|---|
| JP | 8-75633 A | 3/1996 |
| JP | 2006-258804 A | 9/2006 |
| JP | 2012-140617 A | 7/2012 |
| WO | WO2013/176238 A1 | 11/2013 |
| WO | WO2014/109349 A1 | 7/2014 |

OTHER PUBLICATIONS

Brochure for "MTT 175—Miniature Tensile Tester", Drop Scientific Sdn. Bhd., 2015.

* cited by examiner

*Primary Examiner* — Margaret G Moore
(74) *Attorney, Agent, or Firm* — Birch, Stewart, Kolasch & Birch, LLP

(57) ABSTRACT

Provided is a curable resin composition which can be cured to form a material (cured product) that has low tack properties and resists adhesion of garbage. The present invention provides a curable resin composition comprising polysiloxane (A) having not less than 2 alkenyl groups in the molecule and polysiloxane (B) having not less than 2 hydrosilyl groups in the molecule, wherein $(T+Q)/D>0.3$ and $M+D+T+Q=1$ are satisfied regarding all silicon atoms contained therein, the amount of the hydrosilyl groups with respect to 1 mol of aliphatic carbon-carbon double bonds present therein is 0.9 to 5.0 mol, and a cured product of the curable resin composition exhibits a separation strength of not more than 0.40 N per $mm^2$ in separation load evaluation and/or a total separation load of not more than 0.018 N·mm per $mm^2$.

20 Claims, 2 Drawing Sheets

Figure 1
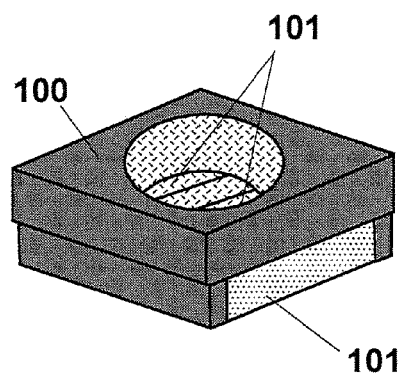
Figure 1(a)
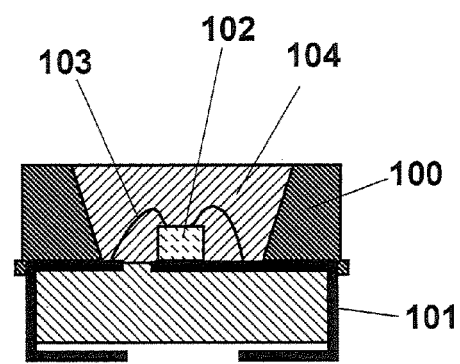
Figure 1(b)
Figure 2
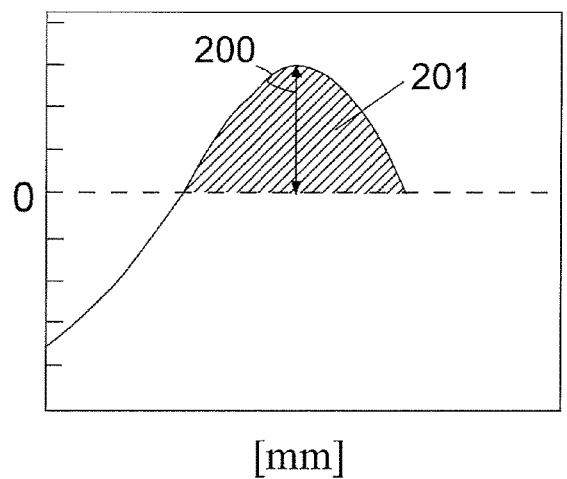
[mm]

CURABLE RESIN COMPOSITION, METHOD FOR PRODUCING CURABLE RESIN COMPOSITION, AND METHOD FOR MEASURING SURFACE TACKINESS OF VISCOELASTIC MATERIAL

CROSS-REFERENCE TO RELATED APPLICATIONS

This application is a Divisional of U.S. application Ser. No. 15/630,559, now U.S. Ser. No. 10/488,325 filed on Jun. 22, 2017, which claims priority under 35 U.S.C. 119(a) to Patent Application No. 2016-124804, filed in Japan on Jun. 23, 2016. All of the above applications are hereby incorporated by reference into the present application.

TECHNICAL FIELD

The present invention relates to a curable resin composition and a cured product thereof, a sealing agent comprising the curable resin composition, and a semiconductor apparatus (particularly, an optical semiconductor apparatus) obtained by sealing a semiconductor device (particularly, an optical semiconductor device) using the sealing agent. The present invention also relates to a method for producing a curable resin composition. The present invention further relates to a method for measuring the surface tackiness of a viscoelastic material. The present application claims the priority of Japanese Patent Application No. 2016-124804 filed in Japan on Jun. 23, 2016, the contents of which are incorporated herein by reference.

BACKGROUND ART

In semiconductor apparatuses, various resin materials are used as sealing members for covering and protecting semiconductor devices. Particularly, sealing members in optical semiconductor apparatuses are required to have excellent barrier properties against corrosive gas typified by sulfur compounds such as $SO_X$ and $H_2S$.

Methylsilicone (methylsilicone sealing members) excellent in heat resistance is mainly used as sealing members in optical semiconductor apparatuses, particularly, for the purpose of illumination. For example, use of a resin composition containing methylsilicone supplemented with ladder-type silsesquioxane, an isocyanurate compound, and a silane coupling agent as a sealing agent is known to improve sulfidation resistance against $SO_X$ (see e.g., Patent Literature 1).

CITATION LIST

Patent Literature

Patent Literature 1: International Publication No. WO 2014/109349

SUMMARY OF INVENTION

Technical Problem

Most of conventional silicone sealing members have tack properties. Therefore, during picking of LEDs containing such a silicone sealing member, a pickup tool adheres to a sealing member-exposed portion on the surface, or the LEDs stick to each other in a production line, resulting in undesired reduction in workability. The LEDs containing the silicone sealing member also present the problem that garbage easily adheres to the sealing member-exposed portion on the surface.

Thus, an object of the present invention is to provide a curable resin composition which can be cured to form a material (cured product) that has low tack properties and resists adhesion of garbage.

Another object of the present invention is to provide a material (cured product) which has low tack properties and resists adhesion of garbage.

A further alternative object of the present invention is to provide a sealing agent comprising the curable resin composition, and a semiconductor apparatus (particularly, an optical semiconductor apparatus) excellent in quality and durability which is obtained by sealing a semiconductor device (particularly, an optical semiconductor device) using the sealing agent.

A further alternative object of the present invention is to provide a method for producing a curable resin composition which can produce a curable resin composition for which the tack properties of a cured product of the curable resin composition and the adherence of garbage to the cured product can be estimated.

A conventional curable resin composition for forming silicone sealing members can be confirmed, for tack properties and the adherence of garbage thereto of LED obtained by sealing a LED device with a material prepared by curing the conventional curable resin composition, only by actually producing the LED. Heretofore, a cured product obtained by curing a curable resin composition under predetermined conditions has been able to be evaluated for its tack properties by a conventional method before actual production of LED.

As for the conventional evaluation of tack properties, for example, JIS Z 0237 stipulates a slope system ball tack test with JIS Z 0237 related supplements (rolling ball tack test and probe tack test). The J. Dow method may be used in the ball tack test. In the ball tack test, each steel ball is rolled on the sloped adhesive face of a test specimen, and the tack properties are evaluated on the basis of the rolling distance. The balance between the kinetic energy of the steel ball rolled on the slope and adhesive strength is rated as tack properties from running distance or steel ball size. In the probe tack test, tackiness is measured by pressing a needle-like object against a test specimen.

However, the conventional evaluation of tack properties as described above is not suitable for viscoelastic materials having low tack properties, such as silicone sealing members, though suitable for pressure-sensitive adhesives or the like having high tack properties. For example, the ball tack test does not exert desirable accuracy in terms of quantitative performance and reproducibility in adhesiveness evaluation for small tack properties. The probe tack test does not always accomplish adequate measurement, for example, due to uneven evaluation results, because a test specimen is deformed by an object or the contact area between the object and the test specimen is small. The probe tack test is directed to the evaluation of pressure-sensitive adhesives for tapes or the like and may therefore have insufficient detection capability or measurement stability in a low-tack region for quantifying the surface tackiness of viscoelastic bodies.

Thus, a further alternative object of the present invention is to provide a method for measuring the surface tackiness of a viscoelastic material which has high measurement accuracy in a low-tack region and is capable of quantitative measurement from a low-tack region to a high-tack region.

Solution to Problem

The present inventors have found that a curable resin composition which comprises a silicone resin having a particular composition comprising particular polysiloxane having not less than 2 alkenyl groups in the molecule and particular polysiloxane having not less than 2 hydrosilyl groups in the molecule as essential components and whose cured product exhibits not more than particular values of separation strength and a total separation load in particular separation load evaluation can be cured to form a cured product that has low tack properties and resists adhesion of garbage. The present inventors have also found that a measurement method comprising: contacting a viscoelastic material with an object so as to attain a particular contact area, applying a load to the viscoelastic material, and relaxing the stress; then separating the object and the viscoelastic material; and recording change in stress on the contact face from this contact to the separation and quantifying tackiness has high measurement accuracy in a low-tack region and is capable of quantitative measurement from a low-tack region to a high-tack region. The present invention has been completed on the basis of these findings.

Specifically, the present invention provides a curable resin composition comprising at least one polysiloxane (A) selected from the group consisting of polyorganosiloxane (A1) having not less than 2 alkenyl groups in the molecule and polyorganosiloxysilalkylene (A2) having not less than 2 alkenyl groups in the molecule, and at least one polysiloxane (B) selected from the group consisting of polyorganosiloxane (B1) having not less than 2 hydrosilyl groups in the molecule and polyorganosiloxysilalkylene (B2) having not less than 2 hydrosilyl groups in the molecule, wherein the curable resin composition comprises at least one polysiloxane selected from the group consisting of polyorganosiloxane represented by the following average unit formula (a-1) and polyorganosiloxysilalkylene represented by the following average unit formula (a-2) as the polysiloxane (A), and at least one polysiloxane selected from the group consisting of polyorganosiloxane represented by the following average unit formula (b-1) and polyorganosiloxysilalkylene represented by the following average unit formula (b-2) as the polysiloxane (B), when the ratio of the number of a silicon atom in a siloxane unit represented by $(R_3SiO_{1/2})$ to all silicon atoms contained in the curable resin composition is defined as M, the ratio of the number of a silicon atom in a siloxane unit represented by $(R_2SiO_{2/2})$ thereto is defined as D, the ratio of the number of a silicon atom in a siloxane unit represented by $(RSiO_{3/2})$ thereto is defined as T, and the ratio of the number of a silicon atom in a siloxane unit represented by $(SiO_{4/2})$ thereto is defined as Q, the curable resin composition satisfies $(T+Q)/D>0.3$ and $M+D+T+Q=1$ (wherein R represents a monovalent group), the amount of the hydrosilyl groups is 0.9 to 5.0 mol with respect to 1 mol of aliphatic carbon-carbon double bonds present in the curable resin composition, and a cured product obtained by curing the curable resin composition by heating under at least one curing condition selected from among conditions involving 25 to 180° C. and 1 to 720 minutes exhibits a separation strength of not more than 0.40 N per mm² in the following separation load evaluation and/or a total separation load of not more than 0.018 N·mm per mm² in the following separation load evaluation:

separation load evaluation: an object made of SUS and the cured product are contacted with each other by moving at least one of the object and the cured product from perpendicularly distant positions so as to attain a contact area of 50 to 800 mm² between the object and the cured product, pressed against each other at a load of 100 N for 2 minutes, and then separated in a perpendicular direction; change in stress on the contact face in this operation is recorded; a value determined by dividing a maximum stress value from when the object and the cured product start to be separated to when the object and the cured product are completely separated by the contact area is used as the separation strength; and a value determined by dividing an area surrounded by a stress curve from when the object and the cured product start to be separated to when the object and the cured product are completely separated and a baseline by the contact area is used as the total separation load, provided that the separation strength and the total separation load are each set to the largest value among values obtained by measurement with rates of the separation set to arbitrary 10 points (wherein adjacent 2 points differ in rate by not less than 5 mm/min) within the range of 5 to 500 mm/min,

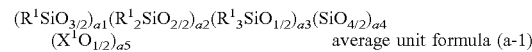
$$(R^1SiO_{3/2})_{a1}(R^1{}_2SiO_{2/2})_{a2}(R^1{}_3SiO_{1/2})_{a3}(SiO_{4/2})_{a4}$$
$$(X^1O_{1/2})_{a5} \quad \text{average unit formula (a-1)}$$

wherein $R^1$ moieties are the same or different and each represent an alkyl group having 1 to 10 carbon atoms, an aryl group having 6 to 14 carbon atoms, or an alkenyl group having 2 to 8 carbon atoms, provided that some of the $R^1$ moieties are alkenyl groups in the range of not less than 2 in the molecule; $X^1$ represents a hydrogen atom or an alkyl group having 1 to 6 carbon atoms; and a1, a2, a3, a4, and a5 represent numerical values satisfying $1>a1\geq0$, $1>a2\geq0$, $1>a3>0$, $1>a4\geq0$, $0.05\geq a5\geq0$, $a1+a2+a4>0$, and $a1+a2+a3+a4+a5=1$,

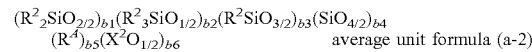
$$(R^2{}_2SiO_{2/2})_{b1}(R^2{}_3SiO_{1/2})_{b2}(R^2SiO_{3/2})_{b3}(SiO_{4/2})_{b4}$$
$$(R^4)_{b5}(X^2O_{1/2})_{b6} \quad \text{average unit formula (a-2)}$$

wherein $R^2$ moieties are the same or different and each represent an alkyl group having 1 to 10 carbon atoms, an aryl group having 6 to 14 carbon atoms, or an alkenyl group having 2 to 8 carbon atoms, provided that some of the $R^2$ moieties are alkenyl groups in the range of not less than 2 in the molecule; $R^4$ represents an alkylene group having 1 to 14 carbon atoms; $X^2$ represents a hydrogen atom or an alkyl group having 1 to 6 carbon atoms; and b1, b2, b3, b4, b5, and b6 represent numerical values satisfying $1>b1\geq0$, $1>b2>0$, $1>b3\geq0$, $1>b4\geq0$, $0.7>b5>0$, $0.05\geq b6\geq0$, $b1+b3+b4>0$, and $b1+b2+b3+b4+b5+b6=1$,

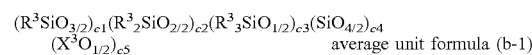
$$(R^3SiO_{3/2})_{c1}(R^3{}_2SiO_{2/2})_{c2}(R^3{}_3SiO_{1/2})_{c3}(SiO_{4/2})_{c4}$$
$$(X^3O_{1/2})_{c5} \quad \text{average unit formula (b-1)}$$

wherein $R^3$ moieties are the same or different and each represent a hydrogen atom, an alkyl group having 1 to 10 carbon atoms, or an aryl group having 6 to 14 carbon atoms, provided that some of the $R^3$ moieties are hydrogen atoms in the range of not less than 2 in the molecule; $X^3$ represents a hydrogen atom or an alkyl group having 1 to 6 carbon atoms; and c1, c2, c3, c4, and c5 represent numerical values satisfying $1>c1\geq0$, $1>c2\geq0$, $1>c3>0$, $1>c4\geq0$, $0.05\geq c5\geq0$, $c1+c2+c4>0$, and $c1+c2+c3+c4+c5=1$, and

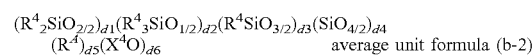
$$(R^4{}_2SiO_{2/2})_{d1}(R^4{}_3SiO_{1/2})_{d2}(R^4SiO_{3/2})_{d3}(SiO_{4/2})_{d4}$$
$$(R^4)_{d5}(X^4O)_{d6} \quad \text{average unit formula (b-2)}$$

wherein $R^4$ moieties are the same or different and each represent a hydrogen atom, an alkyl group having 1 to 10 carbon atoms, or an aryl group having 6 to 14 carbon atoms, provided that some of the $R^4$ moieties are hydrogen atoms in the range of not less than 2 in the molecule; $R^{-4}$ represents an alkylene group having 1 to 14 carbon atoms; $X^4$ represents a hydrogen atom or an alkyl group having 1 to 6 carbon atoms; and d1, d2, d3, d4, d5, and d6 represent numerical values satisfying 1>d1≥0, 1>d2>0, 1>d3≥0, 1>d4≥0, 0.5>d5>0, 0.05≥d6≥0, d1+d3+d4>0, and d1+d2+d3+d4+d5+d6=1.

Preferably, the curable resin composition further satisfies 0.9>T≥0.4 or 0.9>Q≥0.2.

Preferably, the curable resin composition further comprises ladder-type polyorganosilsesquioxane (C).

Preferably, the curable resin composition comprises, as the ladder-type polyorganosilsesquioxane (C), ladder-type silsesquioxane (C1) having a polyorganosilsesquioxane residue comprising a unit structure represented by the following formula (V):

[Formula 1]

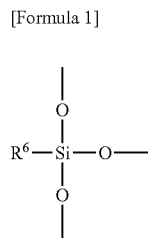

(V)

wherein $R^6$ represents a group having an aliphatic carbon-carbon double bond, and a unit structure represented by the following formula (VI):

[Formula 2]

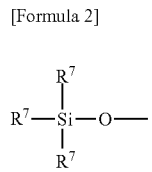

(VI)

wherein $R^7$ moieties are the same or different and each represent a hydrocarbon group at a portion or the whole of the molecular chain ends of the polyorganosilsesquioxane having a ladder structure.

Preferably, the curable resin composition comprises, as the ladder-type polyorganosilsesquioxane (C), ladder-type silsesquioxane (C2) having a polyorganosilsesquioxane residue comprising a unit structure represented by the following formula (VII):

[Formula 3]

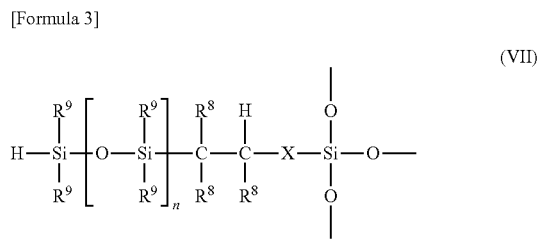

(VII)

wherein X represents a single bond, a divalent hydrocarbon group, a carbonyl group, an ether group, a thioether group, an ester group, a carbonate group, an amide group, or a group having a linkage of two or more of these groups; $R^8$ and $R^9$ moieties are the same or different and each represent a hydrogen atom, a halogen atom, a substituted or unsubstituted hydrocarbon group, an alkoxy group, an alkenyloxy group, an aryloxy group, an aralkyloxy group, an acyloxy group, an alkylthio group, an alkenylthio group, an arylthio group, an aralkylthio group, a carboxy group, an alkoxycarbonyl group, an aryloxycarbonyl group, an aralkyloxycarbonyl group, an epoxy group, a cyano group, an isocyanate group, a carbamoyl group, an isothiocyanate group, a hydroxy group, a hydroperoxy group, a sulfo group, an amino group or a substituted amino group, a mercapto group, a sulfo group, or a group represented by the following formula (s):

[Formula 4]

(s)

wherein $R^{51}$ moieties are the same or different and each represent a hydrogen atom, a halogen atom, a substituted or unsubstituted hydrocarbon group, an alkoxy group, an alkenyloxy group, an aryloxy group, an aralkyloxy group, an acyloxy group, an alkylthio group, an alkenylthio group, an arylthio group, an aralkylthio group, a carboxy group, an alkoxycarbonyl group, an aryloxycarbonyl group, an aralkyloxycarbonyl group, an epoxy group, a cyano group, an isocyanate group, a carbamoyl group, an isothiocyanate group, a hydroxy group, a hydroperoxy group, a sulfo group, an amino group or a substituted amino group, a mercapto group, or a sulfo group; and n represents an integer of 1 to 100, and a unit structure represented by the following formula (VIII):

[Formula 5]

(VIII)

wherein $R^{10}$ moieties are the same or different and each represent a hydrocarbon group at a portion or the whole of the molecular chain ends of the polyorganosilsesquioxane having a ladder structure.

Preferably, the ladder-type polyorganosilsesquioxane (C) is ladder-type polyorganosilsesquioxane having a substituted or unsubstituted aryl group at a portion or the whole of side chains.

Preferably, the ratio of an aryl group to the total amount of monovalent substituted or unsubstituted hydrocarbon groups bonded to silicon atom in all polysiloxanes contained in the curable resin composition is not less than 10% by mol.

Preferably, the curable resin composition further comprises an isocyanuric skeleton-containing compound (D).

Preferably, the isocyanuric skeleton-containing compound (D) is a compound represented by the following formula (1):

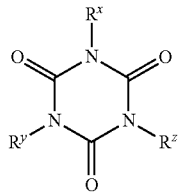

[Formula 6]

(1)

wherein $R^x$, $R^y$, and $R^z$ are the same or different and each represent a group represented by the formula (1a) or a group represented by the formula (1b):

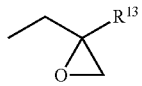

[Formula 7]

(1a)

wherein $R^{13}$ represents a hydrogen atom or a linear or branched alkyl group having 1 to 8 carbon atoms, and

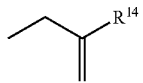

[Formula 8]

(1b)

wherein $R^{14}$ represents a hydrogen atom or a linear or branched alkyl group having 1 to 8 carbon atoms.

For the compound represented by the formula (1), preferably, not less than any one of $R^x$, $R^y$, and $R^z$ in the formula (1) is a group represented by the formula (1b).

Preferably, the curable resin composition further comprises a silane coupling agent (E).

The present invention also provides a cured product of the curable resin composition.

The present invention also provides a sealing agent comprising the curable resin composition.

The present invention also provides a semiconductor apparatus having a semiconductor device and a sealing member which seals the semiconductor device, wherein the sealing members is a cured product of the sealing agent.

The present invention further provides a method for producing a curable resin composition, comprising the step of determining the composition of the curable resin composition of interest by forming a cured product of a composition (I) and determining separation strength and/or a total separation load of the cured product by the following separation load evaluation, the composition (I) comprising at least one polysiloxane (A) selected from the group consisting of polyorganosiloxane (A1) having not less than 2 alkenyl groups in the molecule and polyorganosiloxysilalkylene (A2) having not less than 2 alkenyl groups in the molecule, and at least one polysiloxane (B) selected from the group consisting of polyorganosiloxane (B1) having not less than 2 hydrosilyl groups in the molecule and polyorganosiloxysilalkylene (B2) having not less than 2 hydrosilyl groups in the molecule, wherein the composition (I) comprises
at least one polysiloxane selected from the group consisting of polyorganosiloxane represented by the following average unit formula (a-1) and polyorganosiloxysilalkylene represented by the following average unit formula (a-2) as the polysiloxane (A), and
at least one polysiloxane selected from the group consisting of polyorganosiloxane represented by the following average unit formula (b-1) and polyorganosiloxysilalkylene represented by the following average unit formula (b-2) as the polysiloxane (B),
when the ratio of the number of a silicon atom in a siloxane unit represented by ($R_3SiO_{1/2}$) to all silicon atoms contained in the composition (I) is defined as M, the ratio of the number of a silicon atom in a siloxane unit represented by ($R_2SiO_{2/2}$) thereto is defined as D, the ratio of the number of a silicon atom in a siloxane unit represented by ($RSiO_{3/2}$) thereto is defined as T, and the ratio of the number of a silicon atom in a siloxane unit represented by ($SiO_{4/2}$) thereto is defined as Q, the composition (I) satisfies (T+Q)/D>0.3 and M+D+T+Q=1 (wherein R represents a monovalent group), and the amount of the hydrosilyl groups is 0.9 to 5.0 mol with respect to 1 mol of aliphatic carbon-carbon double bonds present in the composition (I):

separation load evaluation: an object and the cured product are contacted with each other by moving at least one of the object and the cured product from perpendicularly distant positions so as to attain a contact area of not less than 50 mm², pressed against each other under a load, and then separated in a perpendicular direction; change in stress on the contact face in this operation is recorded; a value determined by dividing a maximum stress value from when the object and the cured product start to be separated to when the object and the cured product are completely separated by the contact area between the object and the cured product is used as the separation strength; and a value determined by dividing an area surrounded by a stress curve from when the object and the cured product start to be separated to when the object and the cured product are completely separated and a baseline by the contact area is used as the total separation load,

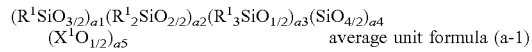

$(R^1SiO_{3/2})_{a1}(R^1{}_2SiO_{2/2})_{a2}(R^1{}_3SiO_{1/2})_{a3}(SiO_{4/2})_{a4}$
$(X^1O_{1/2})_{a5}$      average unit formula (a-1)

wherein $R^1$ moieties are the same or different and each represent an alkyl group having 1 to 10 carbon atoms, an aryl group having 6 to 14 carbon atoms, or an alkenyl group having 2 to 8 carbon atoms, provided that some of the $R^1$ moieties are alkenyl groups in the range of not less than 2 in the molecule; $X^1$ represents a hydrogen atom or an alkyl group having 1 to 6 carbon atoms; and a1, a2, a3, a4, and a5 represent numerical values satisfying 1>a1≥0, 1>a2≥0, 1>a3>0, 1>a4≥0, 0.05≥a5≥0, a1+a2+a4>0, and a1+a2+a3+a4+a5=1,

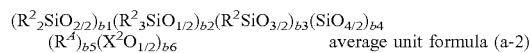

$(R^2{}_2SiO_{2/2})_{b1}(R^2{}_3SiO_{1/2})_{b2}(R^2SiO_{3/2})_{b3}(SiO_{4/2})_{b4}$
$(R^A)_{b5}(X^2O_{1/2})_{b6}$      average unit formula (a-2)

wherein $R^2$ moieties are the same or different and each represent an alkyl group having 1 to 10 carbon atoms, an aryl group having 6 to 14 carbon atoms, or an alkenyl group having 2 to 8 carbon atoms, provided that some of the $R^2$ moieties are alkenyl groups in the range of not less than 2 in the molecule; $R^4$ represents an alkylene group having 1 to 14 carbon atoms; $X^2$ represents a hydrogen atom or an alkyl group having 1 to 6 carbon atoms; and b1, b2, b3, b4, b5, and b6 represent numerical values satisfying $1>b1\geq0$, $1>b2>0$, $1>b3\geq0$, $1>b4\geq0$, $0.7>b5>0$, $0.05\geq b6\geq0$, $b1+b3+b4>0$, and $b1+b2+b3+b4+b5+b6=1$,

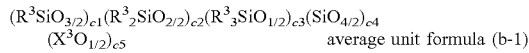
average unit formula (b-1)

wherein $R^3$ moieties are the same or different and each represent a hydrogen atom, an alkyl group having 1 to 10 carbon atoms, or an aryl group having 6 to 14 carbon atoms, provided that some of the $R^3$ moieties are hydrogen atoms in the range of not less than 2 in the molecule; $X^3$ represents a hydrogen atom or an alkyl group having 1 to 6 carbon atoms; and c1, c2, c3, c4, and c5 represent numerical values satisfying $1>c1\geq0$, $1>c2\geq0$, $1>c3>0$, $1>c4\geq0$, $0.05\geq c5\geq0$, $c1+c2+c4>0$, and $c1+c2+c3+c4+c5=1$, and

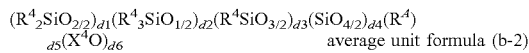
average unit formula (b-2)

wherein $R^4$ moieties are the same or different and each represent a hydrogen atom, an alkyl group having 1 to 10 carbon atoms, or an aryl group having 6 to 14 carbon atoms, provided that some of the $R^4$ moieties are hydrogen atoms in the range of not less than 2 in the molecule; $R^A$ represents an alkylene group having 1 to 14 carbon atoms; $X^4$ represents a hydrogen atom or an alkyl group having 1 to 6 carbon atoms; and d1, d2, d3, d4, d5, and d6 represent numerical values satisfying $1>d1\geq0$, $1>d2>0$, $1>d3\geq0$, $1>d4\geq0$, $0.5>d5>0$, $0.05\geq d6\geq0$, $d1+d3+d4>0$, and $d1+d2+d3+d4+d5+d6=1$.

The present invention further provides a method for measuring the surface tackiness of a viscoelastic material, comprising: step A of contacting an object and the viscoelastic material with each other so as to attain a contact area of not less than 50 mm², applying a load thereto, and subsequently relaxing the stress; step B of separating the object and the viscoelastic material by the application of displacement in the direction of separation; and step C of recording change in stress on the contact face from the contact to the separation, obtaining a curve of displacement on the x-axis and stress on the y-axis, and quantifying tackiness from the obtained curve.

Preferably, the step A involves using a stress detection mechanism having a mount and the object, placing a flat-shaped viscoelastic material onto the mount, continuously applying a load by pressing the object against the viscoelastic material such that the contact face between the viscoelastic material and the object is a plane, and subsequently relaxing the stress.

In the step C, a maximum stress value in the curve can be obtained as the tackiness value of the viscoelastic material. In the step C, an area that is surrounded by the curve and a baseline and is on a side including the maximum stress value in the curve can also be obtained as the tackiness value of the viscoelastic material.

Preferably, in the step A, a value determined by dividing the load applied after the contact of the object and the viscoelastic material by the contact area is 0.1 to 4 MPa.

Preferably, in the step A, the time for which the load is applied after the contact of the object and the viscoelastic material is 0.5 to 10 minutes.

Preferably, in the step B, the rate at which the object and the viscoelastic material are separated is set to 10 points of 5 mm/min, 10 mm/min, 20 mm/min, 30 mm/min, 50 mm/min, 70 mm/min, 100 mm/min, 150 mm/min, 300 mm/min, and 500 mm/min.

Preferably, the thickness of the viscoelastic material is 0.5 to 5 mm.

Preferably, the face of the object to be contacted with the viscoelastic material is a plane, and the plane area of the object is larger than the area of the contact portion between the viscoelastic material and the object.

Preferably, the method for measuring the surface tackiness of a viscoelastic material is carried out in an environment involving a temperature of 10 to 30° C. and a humidity of 30 to 70% RH.

Advantageous Effects of Invention

The curable resin composition of the present invention thus constituted can be cured to form a cured product that has low tack properties and resists adhesion of garbage. Therefore, in the case of using the cured product as a sealing member for a semiconductor device in a semiconductor apparatus, the semiconductor apparatus is improved in workability when handled, and further resists adhesion of garbage. Thus, the curable resin composition of the present invention can be preferably used as a material (sealing agent) for forming a sealing member for, particularly, an optical semiconductor device (LED device) in an optical semiconductor apparatus. The optical semiconductor apparatus obtained using the curable resin composition of the present invention as a sealing agent possesses excellent quality and durability.

The method for producing a curable resin composition according to the present invention can produce a curable resin composition for which the tack properties of a cured product of the obtained curable resin composition and the adherence of garbage to the cured product can be estimated. Therefore, a curable resin composition whose cured product has low tack properties and resists adhesion of garbage can be produced without actually producing a product using the cured product of the curable resin composition.

The method for measuring the tackiness of a viscoelastic material according to the present invention has high measurement accuracy even in a low-tack region and is capable of quantitative measurement from a low-tack region to a high-tack region. Therefore, the relative comparison of tack properties is easily conducted consistently as to various viscoelastic bodies from a low-tack region to a high-tack region, including viscoelastic materials having low tack properties.

BRIEF DESCRIPTION OF DRAWINGS

FIG. 1 is a schematic diagram showing one embodiment of optical semiconductor apparatus obtained by sealing an optical semiconductor device with a cured product of the curable resin composition of the present invention. FIG. 1(a) is a perspective view, and FIG. 1(b) is a cross-sectional view.

FIG. 2 is a graph showing one example of change in the amount of stress on the contact face between an object and a cured product in separation load evaluation.

DESCRIPTION OF EMBODIMENTS

<Curable Resin Composition>

Figure 3:
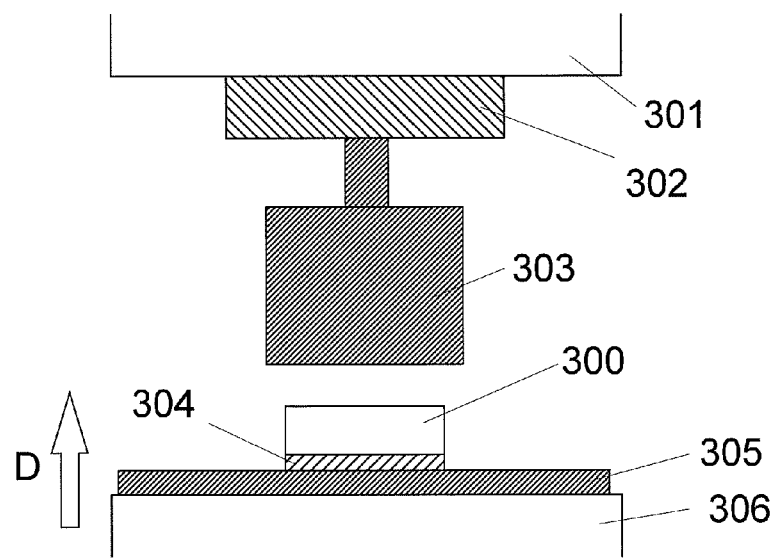
FIG. 3 is a schematic diagram showing the configuration of a tester used in separation load evaluation in Examples.

The curable resin composition of the present invention is a curable composition comprising at least one polysiloxane (A) selected from the group consisting of polyorganosiloxane (A1) having not less than 2 alkenyl groups in the molecule and polyorganosiloxysilalkylene (A2) having not less than 2 alkenyl groups in the molecule (also simply referred to as "polysiloxane (A)") and at least one polysiloxane (B) selected from the group consisting of polyorganosiloxane (B1) having not less than 2 hydrosilyl groups in the molecule and polyorganosiloxysilalkylene (B2) having not less than 2 hydrosilyl groups in the molecule (also simply referred to as "polysiloxane (B)") as essential components. The curable resin composition of the present invention may further comprise other components, for example, ladder-type polyorganosilsesquioxane (C), an isocyanuric skeleton-containing compound (D), and a hydrosilylation catalyst mentioned later, in addition to the essential components mentioned above.

The curable resin composition of the present invention comprises at least one polysiloxane selected from the group consisting of polyorganosiloxane represented by the average unit formula (a-1) given below and polyorganosiloxysilalkylene represented by the average unit formula (a-2) given below as the polysiloxane (A). Also, the curable resin composition of the present invention comprises at least one polysiloxane selected from the group consisting of polyorganosiloxane represented by the average unit formula (b-1) given below and polyorganosiloxysilalkylene represented by the average unit formula (b-2) given below as the polysiloxane (B). The polyorganosiloxane represented by the average unit formula (a-1) given below corresponds to the polyorganosiloxane (A1), and the polyorganosiloxysilalkylene represented by the average unit formula (a-2) given below corresponds to the polyorganosiloxysilalkylene (A2). Also, the polyorganosiloxane represented by the average unit formula (b-1) given below corresponds to the polyorganosiloxane (B1), and the polyorganosiloxysilalkylene represented by the average unit formula (b-2) given below corresponds to the polyorganosiloxysilalkylene (B2).

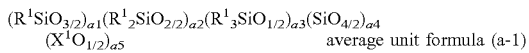
average unit formula (a-1)

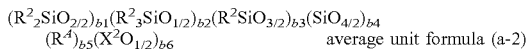
average unit formula (a-2)

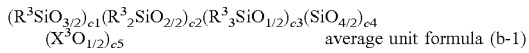
average unit formula (b-1)

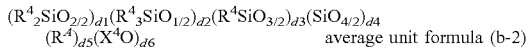
average unit formula (b-2)

When the ratio of the number of a silicon atom in a siloxane unit represented by $(R_3SiO_{1/2})$ to all silicon atoms contained in the curable resin composition of the present invention is defined as M, the ratio of the number of a silicon atom in a siloxane unit represented by $(R_2SiO_{2/2})$ thereto is defined as D, the ratio of the number of a silicon atom in a siloxane unit represented by $(RSiO_{3/2})$ thereto is defined as T, and the ratio of the number of a silicon atom in a siloxane unit represented by $(SiO_{4/2})$ thereto is defined as Q, M, D, T, and Q satisfy $(T+Q)/D>0.3$ and $M+D+T+Q=1$. The resulting cured product tends to have low tack properties and resist adhesion of garbage. Particularly preferably, $5>(T+Q)/D>0.3$ is satisfied. R described above represents a monovalent group. Examples thereof include a hydrogen atom, halogen atoms, monovalent organic groups, monovalent oxygen atom-containing groups, monovalent nitrogen atom-containing groups, and monovalent sulfur atom-containing groups. Examples of the monovalent organic groups include alkenyl groups and monovalent substituted or unsubstituted hydrocarbon groups mentioned later.

T or Q described above to all silicon atoms contained in the curable resin composition of the present invention further preferably satisfies $0.9>T\geq0.4$ or $0.9>Q\geq0.2$. The resulting cured product tends to resist adhesion of garbage and exhibit improved tenacity.

M, D, T, and Q described above to all silicon atoms contained in the curable resin composition of the present invention preferably satisfy $1>M\geq0$, $1>D>0$, $1>T>0$, and $1>Q>0$, respectively. M, D, T, and Q described above can be calculated by, for example, $^{29}$Si-NMR spectrum measurement. In the present specification, each of the ratios represented by M, D, T, and Q is a ratio to all silicon atoms contained in the curable resin composition of the present invention. Examples of the silicon atom-containing compounds contained in the curable resin composition of the present invention include the polysiloxane (A), the polysiloxane (B), and ladder-type polyorganosilsesquioxane (C) mentioned later.

The curable resin composition of the present invention has a composition (formulation) containing 0.9 to 5.0 mol, preferably 0.9 to 4.0 mol, more preferably 0.9 to 3.0 mol, further preferably 0.9 to 2.5 mol, of the hydrosilyl groups with respect to 1 mol of aliphatic carbon-carbon double bonds (particularly, alkenyl groups) present in the curable resin composition. When the ratio of the hydrosilyl groups to aliphatic carbon-carbon double bonds (particularly, alkenyl groups) is controlled within the range described above, uncured components (particularly, uncured polysiloxane (A) and uncured polysiloxane (B)) remain in lower amounts in a cured product, which thus tends to exhibit reduced separation strength. Furthermore, the cured product tends to exhibit improved heat resistance, transparency, thermal shock resistance, reflow resistance, and barrier properties against corrosive gas (e.g., SOx gas). The molar number of the hydrosilyl groups with respect to 1 mol of aliphatic carbon-carbon double bonds (particularly, alkenyl groups) can be calculated by, for example, $^1$H-NMR spectrum measurement.

When the curable resin composition of the present invention is cured by heating under at least one curing condition selected from among conditions involving 25 to 180° C. and 1 to 720 minutes, a cured product obtained by curing the curable resin composition of the present invention exhibits a separation strength of not more than 0.40 N per mm$^2$ in the separation load evaluation given below and/or a total separation load of not more than 0.018 N·mm per mm$^2$ in the separation load evaluation given below. Thus, the curable resin composition of the present invention may be a curable resin composition that satisfies only one of the separation strength of not more than 0.40 N per mm$^2$ in the separation load evaluation given below and the total separation load of not more than 0.018 N·mm per mm$^2$ in the separation load evaluation given below, or may be a curable resin composition that satisfies both of them. In the present specification, the following separation load evaluation is also referred to as "separation load evaluation (X)":

separation load evaluation: an object made of SUS and the cured product are contacted with each other by moving at least one of the object and the cured product from perpendicularly distant positions so as to attain a contact area of 50 to 800 mm$^2$ between the object and the cured product, pressed against each other at a load of 100 N for 2 minutes, and then separated in a perpendicular direction; change in stress on the contact face in this operation is recorded; a value determined by dividing a maximum stress value from when the object and the cured product start to be separated to when the object and the cured product are completely separated by the contact area is used as the separation strength; and a value determined by dividing an area surrounded by a stress curve from when the object and the cured product start to be separated to when the object and the cured product are completely separated and a baseline by the contact area is used as the total separation load, provided that the separation strength and the total separation load are each set to the largest value among values obtained by measurement with rates of the separation set to arbitrary 10 points (wherein adjacent 2 points differ in rate by not less than 5 mm/min) within the range of 5 to 500 mm/min.

The curable resin composition of the present invention satisfies the requirement that the cured product obtained by curing the curable resin composition under the particular condition has a separation strength of not more than 0.40 N per $mm^2$ in the separation load evaluation and/or a total separation load of not more than 0.018 N·mm per $mm^2$ in the separation load evaluation. The resulting curable resin composition of the present invention tends to reduce both of the tack properties of the cured product and the adherence of garbage thereto.

A conventional curable resin composition for forming silicone sealing members can be confirmed, for tack properties and the adherence of garbage thereto of LED obtained by sealing a LED device with a material prepared by curing the conventional curable resin composition, only by actually producing the LED. Heretofore, a cured product obtained by curing a curable resin composition under predetermined conditions has been able to be evaluated for its tack properties by a conventional method before actual production of LED. However, evaluation results obtained by the evaluation of tack properties using a tacking tester do not highly correlate with the tack properties of actually produced LED and the adherence of garbage thereto. Low tack properties do not always mean that the cured product resists adhesion of garbage. A cured product having low tack properties may be susceptible to adhesion of garbage, whereas a cured product having high tack properties may resist adhesion of garbage. As mentioned above, the tack properties of a material obtained by curing a conventional curable resin composition and the adherence of garbage thereto cannot be confirmed unless LED is actually produced using the material as a sealing member. In addition, every previous method for evaluating produced LED for its tack properties and the adherence of garbage thereto is qualitative.

By contrast, as for the curable resin composition having the particular composition, the tack properties of an optical semiconductor apparatus and the adherence of garbage thereto can be evaluated beforehand at a stage prior to actual production of the optical semiconductor apparatus using the curable resin composition as a sealing agent, by carrying out the separation load evaluation (X) and determining separation strength and/or a total separation load. Furthermore, the tack properties of produced LED and the adherence of garbage thereto can be quantitatively evaluated by the separation load evaluation (X). The curable resin composition of the present invention has the particular composition and allows the separation strength and/or the total separation load determined by the separation load evaluation (X) to fall within the particular range. The curable resin composition of the present invention can thereby be cured to form a cured product that has low tack properties and resists adhesion of garbage.

When the curable resin composition of the present invention is cured under the particular condition, the separation strength of the cured product obtained by curing the curable resin composition of the present invention is preferably not more than 0.40 N, more preferably not more than 0.10 N, per $mm^2$ in the separation load evaluation. The cured product having the separation strength of not more than 0.40 N tends to have reduced tack properties.

When the curable resin composition of the present invention is cured under the particular condition, the total separation load of the cured product obtained by curing the curable resin composition of the present invention is preferably not more than 0.018 N·mm, more preferably not more than 0.016 N·mm, further preferably not more than 0.010 N·mm, per $mm^2$ in the separation load evaluation. The cured product having the total separation load of not more than 0.018 N·mm tends to resist adhesion of garbage.

The polysiloxane (A) and the polysiloxane (B) contained in the curable resin composition are important for adjusting the separation strength and the total separation load to within their respective particular ranges described above. More specifically, the separation strength and the total separation load are easily adjusted to within their respective particular ranges described above by adjusting the proportion of linear polysiloxane and branched polysiloxane, the proportion of an alkyl group bonded to a silicon atom, the proportion of an aryl group bonded to a silicon atom, and the ratio of hydrosilyl groups to alkenyl groups in the polysiloxane (A) and the polysiloxane (B) in the curable resin composition. For example, use of linear polysiloxane tends to decrease separation strength, and use of branched polysiloxane tends to decrease a total separation load. As groups bonded to silicon atoms other than alkenyl groups and hydrosilyl groups in the polysiloxanes, a larger number of an alkyl group (particularly, a methyl group) tends to decrease separation strength, and a larger number of an aryl group (particularly, a phenyl group) tends to decrease a total separation load. Also, a larger amount of uncured components in a cured product tends to enhance separation strength. Therefore, the ratio of hydrosilyl groups to alkenyl groups is effectively adjusted so as to decrease the amount of uncured components in a cured product (particularly, so as to prevent the proportion of a vinyl group from being excessive).

(Separation Load Evaluation (X))

The separation load evaluation (X) is carried out on a cured product obtained by curing the curable resin composition of the present invention by heating under at least one curing condition selected from among conditions involving 25 to 180° C. and 1 to 720 minutes. Specifically, the separation load evaluation is conducted on a cured product obtained by curing the curable resin composition of the present invention by heating at an arbitrary temperature within the range of 25 to 180° C. for an arbitrary time within the range of 1 to 720 minutes. Accordingly, the range of the separation strength and/or the total separation load determined by the separation load evaluation of the cured product obtained by curing the curable resin composition of the present invention can be satisfied by a cured product obtained by curing under at least one of the curing conditions described above. The temperature of the curing (curing temperature) is preferably 60 to 170° C., more preferably 80 to 150° C. The heating time for the curing (curing time) is preferably 3 to 600 minutes, more preferably 60 to 480 minutes. The curing may be performed by one stage or may be performed by multiple stages. For the multiple stages of curing, the curing temperature at each stage is within the range of the curing temperature mentioned above, and the total curing time is within the range of the curing time mentioned above. Among others, heating at 100° C. for 1 hour and subsequent heating at 150° C. for 5 hours are preferred. The separation load evaluation (X) corresponds to the measurement method of the present invention mentioned later.

In the separation load evaluation, first, an object made of SUS and the cured product of the curable resin composition are contacted with each other by moving at least one of the object and the cured product from perpendicularly (or vertically) distant positions so as to attain a contact area of 50 to 800 mm$^2$ between the object and the cured product. The contact face between the object and the cured product is preferably a plane from the viewpoint that the contact area is less likely to be changed even by pressing under a load.

The object and the cured product thus contacted are then pressed against each other in a perpendicular direction at a load of 100 N for 2 minutes. The load may be applied from the object side or may be applied from the cured product side. The load is preferably applied from the cured product side. The direction in which the load is applied may be downward or may be upward in a vertical direction.

After the application of the load, the object and the cured product are separated in a perpendicular direction. During this series of procedures, i.e., the contact, pressing, and separation of the object and the cured product, change in stress on the contact face is recorded. Then, a value determined by dividing a maximum stress value from when the object and the cured product start to be separated to when the object and the cured product are completely separated by the contact area between the object and the cured product is used as the separation strength, and a value determined by dividing an area surrounded by a stress curve from when the object and the cured product start to be separated to when the object and the cured product are completely separated and a baseline (line at which the stress on the contact face is 0) by the contact area between the object and the cured product is used as the total separation load. FIG. 2 is a graph showing one example of change in the amount of stress on the contact face between the object and the cured product in the separation load evaluation. In FIG. 2, reference numeral 200 denotes the maximum stress value, and reference numeral 201 denotes the area surrounded by a stress curve from when the object and the cured product start to be separated to when the object and the cured product are completely separated and a baseline. In this context, the separation strength and the total separation load are each set to the largest value among values obtained by measurement with rates of the separation set to arbitrary 10 points within the range of 5 to 500 mm/min, provided that adjacent 2 points differ in rate by not less than 5 mm/min. This is because the separation rate at which the separation strength and the total separation load are largest may differ depending on the composition of the curable resin composition. The arbitrary 10 points are particularly preferably 10 points of 5 mm/min, 10 mm/min, 20 mm/min, 30 mm/min, 50 mm/min, 70 mm/min, 100 mm/min, 150 mm/min, 300 mm/min, and 500 mm/min.

The separation load evaluation (X) can be conducted using a commercially available universal tester (e.g., "TENSILON universal material tester RTC-1310A", manufactured by A&D Co., Ltd.).

[Polysiloxane (A)]

The polysiloxane (A) which is an essential component of the curable resin composition of the present invention is polysiloxane having not less than 2 alkenyl groups in the molecule, as mentioned above. Specifically, the polysiloxane (A) is polysiloxane having alkenyl groups and is a component that causes hydrosilylation reaction with a component having hydrosilyl groups (e.g., polysiloxane (B) mentioned later). However, the polysiloxane (A) excludes polysiloxane that corresponds to ladder-type polyorganosilsesquioxane (C) mentioned later.

The polysiloxane (A) is at least one polysiloxane selected from the group consisting of polyorganosiloxane (A1) having not less than 2 alkenyl groups in the molecule (also simply referred to as "polyorganosiloxane (A1))" and polyorganosiloxysilalkylene (A2) having not less than 2 alkenyl groups in the molecule (also simply referred to as "polyorganosiloxysilalkylene (A2)").

In the present specification, the polyorganosiloxysilalkylene (A2) is polysiloxane containing —Si—O—Si— (siloxane bond) as well as —Si—$R^A$—Si— (silalkylene bond; $R^A$ represents an alkylene group) in the backbone. In the present specification, the polyorganosiloxane (A1) is polysiloxane free from the silalkylene bond in the backbone.

(Polyorganosiloxane (A1))

Examples of the polyorganosiloxane (A1) include polyorganosiloxane having a linear, partially branched linear, branched, or network molecular structure. One of these polyorganosiloxanes (A1) can be used alone, or not less than two thereof can be used in combination. Specifically, not less than two polyorganosiloxanes (A1) differing in molecular structure can be used in combination. For example, linear polyorganosiloxane (A1) and branched polyorganosiloxane (A1) can also be used in combination.

Examples of the intramolecular alkenyl groups of the polyorganosiloxane (A1) include substituted or unsubstituted alkenyl groups such as a vinyl group, an allyl group, a butenyl group, a pentenyl group, and a hexenyl group. Examples of the substituent include halogen atoms, a hydroxy group, and a carboxy group. Among them, a vinyl group is preferred. The polyorganosiloxane (A1) may have only one type of alkenyl group or may have not less than two types of alkenyl groups. The alkenyl groups of the polyorganosiloxane (A1) are not particularly limited and are preferably bonded to silicon atom.

Examples of a group, except for the alkenyl groups, carried by the polyorganosiloxane (A1) include, but are not particularly limited to, organic groups. Examples of the organic groups include monovalent substituted or unsubstituted hydrocarbon groups such as alkyl groups [e.g., a methyl group, an ethyl group, a propyl group, a butyl group, a pentyl group, and a hexyl group], cycloalkyl groups [e.g., a cyclopropyl group, a cyclobutyl group, a cyclopentyl group, a cyclohexyl group, and a cyclododecyl group], aryl groups [e.g., a phenyl group, a tolyl group, a xylyl group, and a naphthyl group], cycloalkyl-alkyl groups [e.g., a cyclohexylmethyl group and a methylcyclohexyl group], aralkyl groups [e.g., a benzyl group and a phenethyl group], and halogenated hydrocarbon groups in which not less than 1 hydrogen atom in the hydrocarbon group is replaced with a halogen atom [e.g., alkyl halide groups such as a chloromethyl group, a 3-chloropropyl group, and a 3,3,3-trifluoropropyl group]. In the present specification, the "group bonded to a silicon atom" usually refers to a group excluding the silicon atom.

The polyorganosiloxane (A1) may also have a hydroxy group or an alkoxy group as a group bonded to a silicon atom.

The polyorganosiloxane (A1) is not particularly limited by its nature and may be liquid or may be solid, for example, at 25° C.

The polyorganosiloxane (A1) is preferably polyorganosiloxane represented by the following

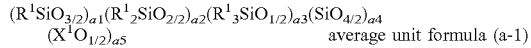
$$(R^1SiO_{3/2})_{a1}(R^1{}_2SiO_{2/2})_{a2}(R^1{}_3SiO_{1/2})_{a3}(SiO_{4/2})_{a4}(X^1O_{1/2})_{a5} \quad \text{average unit formula (a-1)}$$

In the average unit formula (a-1), 10 moieties are the same or different and each represent an alkyl group having 1 to 10 carbon atoms, an aryl group having 6 to 14 carbon atoms, or an alkenyl group having 2 to 8 carbon atoms, provided that some of the 10 moieties are alkenyl groups (particularly, a vinyl group), the proportion of which is controlled within the range of not less than 2 in the molecule. For example, the ratio of the alkenyl groups to the total amount (100% by mol) of the 10 moieties is preferably 0.1 to 40% by mol. When the ratio of the alkenyl groups is controlled within the range described above, the resulting curable resin composition tends to exhibit improved curing properties. The alkyl group having 1 to 10 carbon atoms is particularly preferably a methyl group, and the aryl group having 6 to 14 carbon atoms is particularly preferably a phenyl group.

In the average unit formula (a-1), $X^1$ is a hydrogen atom or an alkyl group having 1 to 6 carbon atoms. Examples of the alkyl group having 1 to 6 carbon atoms include a methyl group, an ethyl group, a propyl group, a butyl group, a pentyl group, and a hexyl group. A methyl group is particularly preferred.

In the average unit formula (a-1), a1, a2, a3, a4, and a5 are numerical values satisfying 1>a1≥0, 1>a2≥0, 1>a3>0, 1>a4≥0, 0.05≥a5≥0, a1+a2+a4>0, and a1+a2+a3+a4+a5=1.

One example of the polyorganosiloxane (A1) includes linear polyorganosiloxane having not less than 2 alkenyl groups in the molecule. Examples of the alkenyl groups of this linear polyorganosiloxane include the specific examples of the alkenyl groups mentioned above. Among them, a vinyl group is preferred. The linear polyorganosiloxane may have only one type of alkenyl group or may have not less than two types of alkenyl groups. Examples of a group bonded to a silicon atom, except for the alkenyl groups, in the linear polyorganosiloxane include the monovalent substituted or unsubstituted hydrocarbon groups mentioned above. Among them, an alkyl group (particularly, an alkyl group having 1 to 10 carbon atoms) or an aryl group (particularly, an aryl group having 6 to 14 carbon atoms) is preferred, and a methyl group or a phenyl group is particularly preferred.

The ratio of the alkenyl groups to the total amount (100% by mol) of groups bonded to silicon atoms in the linear polyorganosiloxane is not particularly limited and is preferably 0.1 to 40% by mol. The ratio of the alkyl group (particularly, a methyl group) to the total amount (100% by mol) of groups bonded to silicon atoms is not particularly limited and is preferably 1 to 20% by mol. The ratio of the aryl group (particularly, a phenyl group) to the total amount (100% by mol) of groups bonded to silicon atoms is not particularly limited and is preferably 30 to 90% by mol. Particularly, use of the linear polyorganosiloxane in which the ratio of the aryl group (particularly, a phenyl group) to the total amount (100% by mol) of groups bonded to silicon atoms is not less than 40% by mol (e.g., 45 to 80% by mol) tends to improve the barrier properties of a cured product against corrosive gas. Use of the linear polyorganosiloxane in which the ratio of the alkyl group (particularly, a methyl group) to the total amount (100% by mol) of groups bonded to silicon atoms is not less than 90% by mol (e.g., 95 to 99% by mol) tends to improve the thermal shock resistance of a cured product.

The linear polyorganosiloxane is represented by, for example, the following formula (1-1):

[Formula 9]

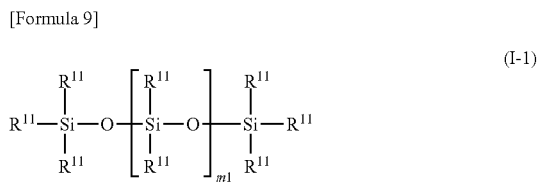

(I-1)

wherein $R^{11}$ moieties are the same or different and each represent a monovalent substituted or unsubstituted hydrocarbon group, provided that at least 2 of the $R^{11}$ moieties are alkenyl groups; and m1 is an integer of 5 to 1000.

Another example of the polyorganosiloxane (A1) includes branched polyorganosiloxane having not less than 2 alkenyl groups in the molecule and having a siloxane unit represented by $RSiO_{3/2}$ (T unit). However, the branched polyorganosiloxane excludes, as mentioned above, polyorganosiloxane that corresponds to ladder-type polyorganosilsesquioxane (C) mentioned later. R is a monovalent substituted or unsubstituted hydrocarbon group. Examples of the alkenyl groups of this branched polyorganosiloxane include the specific examples of the alkenyl groups mentioned above. Among them, a vinyl group is preferred. The branched polyorganosiloxane may have only one type of alkenyl group or may have not less than two types of alkenyl groups. Examples of a group bonded to a silicon atom, except for the alkenyl groups, in the branched polyorganosiloxane include the monovalent substituted or unsubstituted hydrocarbon groups mentioned above. Among them, an alkyl group (particularly, a methyl group) or an aryl group (particularly, a phenyl group) is preferred. Among others, R in the T unit is preferably an alkyl group (particularly, an alkyl group having 1 to 10 carbon atoms) or an aryl group (particularly, an aryl group having 6 to 14 carbon atoms), particularly preferably a methyl group or a phenyl group.

The ratio of the alkenyl groups to the total amount (100% by mol) of groups bonded to silicon atoms in the branched polyorganosiloxane is not particularly limited and is preferably 0.1 to 40% by mol from the viewpoint of the curing properties of the curable resin composition. The ratio of the alkyl group (particularly, a methyl group) to the total amount (100% by mol) of groups bonded to silicon atoms is not particularly limited and is preferably 10 to 40% by mol. The ratio of the aryl group (particularly, a phenyl group) to the total amount (100% by mol) of groups bonded to silicon atoms is not particularly limited and is preferably 5 to 70% by mol. Particularly, use of the branched polyorganosiloxane in which the ratio of the aryl group (particularly, a phenyl group) to the total amount (100% by mol) of groups bonded to silicon atoms is not less than 40% by mol (e.g., 45 to 60% by mol) tends to improve the barrier properties of a cured product against corrosive gas. Use of the branched polyorganosiloxane in which the ratio of the alkyl group (particularly, a methyl group) to the total amount (100% by mol) of groups bonded to silicon atoms is not less than 50% by mol (e.g., 60 to 99% by mol) tends to improve the thermal shock resistance of a cured product.

The branched polyorganosiloxane can be represented by the average unit formula (a-1) wherein a1 is a positive number. In this case, preferably, a2/a1 is a number of 0 to 10, a3/a1 is a number of 0 to 0.5, a4/(a1+a2+a3+a4) is a number of 0 to 0.3, and a5/(a1+a2+a3+a4) is a number of 0 to 0.4, though not particularly limited thereto. The molecular weight of the branched polyorganosiloxane is not particularly limited and is preferably 500 to 10000, more preferably 700 to 5000, in terms of weight-average molecular weight based on standard polystyrene.

A further alternative example of the polyorganosiloxane (A1) includes polyorganosiloxane represented by the average unit formula wherein each of a1 and a2 is 0, and $X^1$ is a hydrogen atom, i.e., the following average unit formula:

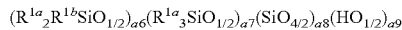

$(R^{1a}{}_2R^{1b}SiO_{1/2})_{a6}(R^{1a}{}_3SiO_{1/2})_{a7}(SiO_{4/2})_{a8}(HO_{1/2})_{a9}$

In the average unit formula, $R^{1a}$ moieties are the same or different and each represent an alkyl group having 1 to 10 carbon atoms ($C_{1-10}$ alkyl group). Examples thereof include a methyl group, an ethyl group, a propyl group, a butyl group, a pentyl group, a hexyl group, a cyclopentyl group, and a cyclohexyl group. Among them, a methyl group is preferred. $R^{1b}$ moieties are the same or different and each represent an alkenyl group. Among others, a vinyl group is preferred. All of a6, a7, a8, and a9 are positive numbers satisfying a6+a7+a8=1, a6/(a6+a7)=0.15 to 0.35, a8/(a6+a7+a8)=0.53 to 0.62, and a9/(a6+a7+a8)=0.005 to 0.03, provided that a7 may be 0. a6/(a6+a7) is preferably 0.2 to 0.3 from the viewpoint of the curing properties of the curable resin composition. a8/(a6+a7+a8) is preferably 0.55 to 0.60 from the viewpoint of the hardness and mechanical strength of a cured product. Examples of such polyorganosiloxane include polyorganosiloxane constituted by a $SiO_{4/2}$ unit and a $(CH_3)_2(CH_2{=}CH)SiO_{1/2}$ unit, and polyorganosiloxane constituted by a $SiO_{4/2}$ unit, a $(CH_3)_2(CH_2CH)SiO_{1/2}$ unit, and a $(CH_3)_3SiO_{1/2}$ unit.

(Polyorganosiloxysilalkylene (A2))

The polyorganosiloxysilalkylene (A2) is polysiloxane having not less than 2 alkenyl groups in the molecule and containing a siloxane bond as well as a silalkylene bond —Si—$R^A$—Si— ($R^A$ represents an alkylene group) in the backbone, as mentioned above. Specifically, the polyorganosiloxysilalkylene (A2) excludes polysiloxane having no silalkylene bond, such as the polyorganosiloxane (A1) mentioned above. The curable resin composition of the present invention comprising such polyorganosiloxysilalkylene (A2) can form a cured product excellent in barrier properties against corrosive gas and thermal shock resistance.

Examples of the alkylene group ($R^A$) in the intramolecular silalkylene bond of the polyorganosiloxysilalkylene (A2) include linear or branched C1-14 alkylene groups such as a methylene group, an ethylene group, and a propylene group. Among them, a $C_{2-4}$ alkylene group (particularly, an ethylene group) is preferred. Use of the polyorganosiloxysilalkylene (A2) tends to improve the sulfidation resistance of a cured product.

Examples of the polyorganosiloxysilalkylene (A2) include polyorganosiloxysilalkylene having a linear, partially branched linear, branched, or network molecular structure. One of these polyorganosiloxysilalkylenes (A2) can be used alone, or not less than two thereof can be used in combination. Specifically, not less than 2 polyorganosiloxysilalkylenes (A2) differing in molecular structure can be used in combination. For example, linear polyorganosiloxysilalkylene (A2) and branched polyorganosiloxysilalkylene (A2) can also be used in combination.

Examples of the intramolecular alkenyl groups of the polyorganosiloxysilalkylene (A2) include the substituted or unsubstituted alkenyl groups mentioned above. Among them, a vinyl group is preferred. The polyorganosiloxysilalkylene (A2) may have only one type of alkenyl group or may have not less than two types of alkenyl groups. The alkenyl groups of the polyorganosiloxysilalkylene (A2) are not particularly limited and are preferably bonded to silicon atoms.

Examples of a group bonded to a silicon atom, except for the alkenyl groups, carried by the polyorganosiloxysilalkylene (A2) include, but are not particularly limited to, organic groups. Examples of the organic groups include the organic groups mentioned above (e.g., substituted or unsubstituted hydrocarbon groups such as alkyl groups, cycloalkyl groups, aryl groups, cycloalkyl-alkyl groups, aralkyl groups, and halogenated hydrocarbon groups).

The polyorganosiloxysilalkylene (A2) may have a hydroxy group or an alkoxy group as a group bonded to a silicon atom.

The polyorganosiloxysilalkylene (A2) is not particularly limited by its nature and may be liquid or may be solid, for example, at 25° C.

The polyorganosiloxysilalkylene (A2) is preferably polyorganosiloxysilalkylene represented by the following average unit formula (a-2):

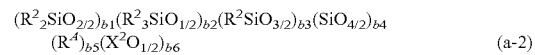

$(R^2{}_2SiO_{2/2})_{b1}(R^2{}_3SiO_{1/2})_{b2}(R^2SiO_{3/2})_{b3}(SiO_{4/2})_{b4}$
$(R^4)_{b5}(X^2O_{1/2})_{b6}$     (a-2)

In the average unit formula (a-2), $R^2$ moieties are the same or different and each represent an alkyl group having 1 to 10 carbon atoms, an aryl group having 6 to 14 carbon atoms, or an alkenyl group having 2 to 8 carbon atoms, provided that some of the $R^2$ moieties are alkenyl groups (particularly, a vinyl group), the proportion of which is controlled within the range of not less than 2 in the molecule. For example, the ratio of the alkenyl groups to the total amount (100% by mol) of the $R^2$ moieties is preferably 0.1 to 40% by mol. When the ratio of the alkenyl groups is controlled within the range described above, the resulting curable resin composition tends to exhibit improved curing properties.

In the average unit formula (a-2), $R^4$ is an alkylene group having 1 to 14 carbon atoms. Particularly, an ethylene group is preferred.

In the average unit formula (a-2), $X^2$ is a hydrogen atom or an alkyl group having 1 to 6 carbon atoms, as with $X^1$ described above. Examples of the alkyl group having 1 to 6 carbon atoms include a methyl group, an ethyl group, a propyl group, a butyl group, a pentyl group, and a hexyl group. Particularly, a methyl group is preferred.

In the average unit formula (a-2), b1, b2, b3, b4, b5, and b6 are numerical values satisfying 1>b1≥0, 1>b2>0, 1>b3≥0, 1>b4≥0, 0.7>b5>0, 0.05≥b6≥0, b1+b3+b4>0, and b1+b2+b3+b4+b5+b6=1. Particularly, the polyorganosiloxysilalkylene (A2) represented by the average unit formula (a-2) wherein b3+b4>0 has a branched chain (branched backbone) and tends to improve the mechanical strength of a cured product.

More specific examples of the polyorganosiloxysilalkylene (A2) include polyorganosiloxysilalkylene having a structure represented by the following formula (1-2):

[Formula 10]

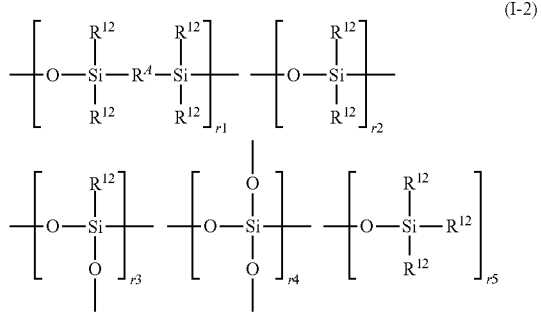

In the formula (1-2), $R^{12}$ moieties are the same or different and each represent a monovalent substituted or unsubstituted hydrocarbon group. Examples of $R^{12}$ include the specific examples of the monovalent substituted or unsubstituted hydrocarbon groups mentioned above (e.g., alkyl groups, aryl groups, aralkyl groups, and halogenated hydrocarbon groups), and the alkenyl groups mentioned above. However, at least 2 of the $R^{12}$ moieties are alkenyl groups (particularly, a vinyl group). $R^{12}$ except for the alkenyl groups is preferably an alkyl group (particularly, an alkyl group having 1 to 10 carbon atoms) or an aryl group (particularly, an aryl group having 6 to 14 carbon atoms), particularly preferably a methyl group or a phenyl group.

In the formula (1-2), $R^4$ represents an alkylene group in the same way as above. Among others, a C144 alkylene group is preferred, and a C24 alkylene group (particularly, an ethylene group) is more preferred. When a plurality of $R^4$ moieties are present, these may be the same or different.

In the formula (1-2), r1 represents an integer of not less than 1 (e.g., 1 to 100). When r1 is an integer of not less than 2, the structures within the parentheses with r1 may be the same with or different from each other.

In the formula (1-2), r2 represents an integer of not less than 1 (e.g., 1 to 400). When r2 is an integer of not less than 2, the structures within the parentheses with r2 may be the same with or different from each other.

In the formula (1-2), r3 represents 0 or an integer of not less than 1 (e.g., 0 to 50). When r3 is an integer of not less than 2, the structures within the parentheses with r3 may be the same with or different from each other.

In the formula (1-2), r4 represents 0 or an integer of not less than 1 (e.g., 0 to 50). When r4 is an integer of not less than 2, the structures within the parentheses with r4 may be the same with or different from each other.

In the formula (1-2), r5 represents 0 or an integer of not less than 1 (e.g., 0 to 50). When r5 is an integer of not less than 2, the structures within the parentheses with r5 may be the same with or different from each other.

The addition form of each structural unit in the formula (1-2) is not particularly limited and may be a random form or may be a block form. The order in which these structural units are arranged is not particularly limited.

Examples of the terminal structure of the polyorganosiloxysilalkylene having a structure represented by the formula (1-2) include, but are not particularly limited to, silanol groups, alkoxysilyl groups, and trialkylsilyl groups (e.g., the structure within the parentheses with r5, and a trimethylsilyl group). Various groups such as an alkenyl group and a hydrosilyl group may be introduced to the end of the polyorganosiloxysilalkylene.

The polyorganosiloxysilalkylene (A2) can be produced by a method known in the art or routinely used. The production method is not particularly limited, and the polyorganosiloxysilalkylene (A2) can be produced by a method described in, for example, Japanese Patent Laid-Open No. 2012-140617. For example, trade names "ETERLED GD1130", "ETERLED GD1125", "ETERLED GS5145", "ETERLED GS5135", and "ETERLED GS5120" (all manufactured by Eternal Materials Co., Ltd.) are available as products containing the polyorganosiloxysilalkylene (A2).

In the curable resin composition of the present invention, one of these polysiloxanes (A) can be used alone, or not less than two thereof can be used in combination.

The content (total amount) of the polysiloxane (A) in the curable resin composition of the present invention is not particularly limited and is preferably 50 to 99% by weight, more preferably 60 to 97% by weight, further preferably 70 to 95% by weight, with respect to the total amount (100% by weight) of the curable resin composition. When the content is not less than 50% by weight, the resulting cured product tends to have stronger tenacity and improved transparency.

In the curable resin composition of the present invention, only the polyorganosiloxane (A1) can be used as the polysiloxane (A), or only the polyorganosiloxysilalkylene (A2) can be used thereas. Alternatively, the polyorganosiloxane (A1) and the polyorganosiloxysilalkylene (A2) can also be used in combination. In the case of using the polyorganosiloxane (A1) and the polyorganosiloxysilalkylene (A2) in combination, their proportions are not particularly limited and can be appropriately set. Likewise, in the curable resin composition of the present invention, only the polyorganosiloxane represented by the average unit formula (a-1) can be used as the polysiloxane (A), or only the polyorganosiloxysilalkylene represented by the average unit formula (a-2) can be used thereas. Alternatively, the polyorganosiloxane represented by the average unit formula (a-1) and the polyorganosiloxysilalkylene represented by the average unit formula (a-2) can also be used in combination.

The content (total amount) of the polyorganosiloxane represented by the average unit formula (a-1) and the polyorganosiloxysilalkylene represented by the average unit formula (a-2) in the polysiloxane (A) in the curable resin composition of the present invention is not particularly limited and is preferably not less than 50% by weight, more preferably not less than 60% by weight, further preferably not less than 70% by weight, still further preferably not less than 80% by weight, particularly preferably not less than 90% by weight, with respect to the total amount (100% by weight) of the polysiloxane (A). When the content is not less than 50% by weight, the resulting cured product tends to have lower tack properties and further resist adhesion of garbage. When the curable resin composition of the present invention comprises only one of the polyorganosiloxane represented by the average unit formula (a-1) and the polyorganosiloxysilalkylene represented by the average unit formula (a-2), the content described above is the content of the one.

[Polysiloxane (B)]

The polysiloxane (B) which is an essential component of the curable resin composition of the present invention is polysiloxane having not less than 2 hydrosilyl groups (Si—H) in the molecule, as mentioned above. Specifically, the polysiloxane (B) is polysiloxane having hydrosilyl groups and is a component that causes hydrosilylation reaction with a component having alkenyl groups (e.g., the polysiloxane (A)). However, the polysiloxane (B) excludes polysiloxane that corresponds to ladder-type polyorganosilsesquioxane (C) mentioned later.

The polysiloxane (B) is at least one polysiloxane selected from the group consisting of polyorganosiloxane (B1) having not less than 2 hydrosilyl groups in the molecule (also simply referred to as "polyorganosiloxane (B1)") and polyorganosiloxysilalkylene (B2) having not less than 2 hydrosilyl groups in the molecule (also simply referred to as "polyorganosiloxysilalkylene (B2)").

In the present specification, the polyorganosiloxysilalkylene (B2) is polysiloxane containing —Si—O—Si— (siloxane bond) as well as —Si—$R^4$—Si— (silalkylene bond; $R^4$ represents an alkylene group) in the backbone. In the present specification, the polyorganosiloxane (B1) is polysiloxane free from the silalkylene bond in the backbone. Examples of $R^4$ (alkylene group) in the silalkylene bond include linear or branched C1-14 alkylene groups, as in the description above. A linear or branched C2-4 alkylene group (particularly, an ethylene group) is preferred.

(Polyorganosiloxane (B1))

Examples of the polyorganosiloxane (B1) include polyorganosiloxane having a linear, partially branched linear, branched, or network molecular structure. One of these polyorganosiloxanes (B1) can be used alone, or not less than two thereof can be used in combination. Specifically, not less than 2 polyorganosiloxanes (B1) differing in molecular structure can be used in combination. For example, linear polyorganosiloxane (B1) and branched polyorganosiloxane (B1) can also be used in combination.

Examples of a group other than a hydrogen atom among the groups bonded to silicon atoms of the polyorganosiloxane (B1) include, but are not particularly limited to, the monovalent substituted or unsubstituted hydrocarbon groups mentioned above, more specifically alkyl groups, aryl groups, aralkyl groups, and halogenated hydrocarbon groups. Among them, an alkyl group (particularly, a methyl group) or an aryl group (particularly, a phenyl group) is preferred.

The polyorganosiloxane (B1) is not particularly limited by its nature and may be liquid or may be solid, for example, at 25° C. Particularly, the polyorganosiloxane (B1) is preferably liquid and is more preferably liquid with a viscosity of 0.1 to 1000000000 mPa·s at 25° C.

The polyorganosiloxane (B1) is preferably polyorganosiloxane represented by the following average unit formula (b-1):

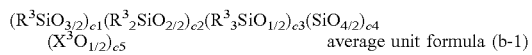

$(R^3SiO_{3/2})_{c1}(R^3{}_2SiO_{2/2})_{c2}(R^3{}_3SiO_{1/2})_{c3}(SiO_{4/2})_{c4}$
$(X^3O_{1/2})_{c5}$       average unit formula (b-1)

In the average unit formula (b-1), $R^3$ moieties are the same or different and each represent a hydrogen atom, an alkyl group having 1 to 10 carbon atoms, or an aryl group having 6 to 14 carbon atoms, provided that some of the $R^3$ moieties are hydrogen atoms (hydrogen atoms constituting the hydrosilyl groups), the proportion of which is controlled within the range of not less than 2 hydrosilyl groups in the molecule. For example, the ratio of the hydrogen atoms to the total amount (100% by mol) of the $R^3$ moieties is preferably 0.1 to 50% by mol. When the ratio of the hydrogen atoms is controlled within the range described above, the resulting curable resin composition tends to exhibit improved curing properties.

In the average unit formula (b-1), $X^3$ is a hydrogen atom or an alkyl group having 1 to 6 carbon atoms. Examples of the alkyl group having 1 to 6 carbon atoms include a methyl group, an ethyl group, a propyl group, a butyl group, a pentyl group, and a hexyl group. A methyl group is particularly preferred.

In the average unit formula (b-1), c1, c2, c3, c4, and c5 are numerical values satisfying 1>c1≥0, 1>c2≥0, 1>c3>0, 1>c4≥0, 0.05≥c5≥0, c1+c2+c4>0, and c1+c2+c3+c4+c5=1.

One example of the polyorganosiloxane (B1) includes linear polyorganosiloxane having not less than 2 hydrosilyl groups in the molecule. Examples of a group bonded to a silicon atom, except for the hydrogen atoms, in the linear polyorganosiloxane include the monovalent substituted or unsubstituted hydrocarbon groups mentioned above. Among them, an alkyl group (particularly, an alkyl group having 1 to 10 carbon atoms) or an aryl group (particularly, an aryl group having 6 to 14 carbon atoms) is preferred, and a methyl group or a phenyl group is particularly preferred.

The ratio of the hydrogen atoms (hydrogen atoms bonded to silicon atoms) to the total amount (100% by mol) of groups bonded to silicon atoms in the linear polyorganosiloxane is not particularly limited and is preferably 0.1 to 50% by mol. The ratio of the alkyl group (particularly, a methyl group) to the total amount (100% by mol) of groups bonded to silicon atoms is not particularly limited and is preferably 20 to 99% by mol. The ratio of the aryl group (particularly, a phenyl group) to the total amount (100% by mol) of groups bonded to silicon atoms is not particularly limited and is preferably 40 to 80% by mol. Particularly, use of the linear polyorganosiloxane in which the ratio of the aryl group (particularly, a phenyl group) to the total amount (100% by mol) of groups bonded to silicon atoms is not less than 40% by mol (e.g., 45 to 70% by mol) tends to further improve the barrier properties of a cured product against corrosive gas. Use of the linear polyorganosiloxane in which the ratio of the alkyl group (particularly, a methyl group) to the total amount (100% by mol) of groups bonded to silicon atoms is not less than 90% by mol (e.g., 95 to 99% by mol) tends to improve the thermal shock resistance of a cured product.

The linear polyorganosiloxane is represented by, for example, the following formula (II-1):

[Formula 11]

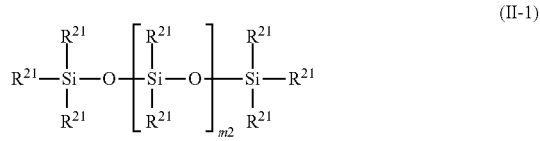

(II-1)

wherein $R^{21}$ moieties are the same or different and each represent a hydrogen atom or a monovalent substituted or unsubstituted hydrocarbon group, provided that at least 2 of the $R^{21}$ moieties are hydrogen atoms; and m2 is an integer of 1 to 1000.

Another example of the polyorganosiloxane (B1) includes branched polyorganosiloxane having not less than 2 hydrosilyl groups in the molecule and having a siloxane unit represented by $RSiO_{3/2}$ (T unit). However, the branched polyorganosiloxane excludes, as mentioned above, polyorganosiloxane that corresponds to ladder-type polyorganosilsesquioxane (C) mentioned later. R is a hydrogen atom or a monovalent substituted or unsubstituted hydrocarbon group. Examples of a group bonded to a silicon atom, except for the hydrogen atoms, in the branched polyorganosiloxane include the monovalent substituted or unsubstituted hydrocarbon groups mentioned above. Among them, an alkyl group (particularly, a methyl group) or an aryl group (particularly, a phenyl group) is preferred. Examples of R in the T unit include a hydrogen atom and the monovalent substituted or unsubstituted hydrocarbon groups mentioned above. Among them, an alkyl group (particularly, an alkyl group having 1 to 10 carbon atoms) or an aryl group (particularly, an aryl group having 6 to 14 carbon atoms) is preferred, and a methyl group or a phenyl group is particularly preferred. The ratio of the aryl group (particularly, a phenyl group) to the total amount (100% by mol) of R in the T unit is not particularly limited and is preferably not less than 30% by mol from the viewpoint of the barrier properties of a cured product against corrosive gas.

The ratio of the alkyl group (particularly, a methyl group) to the total amount (100% by mol) of groups bonded to silicon atoms in the branched polyorganosiloxane is not particularly limited and is preferably 70 to 95% by mol. The ratio of the aryl group (particularly, a phenyl group) to the total amount (100% by mol) of groups bonded to silicon atoms is not particularly limited and is preferably 10 to 70% by mol. Particularly, use of the branched polyorganosiloxane in which the ratio of the aryl group (particularly, a phenyl group) to the total amount (100% by mol) of groups bonded to silicon atoms is not less than 10% by mol (e.g., 10 to 70% by mol) tends to improve the barrier properties of a cured product against corrosive gas. Use of the branched polyorganosiloxane in which the ratio of the alkyl group (particularly, a methyl group) to the total amount (100% by mol) of groups bonded to silicon atoms is not less than 50% by mol (e.g., 50 to 90% by mol) tends to improve the thermal shock resistance of a cured product.

The branched polyorganosiloxane can be represented by, for example, the average unit formula (b-1) wherein c1 is a positive number. In this case, preferably, c2/c1 is a number of 0 to 10, c3/c1 is a number of 0 to 0.5, c4/(c1+c2+c3+c4) is a number of 0 to 0.3, and c5/(c1+c2+c3+c4) is a number of 0 to 0.4, though not particularly limited thereto. The molecular weight of the branched polyorganosiloxane is not particularly limited and is preferably 300 to 10000, more preferably 500 to 5000, in terms of the weight-average molecular weight based on standard polystyrene.

(Polyorganosiloxysilalkylene (B2))

The polyorganosiloxysilalkylene (B2) is polysiloxane having not less than 2 hydrosilyl groups in the molecule and containing a siloxane bond as well as a silalkylene bond in the backbone, as mentioned above. The alkylene group in the silalkylene bond is preferably, for example, a C24 alkylene group (particularly, an ethylene group).

Examples of the polyorganosiloxysilalkylene (B2) include polyorganosiloxysilalkylene having a linear, partially branched linear, branched, or network molecular structure. One of these polyorganosiloxysilalkylenes (B2) can be used alone, or not less than two thereof can be used in combination. Specifically, not less than 2 polyorganosiloxysilalkylenes (B2) differing in molecular structure can be used in combination. For example, linear polyorganosiloxysilalkylene (B2) and branched polyorganosiloxysilalkylene (B2) can also be used in combination.

Examples of a group bonded to a silicon atom, except for the hydrogen atoms, carried by the polyorganosiloxysilalkylene (B2) include, but are not particularly limited to, organic groups. Examples of the organic groups include the monovalent substituted or unsubstituted hydrocarbon groups mentioned above. Among them, an alkyl group (particularly, a methyl group) or an aryl group (particularly, a phenyl group) is preferred.

The polyorganosiloxysilalkylene (B2) is not particularly limited by its nature and may be liquid or may be solid, for example, at 25° C.

The polyorganosiloxysilalkylene (B2) is preferably polyorganosiloxysilalkylene represented by the following average unit formula (b-2):

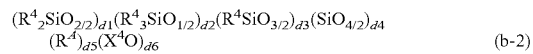

$(R^4{}_2SiO_{2/2})_{d1}(R^4{}_3SiO_{1/2})_{d2}(R^4SiO_{3/2})_{d3}(SiO_{4/2})_{d4}$
$(R^{A'})_{d5}(X^4O)_{d6}$ (b-2)

In the average unit formula (b-2), $R^4$ moieties are the same or different and each represent a hydrogen atom, an alkyl group having 1 to 10 carbon atoms, or an aryl group having 6 to 14 carbon atoms, provided that some of the $R^4$ moieties are hydrogen atoms, the proportion of which is controlled within the range of not less than 2 in the molecule. For example, the ratio of the hydrogen atoms to the total amount (100% by mol) of the $R^4$ moieties is preferably 0.1 to 50% by mol, more preferably 5 to 35% by mol. When the ratio of the hydrogen atoms is controlled within the range described above, the resulting curable resin composition tends to exhibit improved curing properties.

In the average unit formula (b-2), $R^{A'}$ is an alkylene group having 1 to 14 carbon atoms. Particularly, an ethylene group is preferred.

In the average unit formula (b-2), $X^4$ is a hydrogen atom or an alkyl group having 1 to 6 carbon atoms, as with $X^3$ described above. Examples of the alkyl group having 1 to 6 carbon atoms include a methyl group, an ethyl group, a propyl group, a butyl group, a pentyl group, and a hexyl group. Particularly, a methyl group is preferred.

In the average unit formula (b-2), d1, d2, d3, d4, d5, and d6 are numerical values satisfying $1 > d1 \geq 0$, $1 > d2 > 0$, $1 > d3 \geq 0$, $1 > d4 \geq 0$, $0.5 > d5 > 0$, $0.05 \geq d6 \geq 0$, $d1+d3+d4 > 0$, and $d1+d2+d3+d4+d5+d6=1$.

More specific examples of the polyorganosiloxysilalkylene (B2) include polyorganosiloxysilalkylene having a structure represented by the following formula (II-2):

[Formula 12]

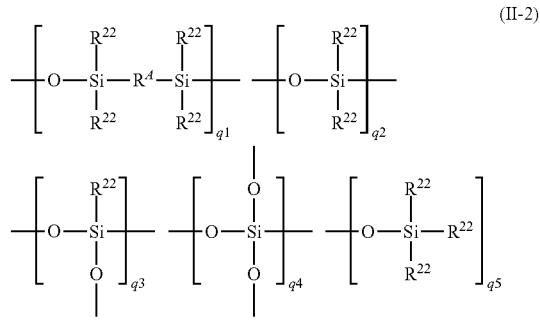

(II-2)

In the formula (II-2), $R^{22}$ moieties are the same or different and each represent a hydrogen atom or a monovalent substituted or unsubstituted hydrocarbon group. Examples of $R^{22}$ include a hydrogen atom and the specific examples of the monovalent substituted or unsubstituted hydrocarbon groups mentioned above (e.g., alkyl groups, aryl groups, aralkyl groups, and halogenated hydrocarbon groups). However, at least 2 of the $R^{22}$ moieties are hydrogen atoms. $R^{22}$ except for the hydrogen atoms is preferably an alkyl group (particularly an alkyl group having 1 to 10 carbon atoms) or an aryl group (particularly an aryl group having 6 to 14 carbon atoms), particularly preferably a methyl group or a phenyl group.

In the formula (II-2), $R^A$ represents an alkylene group, as with $R^A$ in the formula (1-2). Among others, a C24 alkylene group (particularly, an ethylene group) is preferred. When a plurality of $R^A$ moieties are present, these may be the same or different.

In the formula (II-2), q1 represents an integer of not less than 1 (e.g., 1 to 100). When q1 is an integer of not less than 2, the structures within the parentheses with q1 may be the same with or different from each other.

In the formula (II-2), q2 represents an integer of not less than 1 (e.g., 1 to 400). When q2 is an integer of not less than 2, the structures within the parentheses with q2 may be the same with or different from each other.

In the formula (II-2), q3 represents 0 or an integer of not less than 1 (e.g., 0 to 50). When q3 is an integer of not less than 2, the structures within the parentheses with q3 may be the same with or different from each other.

In the formula (II-2), q4 represents 0 or an integer of not less than 1 (e.g., 0 to 50). When q4 is an integer of not less than 2, the structures within the parentheses with q4 may be the same with or different from each other.

In the formula (II-2), q5 represents 0 or an integer of not less than 1 (e.g., 0 to 50). When q5 is an integer of not less than 2, the structures within the parentheses with q5 may be the same with or different from each other.

The addition form of each structural unit in the formula (II-2) is not particularly limited and may be a random form or may be a block form.

Examples of the terminal structure of the polyorganosiloxysilalkylene having a structure represented by the formula (II-2) include, but are not particularly limited to, silanol groups, alkoxysilyl groups, and trialkylsilyl groups (e.g., the structure within the parentheses with q5, and a trimethylsilyl group). Various groups such as a hydrosilyl group may be introduced to the end of the polyorganosiloxysilalkylene.

The polyorganosiloxysilalkylene (B2) can be produced by a method known in the art or routinely used. The production method is not particularly limited, and the polyorganosiloxysilalkylene (B2) can be produced by a method described in, for example, Japanese Patent Laid-Open No. 2012-140617.

In the curable resin composition of the present invention, one of these polysiloxanes (B) can be used alone, or not less than two thereof can be used in combination.

The content of the polysiloxane (B) in the curable resin composition of the present invention is not particularly limited and is preferably 1 to 200 parts by weight with respect to 100 parts by weight in total of the polysiloxane (A). When the content of the polysiloxane (B) is controlled within the range described above, the resulting curable resin composition tends to exhibit improved curing properties and be able to efficiently form a cured product. When the content of the polysiloxane (B) falls within the range described above, the resulting cured product tends to be improved in properties such as heat resistance, thermal shock resistance, and reflow resistance, for example, because curing reaction proceeds sufficiently.

In the curable resin composition of the present invention, only the polyorganosiloxane (B1) can be used as the polysiloxane (B), or only the polyorganosiloxysilalkylene (B2) can be used thereas. Alternatively, the polyorganosiloxane (B1) and the polyorganosiloxysilalkylene (B2) can also be used in combination. In the case of using the polyorganosiloxane (B1) and the polyorganosiloxysilalkylene (B2) in combination, their proportions are not particularly limited and can be appropriately set. Likewise, in the curable resin composition of the present invention, only the polyorganosiloxane represented by the average unit formula (b-1) can be used as the polysiloxane (B), or only the polyorganosiloxysilalkylene represented by the average unit formula (b-2) can be used thereas. Alternatively, the polyorganosiloxane represented by the average unit formula (b-1) and the polyorganosiloxysilalkylene represented by the average unit formula (b-2) can also be used in combination.

The content (total amount) of the polyorganosiloxane represented by the average unit formula (b-1) and the polyorganosiloxysilalkylene represented by the average unit formula (b-2) in the polysiloxane (B) in the curable resin composition of the present invention is not particularly limited and is preferably not less than 50% by weight, more preferably not less than 60% by weight, further preferably not less than 70% by weight, still further preferably not less than 80% by weight, particularly preferably not less than 90% by weight, with respect to the total amount (100% by weight) of the polysiloxane (B). When the content is not less than 50% by weight, the resulting cured product tends to have lower tack properties and further resist adhesion of garbage. When the curable resin composition of the present invention comprises only one of the polyorganosiloxane represented by the average unit formula (b-1) and the polyorganosiloxysilalkylene represented by the average unit formula (b-2), the content described above is the content of the one.

In the curable resin composition of the present invention, (i) the combination of the polysiloxane (A) comprising the branched polyorganosiloxane (A1) and the polysiloxane (B) comprising the polyorganosiloxane (B1), and/or (ii) the combination of the polysiloxane (A) comprising the polyorganosiloxysilalkylene (A2) having a group bonded to a silicon atom and the polysiloxane (B) comprising the polyorganosiloxysilalkylene (B2) is particularly preferred.

The sum of the contents (total content) of the polysiloxane (A) and the polysiloxane (B) in the curable resin composition of the present invention (100% by weight) is not particularly limited and is preferably 60 to 99% by weight, more preferably 70 to 96% by weight, further preferably 80 to 90% by weight. When the total content is controlled within the range described above, the resulting cured product tends to have stronger tenacity and improved heat resistance and transparency.

[Ladder-Type Polyorganosilsesquioxane (C)]

The curable resin composition of the present invention may comprise ladder-type polyorganosilsesquioxane (C). A cured product of the curable resin composition of the present invention comprising the ladder-type polyorganosilsesquioxane (C) tends to have high barrier properties against corrosive gas. The ladder-type polyorganosilsesquioxane (C) is polysiloxane represented by the empirical formula (basic structural formula) $RSiO_{1.5}$ and is polyorganosilsesquioxane containing at least a ladder-shaped Si—O—Si structure (ladder structure) in the molecule. The ladder-type polyorganosilsesquioxane (C) is preferably polysiloxane having a siloxane unit represented by $(RSiO_{3/2})$ and lacking a siloxane unit represented by $(R_2SiO_{2/2})$ and a siloxane unit represented by $(SiO_{4/2})$. In this case, the ladder-type polyorganosilsesquioxane (C) may or may not have a siloxane unit represented by $(R_3SiO_{1/2})$.

Polyorganosilsesquioxane known in the art or routinely used having the structure described above can be used as the ladder-type polyorganosilsesquioxane (C). The polyorganosilsesquioxane is not particularly limited and is preferably polyorganosilsesquioxane having not less than 1 (particularly not less than 2) aliphatic carbon-carbon double bond in the molecule or polyorganosilsesquioxane having not less than 1 (not less than 2) hydrosilyl group in the molecule. Also, the ladder-type polyorganosilsesquioxane (C) preferably has a substituted or unsubstituted aryl group (aromatic hydrocarbon group) at a portion or the whole of side chains [portions branched from a polyorganosilsesquioxane skeleton (skeleton formed by Si—O bonds) having a ladder structure, which is a principal skeleton (backbone)] from the viewpoint of the barrier properties of a cured product against corrosive gas. Examples of the substituted or unsubstituted aryl group include substituted or unsubstituted aryl groups listed as $R^5$ mentioned later.

The ladder-type polyorganosilsesquioxane is particularly preferably ladder-type silsesquioxane (C1) or ladder-type silsesquioxane (C2) described below, from the viewpoint of the barrier properties of a cured product against corrosive gas, its mechanical strength, etc.

(Ladder-Type Silsesquioxane (C1))

The ladder-type silsesquioxane (C1) as the ladder-type polyorganosilsesquioxane (C) is polyorganosilsesquioxane having a polyorganosilsesquioxane residue comprising a unit structure represented by the formula (V) and a unit structure represented by the formula (VI) mentioned later (also referred to as "polyorganosilsesquioxane residue (a)") at a portion or the whole of the molecular chain ends of the polyorganosilsesquioxane having a ladder structure (polyorganosilsesquioxane skeleton).

The polyorganosilsesquioxane (polyorganosilsesquioxane skeleton) in the ladder-type silsesquioxane (C1) is polysiloxane represented by the empirical formula (basic structural formula) $R^5SiO_{1.5}$. $R^5$ represents a hydrogen atom, a halogen atom, a monovalent organic group, a monovalent oxygen atom-containing group, a monovalent nitrogen atom-containing group, or a monovalent sulfur atom-containing group, and at least some of the $R^5$ moieties ($R^5$ moieties in the polyorganosilsesquioxane) are monovalent organic groups. The $R^5$ moieties in the polyorganosilsesquioxane may be the same with or different from each other.

Examples of the halogen atom represented by $R^5$ include a fluorine atom, a chlorine atom, a bromine atom, and an iodine atom. Examples of the monovalent organic group represented by $R^5$ include substituted or unsubstituted hydrocarbon groups (monovalent hydrocarbon groups), alkoxy groups, alkenyloxy groups, aryloxy groups, aralkyloxy groups, acyloxy groups, alkylthio groups, alkenylthio groups, arylthio groups, aralkylthio groups, a carboxy group, alkoxycarbonyl groups, aryloxycarbonyl groups, aralkyloxycarbonyl groups, an epoxy group, a cyano group, an isocyanate group, a carbamoyl group, and an isothiocyanate group.

Examples of the hydrocarbon group represented by $R^5$ include aliphatic hydrocarbon groups, alicyclic hydrocarbon groups, aromatic hydrocarbon groups, and groups having a linkage of not less than 2 of these groups.

Examples of the aliphatic hydrocarbon group represented by $R^5$ include alkyl groups, alkenyl groups, and alkynyl groups. Examples of the alkyl groups include $C_{1-20}$ alkyl groups such as a methyl group, an ethyl group, a propyl group, an isopropyl group, a butyl group, a hexyl group, an octyl group, an isooctyl group, a decyl group, and a dodecyl group (preferably C140 alkyl groups, more preferably $C_{1-4}$ alkyl groups). Examples of the alkenyl groups include C2-20 alkenyl groups such as a vinyl group, an allyl group, a methallyl group, a 1-propenyl group, an isopropenyl group, a 1-butenyl group, a 2-butenyl group, a 3-butenyl group, a 1-pentenyl group, a 2-pentenyl group, a 3-pentenyl group, a 4-pentenyl group, and a 5-hexenyl group (preferably C240 alkenyl groups, more preferably C24 alkenyl groups). Examples of the alkynyl groups include C2-20 alkynyl groups such as an ethynyl group and a propynyl group (preferably C240 alkynyl groups, more preferably C24 alkynyl groups).

Examples of the alicyclic hydrocarbon group represented by $R^5$ include: C342 cycloalkyl groups such as a cyclopropyl group, a cyclobutyl group, a cyclopentyl group, a cyclohexyl group, and a cyclododecyl group; C342 cycloalkenyl groups such as a cyclohexenyl group; and C445 bridged cyclic hydrocarbon groups such as a bicycloheptanyl group and a bicycloheptenyl group.

Examples of the aromatic hydrocarbon group represented by $R^5$ include aryl groups (e.g., $C_{6-14}$ aryl groups, particularly, $C_{6-10}$ aryl groups) such as a phenyl group and a naphthyl group.

Examples of the group in which an aliphatic hydrocarbon group and an alicyclic hydrocarbon group are bonded to each other, represented by $R^5$ include a cyclohexylmethyl group and a methylcyclohexyl group. Examples of the group in which an aliphatic hydrocarbon group and an aromatic hydrocarbon group are bonded to each other include: $C_{7-18}$ aralkyl groups such as a benzyl group and a phenethyl group (particularly, $C_{7-10}$ aralkyl groups); $C_{6-10}$ aryl-$C_{2-6}$ alkenyl groups such as a cinnamyl group; $C_{1-4}$ alkyl-substituted aryl groups such as a tolyl group; and $C_{2-4}$ alkenyl-substituted aryl groups such as a styryl group.

The hydrocarbon group represented by $R^5$ may be a hydrocarbon group having a substituent (substituted hydrocarbon group). The substituent on the substituted hydrocarbon group preferably has 0 to 20 carbon atoms, more preferably 0 to 10 carbon atoms. Examples of the substituent include: halogen atoms such as a fluorine atom, a chlorine atom, a bromine atom, and an iodine atom; a hydroxy group; alkoxy groups such as a methoxy group, an ethoxy group, a propoxy group, an isopropyloxy group, a butoxy group, and an isobutyloxy group (preferably $C_{1-6}$ alkoxy groups, more preferably $C_{1-4}$ alkoxy groups); alkenyloxy groups such as an allyloxy group (preferably $C_{2-6}$ alkenyloxy groups, more preferably $C_{2-4}$ alkenyloxy groups); aryloxy groups optionally having a substituent such as a $C_{1-4}$ alkyl group, a $C_{2-4}$ alkenyl group, a halogen atom, or a $C_{1-4}$ alkoxy group on the aromatic ring, such as a phenoxy group, a tolyloxy group, and a naphthyloxy group (preferably $C_{6-14}$ aryloxy groups); aralkyloxy groups such as a benzyloxy group and a phenethyloxy group (preferably $C_{7-18}$ aralkyloxy groups); acyloxy groups such as an acetyloxy group, a propionyloxy group, a (meth)acryloyloxy group, and a benzoyloxy group (preferably $C_{1-12}$ acyloxy groups); a mercapto group; alkylthio groups such as a methylthio group and an ethylthio group (preferably $C_{1-6}$ alkylthio groups, more preferably $C_{1-4}$ alkylthio groups); alkenylthio groups such as an allylthio group (preferably $C_{2-6}$ alkenylthio groups, more preferably $C_{2-4}$ alkenylthio groups); arylthio groups optionally having a substituent such as a $C_{1-4}$ alkyl group, a $C_{2-4}$ alkenyl group, a halogen atom, or a $C_{1-4}$ alkoxy group on the aromatic ring, such as a phenylthio group, a tolylthio group, and a naphthylthio group (preferably $C_{6-14}$ arylthio groups); aralkylthio groups such as a benzylthio group and a phenethylthio group (preferably $C_{7-18}$ aralkylthio groups); a carboxy group; alkoxycarbonyl groups such as a methoxycarbonyl group, an ethoxycarbonyl group, a propoxycarbonyl group, and a butoxycarbonyl group (preferably $C_{1-6}$ alkoxycarbonyl groups); aryloxycarbonyl groups such as a phenoxycarbonyl group, a tolyloxycarbonyl group, and a naphthyloxycarbonyl group (preferably $C_{6-14}$ aryloxy-carbonyl groups); aralkyloxycarbonyl groups such as a benzyloxy-carbonyl group (preferably $C_{7-18}$ aralkyloxy-carbonyl groups); an amino group; mono- or dialkylamino groups such as a methylamino group, an ethylamino group, a dimethylamino group, and a diethylamino group (preferably mono- or di-$C_{1-6}$ alkylamino groups); acylamino groups such as an acetylamino group, a propionylamino group, and a benzoylamino group (preferably $C_{1-11}$ acylamino groups); epoxy group-containing groups such as a glycidyloxy group; oxetanyl group-containing groups such as an ethyloxetanyloxy group; acyl groups such as an acetyl group, a propionyl group, and a benzoyl group; an oxo group; and groups in which not less than 2 of these groups are bonded, if necessary via a $C_{1-6}$ alkylene group. The number of the substituent carried by the substituted hydrocarbon group is not particularly limited.

Examples of the monovalent oxygen atom-containing group represented by $R^5$ include a hydroxy group, a hydroperoxy group, alkenyloxy groups, aryloxy groups, aralkyloxy groups, acyloxy groups, an isocyanate group, a sulfo group, and a carbamoyl group. Examples of the monovalent nitrogen atom-containing group include an amino group, substituted amino groups (mono- or dialkylamino groups, acylamino groups, etc.), a cyano group, an isocyanate group, an isothiocyanate group, and a carbamoyl group. Examples of the monovalent sulfur atom-containing group include a mercapto group (thiol group), a sulfo group, alkylthio groups, alkenylthio groups, arylthio groups, aralkylthio groups, and an isothiocyanate group. The monovalent organic group, the monovalent oxygen atom-containing group, the monovalent nitrogen atom-containing group, and the monovalent sulfur atom-containing group mentioned above may overlap with each other.

Further examples of $R^5$ described above include a group represented by the following formula (s):

[Formula 13]

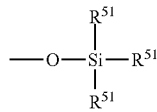

In the formula (s), $R^{51}$ (three $R^{51}$) moieties are the same or different and each represent a hydrogen atom, a halogen atom, a monovalent organic group, a monovalent oxygen atom-containing group, a monovalent nitrogen atom-containing group, or a monovalent sulfur atom-containing group. Examples of these groups include the same groups as those listed as $R^5$ described above.

In the group represented by the formula (s), each $R^{51}$ is preferably a hydrogen atom; a $C_{1-10}$ alkyl group (particularly, a $C_{1-4}$ alkyl group); a $C_{2-10}$ alkenyl group (particularly, a $C_{2-4}$ alkenyl group); a $C_{3-12}$ cycloalkyl group; a $C_{3-12}$ cycloalkenyl group; a $C_{6-14}$ aryl group optionally having a substituent such as a $C_{1-4}$ alkyl group, a $C_{2-4}$ alkenyl group, a halogen atom, or a $C_{1-4}$ alkoxy group on the aromatic ring; a $C_{7-18}$ aralkyl group; a $C_{6-10}$ aryl-$C_{2-6}$ alkenyl group; a hydroxy group; a $C_{1-6}$ alkoxy group; or a halogen atom.

Among them, $R^5$ is preferably a hydrogen atom or a substituted or unsubstituted hydrocarbon group, more preferably a substituted or unsubstituted hydrocarbon group, further preferably an aliphatic hydrocarbon group (particularly, an alkyl group) or an aromatic hydrocarbon group (particularly, a phenyl group).

General examples of the polyorganosilsesquioxane structure include a ladder-shaped Si—O—Si structure (ladder structure), a cage-shaped Si—O—Si structure (caged structure), and a random-shaped Si—O—Si structure (random structure). The polyorganosilsesquioxane in the ladder-type silsesquioxane (C1) is polyorganosilsesquioxane containing at least the ladder structure described above (polyorganosilsesquioxane having the ladder structure).

The polyorganosilsesquioxane in the ladder-type silsesquioxane (C1) is represented by, for example, the following formula (L):

[Formula 14]

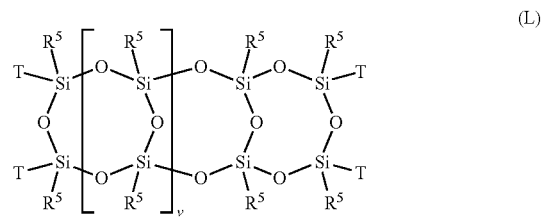

In the formula (L), v represents an integer of not less than 1 (e.g., 1 to 5000) and is preferably an integer of 1 to 2000, more preferably an integer of 1 to 1000. In the formula (L), $R^5$ represents the same as $R^5$ described above. T represents a terminal group.

Groups directly bonded to a silicon atom ($R^5$ in the empirical formula, for example, $R^5$ (side chain) in the formula (L)) in the polyorganosilsesquioxane in the ladder-type silsesquioxane (C1) are not particularly limited. The ratio of a substituted or unsubstituted hydrocarbon group to the total amount (100% by mol) of the groups is preferably not less than 50% by mol, more preferably not less than 80% by mol, further preferably not less than 90% by mol. Particularly, the total amount of a substituted or unsubstituted linear or branched $C_{1-10}$ alkyl group (particularly, a linear or branched $C_{1-4}$ alkyl group such as a methyl group or an ethyl group), a substituted or unsubstituted $C_{6-10}$ aryl group (particularly, a phenyl group), and a substituted or unsubstituted $C_{7-10}$ aralkyl group (particularly, a benzyl group) with respect to the total amount (100% by mol) of the groups is preferably not less than 50% by mol, more preferably not less than 80% by mol, further preferably not less than 90% by mol.

Particularly, the ladder-type silsesquioxane (C1) preferably has a substituted or unsubstituted aryl group (aromatic hydrocarbon group) at a portion or the whole of side chains [portions branched from a polyorganosilsesquioxane skeleton having a ladder structure, which is a principal skeleton (backbone); for example, $R^5$ in the formula (L)], from the viewpoint of the barrier properties of a cured product against corrosive gas.

The ladder-type silsesquioxane (C1) has at least the polyorganosilsesquioxane residue (a) at a portion or the whole of the molecular chain ends of the polyorganosilsesquioxane having the ladder structure described above. When the polyorganosilsesquioxane is represented by the formula (L), the ladder-type silsesquioxane (C1) has a structure represented by the formula (L) wherein a portion or the whole of the T moieties are substituted by the polyorganosilsesquioxane residue (a) given below.

The polyorganosilsesquioxane residue (a) is a residue comprising at least a unit structure represented by the following formula (V):

[Formula 15]

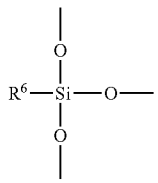
(V)

(siloxane unit structure) and a unit structure represented by the following formula (VI):

[Formula 16]

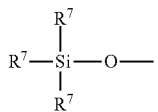
(VI)

(siloxane unit structure).

In the formula (V), $R^6$ represents a group having an aliphatic carbon-carbon double bond. Examples of the group having an aliphatic carbon-carbon double bond include: $C_{2-20}$ alkenyl groups such as a vinyl group, an allyl group, a methallyl group, a 1-propenyl group, an isopropenyl group, a 1-butenyl group, a 2-butenyl group, a 3-butenyl group, a 1-pentenyl group, a 2-pentenyl group, a 3-pentenyl group, a 4-pentenyl group, and a 5-hexenyl group (preferably $C_{2-10}$ alkenyl groups, more preferably $C_{2-4}$ alkenyl groups); $C_{3-12}$ cycloalkenyl groups such as a cyclohexenyl group; $C_{4-15}$ bridged cyclic unsaturated hydrocarbon groups such as a bicycloheptenyl group; $C_{2-4}$ alkenyl-substituted aryl groups such as a styryl group; and a cinnamyl group. The group having an aliphatic carbon-carbon double bond also includes a group represented by the formula (s) wherein at least one of the three $R^{51}$ moieties is selected from the $C_{2-20}$ alkenyl groups, the $C_{3-12}$ cycloalkenyl groups, the $C_{4-15}$ bridged cyclic unsaturated hydrocarbon groups, the $C_{2-4}$ alkenyl-substituted aryl groups, the cinnamyl group, and the like. Among others, $R^6$ is preferably an alkenyl group, more preferably a $C_{2-20}$ alkenyl group, further preferably a vinyl group.

In the formula (VI), $R^7$ moieties are the same or different and each represent a hydrocarbon group (monovalent hydrocarbon group). Examples of the hydrocarbon group include the same hydrocarbon groups as those listed as $R^5$ described above. Among others, $R^7$ is preferably a $C_{1-20}$ alkyl group, more preferably a $C_{1-10}$ alkyl group, further preferably a $C_{1-4}$ alkyl group, particularly preferably a methyl group. Particularly, all of the $R^7$ moieties in the formula (VI) are preferably methyl groups.

The polyorganosilsesquioxane residue (a) may have, for example, a unit structure represented by the following formula (V):

[Formula 17]

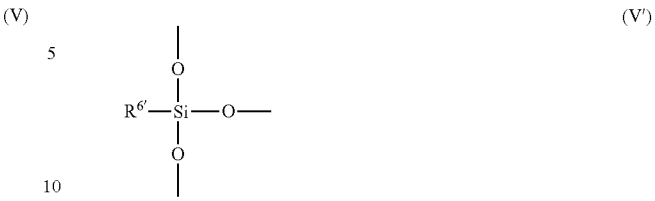
(V')

(siloxane unit structure) in addition to the unit structure represented by the formula (V) and the unit structure represented by the formula (VI).

In the formula (V'), $R^{6'}$ represents a monovalent group except for the group having an aliphatic carbon-carbon double bond. Specific examples thereof include a hydrogen atom, halogen atoms, monovalent organic groups except for the group having an aliphatic carbon-carbon double bond, monovalent oxygen atom-containing groups, monovalent nitrogen atom-containing groups, and monovalent sulfur atom-containing groups.

The amount of the silicon atom bonded to three oxygen atoms in the formula (V) in the polyorganosilsesquioxane residue (a) is not particularly limited and is preferably 20 to 80% by mol, more preferably 25 to 60% by mol, with respect to the total amount (100% by mol) of silicon atoms constituting the polyorganosilsesquioxane residue (a). If the content is less than 20% by mol, the resulting cured product may not have adequate hardness due to an insufficient amount of an aliphatic carbon-carbon double bond (particularly, an alkenyl group) in the ladder-type silsesquioxane (C1). On the other hand, if the content is more than 80% by mol, the ladder-type silsesquioxane (C1) may not be obtained in a liquid state because many silanol groups or hydrolyzable silyl groups remain in the ladder-type silsesquioxane (C1). Furthermore, preservation stability may be deteriorated because condensation reaction proceeds so that the molecular weight varies easily.

The amount of the silicon atom bonded to one oxygen atom in the formula (VI) in the polyorganosilsesquioxane residue (a) is not particularly limited and is preferably 20 to 85% by mol, more preferably 30 to 75% by mol, with respect to the total amount (100% by mol) of silicon atoms constituting the polyorganosilsesquioxane residue (a). If the content is less than 20% by mol, the ladder-type silsesquioxane (C1) may not be obtained in a liquid state because silanol groups or hydrolyzable silyl groups are more likely to remain in the ladder-type silsesquioxane (C1). Furthermore, preservation stability may be deteriorated because condensation reaction proceeds so that the molecular weight varies easily. On the other hand, if the content is more than 85% by mol, the resulting cured product may not have adequate hardness due to an insufficient amount of an aliphatic carbon-carbon double bond (particularly, an alkenyl group) in the ladder-type silsesquioxane (C1).

Examples of the Si—O—Si structure (skeleton) of the polyorganosilsesquioxane residue (a) include, but are not particularly limited to, a ladder structure, a caged structure, and a random structure.

The ladder-type silsesquioxane (C1) can be represented by, for example, the formula ($L^a$) given below. In the formula ($L^a$), examples of v and $R^5$ include the same as those in the formula (L). In the formula ($L^a$), A represents the polyorganosilsesquioxane residue (a) or a hydroxy group, a halogen atom, an alkoxy group, or an acyloxy group, and a portion or the whole of the A moieties is the polyorganosilsesquioxane residue (a). When a plurality (2 to 4) of A moieties in the formula (L^a) are polyorganosilsesquioxane residues (a), each A may bind to A of the same molecule or a different molecule represented by the formula (L^a) via not less than 1 Si—O—Si bond.

[Formula 18]

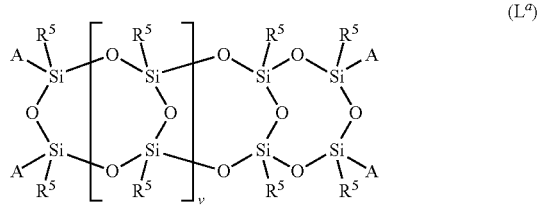

The polyorganosilsesquioxane residue (a) in the ladder-type silsesquioxane (C1) may further have a unit structure represented by the formula (VII) in ladder-type silsesquioxane (C2) mentioned later. In this case, the ladder-type silsesquioxane (C1) may be used as the ladder-type silsesquioxane (C2).

Examples of a method for producing the ladder-type silsesquioxane (C1) include, but are not particularly limited to, a method which involves forming the polyorganosilsesquioxane residue (a) at the molecular chain ends of polyorganosilsesquioxane having a ladder structure and having a silanol group and/or a hydrolyzable silyl group (any one of a silanol group and a hydrolyzable silyl group, or both) at the molecular chain ends. Specifically, the ladder-type silsesquioxane (C1) can be produced by, for example, a method disclosed in a literature such as International Publication No. WO 2013/176238.

The number of intramolecular aliphatic carbon-carbon double bonds (particularly, alkenyl groups) in the ladder-type silsesquioxane (C1) is not particularly limited and is preferably not less than 2 (e.g., 2 to 50), more preferably 2 to 30. The ladder-type silsesquioxane (C1) having aliphatic carbon-carbon double bonds (particularly, alkenyl groups) within the range described above tends to facilitate obtaining a cured product excellent in various physical properties such as heat resistance, crack resistance, and barrier properties against corrosive gas.

The content of the aliphatic carbon-carbon double bonds in the ladder-type silsesquioxane (C1) is not particularly limited and is preferably 0.7 to 5.5 mmol/g, more preferably 1.1 to 4.4 mmol/g. The proportion (based on weight) of the aliphatic carbon-carbon double bonds contained in the ladder-type silsesquioxane (C1) is not particularly limited and is preferably 2.0 to 15.0% by weight, more preferably 3.0 to 12.0% by weight, based on a vinyl group.

The molecular weight of the ladder-type silsesquioxane (C1) is not particularly limited and is preferably 100 to 800000, more preferably 200 to 100000, further preferably 300 to 10000, particularly preferably 500 to 8000. The ladder-type silsesquioxane (C1) having a molecular weight within this range tends to be easily handled because of easily becoming liquid at room temperature and easily having relatively low viscosity. The ladder-type silsesquioxane (C1) may be a mixture of silsesquioxanes having various molecular weights within the range described above. The molecular weight is measured as a molecular weight based on standard polystyrene by gel permeation chromatography.

The weight-average molecular weight (Mw) of the ladder-type silsesquioxane (C1) is not particularly limited and is preferably 100 to 800000, more preferably 200 to 100000, further preferably 300 to 10000, particularly preferably 500 to 8000. When the weight-average molecular weight is not less than 100, the resulting cured product tends to exhibit improved heat resistance. On the other hand, when the molecular weight is not more than 800000, compatibility with other components tends to be improved. The weight-average molecular weight is calculated from the molecular weight based on standard polystyrene by gel permeation chromatography.

The ladder-type silsesquioxane (C1) is not particularly limited and is preferably liquid at ordinary temperature (approximately 25° C.). More specifically, the viscosity of the ladder-type silsesquioxane (C1) at 23° C. is preferably 100 to 100000 mPa·s, more preferably 500 to 10000 mPa·s, further preferably 1000 to 8000 mPa·s. When the viscosity is not less than 100 mPa·s, the resulting cured product tends to exhibit improved heat resistance. On the other hand, when the viscosity is not more than 100000 mPa·s, the resulting curable resin composition tends to be easy to prepare or handle. The viscosity at 23° C. is measured using a rheometer (trade name "Physica UDS-200", manufactured by Anton Paar GmbH) and a cone plate (cone diameter: 16 mm, taper angle=0°) under conditions involving a temperature of 23° C. and the number of revolutions of 20 rpm.

In the curable resin composition of the present invention, one of these ladder-type silsesquioxanes (C1) can be used alone, or not less than two thereof can be used in combination.

When the curable resin composition of the present invention comprises the ladder-type silsesquioxane (C1), the content of the ladder-type silsesquioxane (C1) in the curable resin composition of the present invention is not particularly limited and is preferably 1 to 40% by weight, more preferably 5 to 30% by weight, further preferably 10 to 20% by weight, with respect to the curable resin composition (100% by weight). When the content is not less than 1% by weight, the resulting cured product tends to exhibit further improved barrier properties against corrosive gas. On the other hand, when the content is not more than 40% by weight, the resulting cured product tends to be prevented from being too hard and be excellent in flexibility.

(Ladder-Type Silsesquioxane (C2))

The ladder-type silsesquioxane (C2) in the curable resin composition of the present invention is polyorganosilsesquioxane having a polyorganosilsesquioxane residue comprising a unit structure represented by the formula (VII) and a unit structure represented by the formula (VIII) mentioned later (also referred to as a "polyorganosilsesquioxane residue (b)") at a portion or the whole of the molecular chain ends of the polyorganosilsesquioxane having a ladder structure (polyorganosilsesquioxane skeleton).

The polyorganosilsesquioxane in the ladder-type silsesquioxane (C2) is polysiloxane represented by the empirical formula (basic structural formula) $R^5SiO_{1.5}$. Examples of the polyorganosilsesquioxane in the ladder-type silsesquioxane (C2) include the same as the polyorganosilsesquioxane (e.g., polyorganosilsesquioxane represented by the formula (L)) in the ladder-type silsesquioxane (C1).

The ladder-type silsesquioxane (C2) particularly preferably has a substituted or unsubstituted aryl group at a portion or the whole of side chains, as with the ladder-type silsesquioxane (C1), from the viewpoint of the barrier properties of a cured product against corrosive gas.

When the polyorganosilsesquioxane is represented by the formula (L), the ladder-type silsesquioxane (C2) has a structure represented by the formula (L) wherein a portion or the whole of the T moieties is substituted by the polyorganosilsesquioxane residue (b) given below.

The polyorganosilsesquioxane residue (b) is a residue comprising at least a unit structure represented by the following formula (VII):

[Formula 19]

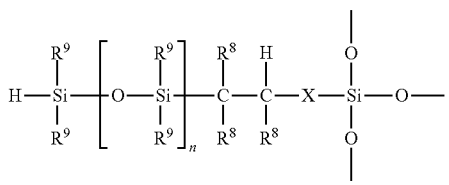

(siloxane unit structure) and a unit structure represented by the following formula (VIII):

[Formula 20]

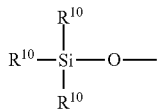

(siloxane unit structure). The organic group ($-X-CHR^8-CR^8{}_2-[SiR^9{}_2-O-]_n-SiHR^9{}_2$) in the unit structure represented by the formula (VII) is also referred to as a "SiH-containing group".

In the formula (VII), X represents a single bond or a linking group (divalent group having not less than 1 atom). Examples of the linking group include divalent hydrocarbon groups, a carbonyl group, an ether group (ether bond), a thioether group (thioether bond), an ester group (ester bond), a carbonate group (carbonate bond), an amide group (amide bond), and groups having a linkage of two or more of these groups.

Examples of the divalent hydrocarbon groups include linear or branched alkylene groups having 1 to 18 carbon atoms and divalent alicyclic hydrocarbon groups. Examples of the linear or branched alkylene groups having 1 to 18 carbon atoms include a methylene group, a methylmethylene group, a dimethylmethylene group, an ethylene group, a propylene group, and a trimethylene group. Examples of the divalent alicyclic hydrocarbon groups include divalent cycloalkylene groups (including cycloalkylidene groups) such as a 1,2-cyclopentylene group, a 1,3-cyclopentylene group, a cyclopentylidene group, a 1,2-cyclohexylene group, a 1,3-cyclohexylene group, a 1,4-cyclohexylene group, and a cyclohexylidene group.

In the formula (VII), $R^8$ moieties are the same or different and each represent a hydrogen atom, a halogen atom, a monovalent organic group, a monovalent oxygen atom-containing group, a monovalent nitrogen atom-containing group, or a monovalent sulfur atom-containing group. Examples of $R^8$ include the same groups as those listed as $R^5$ described above. Among others, each $R^8$ is preferably a hydrogen atom or a substituted or unsubstituted hydrocarbon group, more preferably a hydrogen atom.

In the formula (VII), $R^9$ moieties are the same or different and each represent a hydrogen atom, a halogen atom, a monovalent organic group, a monovalent oxygen atom-containing group, a monovalent nitrogen atom-containing group, or a monovalent sulfur atom-containing group. Examples of $R^9$ include the same groups as those listed as $R^5$ described above. When n in the formula (VII) is an integer of not less than 2, the $R^9$ moieties within the parentheses with n may be the same with or different from each other.

Among them, each $R^9$ is preferably a hydrogen atom or a substituted or unsubstituted hydrocarbon group, more preferably a substituted or unsubstituted hydrocarbon group, further preferably an aliphatic hydrocarbon group (particularly, a methyl group) or an aromatic hydrocarbon group (particularly, a phenyl group).

In the formula (VII), n represents an integer of 1 to 100 and is preferably an integer of 1 to 30, more preferably an integer of 1 to 10, further preferably an integer of 1 to 5. If n is too large, the resulting cured product tends to have reduced barrier properties against gas (particularly, corrosive gas) and therefore, may not be suitable as a sealing agent for, for example, optical semiconductor devices.

In the formula (VIII), $R^{10}$ moieties are the same or different and each represent a hydrocarbon group (monovalent hydrocarbon group). Examples of the hydrocarbon group include the same hydrocarbon groups as those listed as $R^5$ described above. Among others, $R^{10}$ is preferably a $C_{1-20}$ alkyl group, more preferably a $C_{1-10}$ alkyl group, further preferably a $C_{1-4}$ alkyl group, particularly preferably a methyl group. Particularly, all of the $R^{10}$ moieties in the formula (VIII) are preferably methyl groups.

The polyorganosilsesquioxane residue (b) may have, for example, a unit structure represented by the formula (V), in addition to the unit structure represented by the formula (VII) and the unit structure represented by the formula (VIII).

The amount of the silicon atom (excluding the silicon atoms in the SiH-containing group) bonded to three oxygen atoms in the formula (VII) in the polyorganosilsesquioxane residue (b) is not particularly limited and is preferably 20 to 80% by mol, more preferably 25 to 60% by mol, with respect to the total amount (100% by mol) of silicon atoms constituting the polyorganosilsesquioxane residue (b). If the content is less than 20% by mol, the resulting cured product may not have adequate hardness due to an insufficient amount of an hydrosilyl group in the ladder-type silsesquioxane (C2). On the other hand, if the content is more than 80% by mol, the ladder-type silsesquioxane (C2) may not be obtained in a liquid state because many silanol groups or hydrolyzable silyl groups remain in the ladder-type silsesquioxane (C2). Furthermore, preservation stability may be deteriorated because condensation reaction proceeds so that the molecular weight varies easily.

The amount of the silicon atom bonded to one oxygen atom in the formula (VIII) in the polyorganosilsesquioxane residue (b) is not particularly limited and is preferably 20 to 85% by mol, more preferably 30 to 75% by mol, with respect to the total amount (100% by mol) of silicon atoms constituting the polyorganosilsesquioxane residue (b). If the content is less than 20% by mol, the ladder-type silsesquioxane (C2) may not be obtained in a liquid state because silanol groups or hydrolyzable silyl groups are more likely to remain in the ladder-type silsesquioxane (C2). Furthermore, preservation stability may be deteriorated because condensation reaction proceeds so that the molecular weight varies easily. On the other hand, if the content is more than 85% by mol, the resulting cured product may not have adequate hardness due to an insufficient amount of a hydrosilyl group in the ladder-type silsesquioxane (C2).

Examples of the Si—O—Si structure (skeleton) of the polyorganosilsesquioxane residue (b) include, but are not particularly limited to, a ladder structure, a caged structure, and a random structure.

The ladder-type silsesquioxane (C2) can be represented by, for example, the formula ($L^b$) given below. In the formula ($L^b$), examples of v and $R^5$ include the same as those in the formula (L). In the formula ($L^b$), B represents the polyorganosilsesquioxane residue (b) or a hydroxy group, a halogen atom, an alkoxy group, or an acyloxy group, and a portion or the whole of the B moieties in the formula ($L^b$) is the polyorganosilsesquioxane residue (b). When a plurality (2 to 4) of B moieties in the formula ($L^b$) are polyorganosilsesquioxane residues (b), each B may bind to B of the same molecule or a different molecule represented by the formula ($L^b$) via not less than 1 Si—O—Si bond.

[Formula 21]

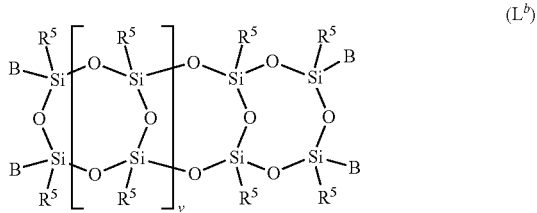

($L^b$)

The polyorganosilsesquioxane residue (b) in the ladder-type silsesquioxane (C2) may further have a unit structure represented by the formula (V) in the ladder-type silsesquioxane (C1) mentioned above. In this case, the ladder-type silsesquioxane (C2) may be used as the ladder-type silsesquioxane (C1).

Examples of a method for producing the ladder-type silsesquioxane (C2) include, but are not particularly limited to, a method which involves forming the polyorganosilsesquioxane residue (b) at the molecular chain ends of polyorganosilsesquioxane having a ladder structure and having a silanol group and/or a hydrolyzable silyl group at the molecular chain ends (starting material ladder polymer). Specifically, the ladder-type silsesquioxane (C2) can be produced by, for example, a method disclosed in a literature such as International Publication No. WO 2013/176238.

The number of the SiH-containing group in the molecule (in one molecule) of the ladder-type silsesquioxane (C2) is not particularly limited and is preferably not less than 2 (e.g., 2 to 50), more preferably 2 to 30. A cured product of the curable resin composition having the SiH-containing group within the range described above tends to exhibit improved heat resistance.

The content of the hydrosilyl group in the ladder-type silsesquioxane (C2) is not particularly limited and is preferably 0.01 to 0.5 mmol/g, more preferably 0.08 to 0.28 mmol/g. The content based on weight of the hydrosilyl group in the ladder-type silsesquioxane (C2) is not particularly limited and is preferably 0.01 to 0.50% by weight, more preferably 0.08 to 0.28% by weight, based on the weight of H (hydride) (based on H) in the hydrosilyl group. If the content of the hydrosilyl group is too small (e.g., less than 0.01 mmol/g or less than 0.01% by weight based on H), the curing of the curable resin composition may not proceed. On the other hand, if the content of the hydrosilyl group is too large (e.g., more than 0.50 mmol/g or more than 0.50% by weight based on H), the resulting cured product may be easily broken due to high hardness. The content of the hydrosilyl group in the ladder-type silsesquioxane (C2) can be calculated by, for example, $^1$H-NMR spectrum measurement.

The molecular weight of the ladder-type silsesquioxane (C2) is not particularly limited and is preferably 100 to 800000, more preferably 200 to 100000, further preferably 300 to 10000, particularly preferably 500 to 9000. The ladder-type silsesquioxane (C2) having a molecular weight within this range tends to be easily handled because of easily becoming liquid at room temperature and easily having relatively low viscosity. The ladder-type silsesquioxane (C2) may be a mixture of silsesquioxanes having various molecular weights within the range described above. The molecular weight is measured as a molecular weight based on standard polystyrene by gel permeation chromatography.

The weight-average molecular weight (Mw) of the ladder-type silsesquioxane (C2) is not particularly limited and is preferably 100 to 800000, more preferably 200 to 100000, further preferably 300 to 10000, particularly preferably 500 to 9000. When the weight-average molecular weight is not less than 100, the resulting cured product tends to exhibit improved heat resistance. On the other hand, when the molecular weight is not more than 800000, compatibility with other components tends to be improved. The weight-average molecular weight is calculated from the molecular weight based on standard polystyrene by gel permeation chromatography.

The ladder-type silsesquioxane (C2) is not particularly limited and is preferably liquid at ordinary temperature (approximately 25° C.). More specifically, the viscosity of the ladder-type silsesquioxane (C2) at 23° C. is preferably 100 to 100000 mPa·s, more preferably 500 to 10000 mPa·s, further preferably 1000 to 8000 mPa·s. When the viscosity is not less than 100 mPa·s, the resulting cured product tends to exhibit improved heat resistance. On the other hand, when the viscosity is not more than 100000 mPa·s, the resulting curable resin composition tends to be easy to prepare or handle. The viscosity at 23° C. is measured in the same way as in the viscosity of the ladder-type silsesquioxane (C1).

In the curable resin composition of the present invention, one of these ladder-type silsesquioxanes (C2) can be used alone, or not less than two thereof can be used in combination.

When the curable resin composition of the present invention comprises the ladder-type silsesquioxane (C2), the content of the ladder-type silsesquioxane (C2) in the curable resin composition of the present invention is not particularly limited and is preferably 1 to 30% by weight, more preferably 3 to 20% by weight, further preferably 5 to 15% by weight, with respect to the curable resin composition (100% by weight). When the content is not less than 1% by weight, the resulting cured product tends to exhibit further improved barrier properties against corrosive gas. Furthermore, the curing reaction of the curable resin composition proceeds sufficiently because of a large amount of a hydrosilyl group. As a result, the resulting cured product tends to have high hardness. On the other hand, when the content is not more than 30% by weight, the resulting cured product tends to be prevented from being too hard and be excellent in flexibility.

(Additional Ladder-Type Silsesquioxane)

Ladder-type silsesquioxane other than the ladder-type silsesquioxane (C1) and the ladder-type silsesquioxane (C2) mentioned above (also referred to as "additional ladder-type silsesquioxane") can also be used as the ladder-type polyorganosilsesquioxane (C). Particularly, the additional ladder-type silsesquioxane is preferably used in combination with the ladder-type silsesquioxane (C1) or the ladder-type silsesquioxane (C2).

Examples of the additional ladder-type silsesquioxane include: ladder-type silsesquioxane that is solid at 25° C. and has an aliphatic carbon-carbon double bond (particularly, an alkenyl group) (also referred to as "ladder-type silsesquioxane (S1));" and ladder-type silsesquioxane that is solid at 25° C. and has a hydrosilyl group (also referred to as "ladder-type silsesquioxane (S2)"). Particularly, a cured product of the curable resin composition of the present invention comprising the ladder-type silsesquioxane (S1) and/or (S2) tends to exhibit improved barrier properties against corrosive gas and stronger tenacity (particularly, improved crack resistance).

The number of intramolecular aliphatic carbon-carbon double bonds (particularly, alkenyl groups) in the ladder-type silsesquioxane (S1) is not particularly limited and is preferably not less than 2 (e.g., 2 to 50), more preferably 2 to 30. The position of the aliphatic carbon-carbon double bond (particularly, an alkenyl group) in the ladder-type silsesquioxane (S1) is not particularly limited and may be a side chain or may be an end.

The number of intramolecular hydrosilyl groups in the ladder-type silsesquioxane (S2) is not particularly limited and is preferably not less than 2 (e.g., 2 to 50), more preferably 2 to 30. The position of the hydrosilyl group in the ladder-type silsesquioxane (S2) is not particularly limited and may be a side chain or may be an end.

The weight-average molecular weight (Mw) of the ladder-type silsesquioxane (S1) or (S2) is not particularly limited and is preferably 2000 to 800000, more preferably 6000 to 100000. When the weight-average molecular weight is not less than 2000, the resulting cured product tends to exhibit improved barrier properties against corrosive gas. On the other hand, when the molecular weight is not more than 800000, compatibility with other components tends to be improved. The weight-average molecular weight is calculated from the molecular weight based on standard polystyrene by gel permeation chromatography.

The ladder-type silsesquioxane (S1) or (S2) can be produced by a ladder-type silsesquioxane production method known in the art or routinely used (e.g., sol-gel method using a trifunctional silane compound as a starting material).

When the curable resin composition of the present invention comprises the ladder-type silsesquioxane (S1), the content of the ladder-type silsesquioxane (S1) is not particularly limited and can be appropriately adjusted to within the range of, for example, 0.1 to 30% by weight with respect to the curable resin composition (100% by weight). When the curable resin composition of the present invention comprises the ladder-type silsesquioxane (S2), the content of the ladder-type silsesquioxane (S2) is not particularly limited and can be appropriately adjusted to within the range of, for example, 0.1 to 30% by weight with respect to the curable resin composition (100% by weight).

For example, ladder-type silsesquioxane having not less than 2 aliphatic carbon-carbon double bonds (particularly, alkenyl groups) in the molecule or not less than 2 hydrosilyl groups in the molecule and having a number-average molecular weight (Mn) of 500 to 1500 based on standard polystyrene in gel permeation chromatography and a molecular weight distribution (Mw/Mn) of 1.00 to 1.40, as disclosed in International Publication No. WO 2013/176238 can also be used as the additional ladder-type silsesquioxane. Use of such ladder-type silsesquioxane tends to remarkably improve the barrier properties of a cured product against corrosive gas. The content of the ladder-type silsesquioxane is not particularly limited and can be appropriately adjusted to within the range of, for example, 0.1 to 15% by weight with respect to the curable resin composition (100% by weight).

In the curable resin composition of the present invention, one of these ladder-type polyorganosilsesquioxanes can be used alone, or not less than two thereof can be used in combination. Particularly, the ladder-type silsesquioxane (C1) and the ladder-type silsesquioxane (C2) are preferably used in combination from the viewpoint of the barrier properties of a cured product against corrosive gas.

When the curable resin composition of the present invention comprises the ladder-type polyorganosilsesquioxane (C), the content of the ladder-type polyorganosilsesquioxane (C) in the curable resin composition of the present invention is not particularly limited and is preferably 0.1 to 50% by weight, more preferably 0.5 to 40% by weight, further preferably 0.5 to 30% by weight, with respect to the curable resin composition (100% by weight). When the content of the ladder-type polyorganosilsesquioxane (C) is not less than 0.1% by weight, the resulting cured product tends to exhibit further improved barrier properties against corrosive gas. On the other hand, when the content of the ladder-type polyorganosilsesquioxane (C) is not more than 50% by weight, the resulting cured product tends to be improved in mechanical strength such as tenacity.

[Isocyanuric Skeleton-Containing Compound (D)]

The curable resin composition of the present invention may comprise an isocyanuric skeleton-containing compound (D). A cured product of the curable resin composition of the present invention comprising the isocyanuric skeleton-containing compound (D) tends to exhibit improved barrier properties against corrosive gas and further improved contact with an object. Combined use of the isocyanuric skeleton-containing compound (D) with the ladder-type polyorganosilsesquioxane (C) further enhances barrier properties against corrosive gas. Particularly, the isocyanuric skeleton-containing compound (D) is preferably a compound represented by the following formula (1):

[Formula 22]

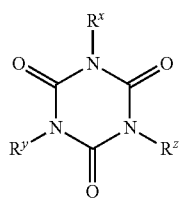

(1)

In the formula (1), $R^x$, $R^y$, and $R^z$ are the same or different and each represent a group represented by the formula (1a) or a group represented by the formula (1b). Among others, at least one of $R^x$, $R^y$, and $R^z$ is preferably a group represented by the formula (1b).

[Formula 23]

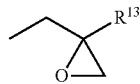

(1a)

[Formula 24]

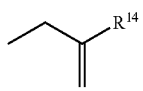
(1b)

In the formula (1a), $R^{13}$ represents a hydrogen atom or a linear or branched alkyl group having 1 to 8 carbon atoms (linear or branched $C_{1-8}$ alkyl group). Examples of the linear or branched $C_{1-8}$ alkyl group include a methyl group, an ethyl group, a propyl group, an isopropyl group, a butyl group, an isobutyl group, a s-butyl group, a pentyl group, a hexyl group, a heptyl group, an octyl group, and an ethylhexyl group. Among these alkyl groups, a linear or branched $C_{1-3}$ alkyl group such as a methyl group, an ethyl group, a propyl group, or an isopropyl group is preferred. Among others, $R^{13}$ is particularly preferably a hydrogen atom.

When two or three of $R^x$, $R^y$, and $R^z$ in the formula (1) are groups represented by the formula (1a), these groups represented by the formula (1a) may be the same or may be different. The compound represented by the formula (1) may not have a group represented by the formula (1a).

In the formula (1b), $R^{14}$ represents a hydrogen atom or a linear or branched alkyl group having 1 to 8 carbon atoms (linear or branched $C_{1-8}$ alkyl group). Examples of the linear or branched $C_{1-8}$ alkyl group include a methyl group, an ethyl group, a propyl group, an isopropyl group, a butyl group, an isobutyl group, a s-butyl group, a pentyl group, a hexyl group, a heptyl group, an octyl group, and an ethylhexyl group. Among these alkyl groups, a linear or branched $C_{1-3}$ alkyl group such as a methyl group, an ethyl group, a propyl group, or an isopropyl group is preferred. Among others, $R^{14}$ is particularly preferably a hydrogen atom.

When two or three of $R^x$, $R^y$, and $R^z$ in the formula (1) are groups represented by the formula (1b), these groups represented by the formula (1b) may be the same or may be different. The compound represented by the formula (1) may not have a group represented by the formula (1b).

Examples of the compound represented by the formula (1) include a compound represented by the formula (1) wherein one of $R^x$, $R^y$, and $R^z$ is a group represented by the formula (1b) (also referred to as a "monoallyl diglycidyl isocyanurate compound"), a compound represented by the formula (1) wherein two of $R^x$, $R^y$, and $R^z$ are represented by the formula (1b) (also referred to as a "diallyl monoglycidyl isocyanurate compound"), and a compound represented by the formula (1) wherein all of $R^x$, $R^y$, and $R^z$ are represented by the formula (1b) (also referred to as a "triallyl isocyanurate compound").

Specific examples of the monoallyl diglycidyl isocyanurate compound include monoallyl diglycidyl isocyanurate, 1-allyl-3,5-bis(2-methylepoxypropyl) isocyanurate, 1-(2-methylpropenyl)-3,5-diglycidyl isocyanurate, and 1-(2-methylpropenyl)-3,5-bis(2-methylepoxypropyl) isocyanurate.

Specific examples of the diallyl monoglycidyl isocyanurate compound include diallyl monoglycidyl isocyanurate, 1,3-diallyl-5-(2-methylepoxypropyl) isocyanurate, 1,3-bis(2-methylpropenyl)-5-glycidyl isocyanurate, and 1,3-bis(2-methylpropenyl)-5-(2-methylepoxypropyl) isocyanurate.

Specific examples of the triallyl isocyanurate compound include triallyl isocyanurate and tris(2-methylpropenyl) isocyanurate.

In the curable resin composition of the present invention, one of these isocyanuric skeleton-containing compounds (D) can be used alone, or not less than two thereof can be used in combination. The isocyanuric skeleton-containing compound (D) can be obtained as, for example, a commercially available product.

The compound represented by the formula (1) having a group represented by the formula (1a) may be used after being denatured, for example, through reaction with a compound that reacts with an epoxy group, such as an alcohol or an acid anhydride.

The compound represented by the formula (1) having a group represented by the formula (1b) may be used after being reacted with, for example, a compound having a hydrosilyl group (hydrosilylation reaction) in advance. For example, the monoallyl diglycidyl isocyanurate compound and the ladder-type silsesquioxane (C2) may be reacted in the presence of a hydrosilylation catalyst and used as a constituent of the curable resin composition of the present invention.

The isocyanuric skeleton-containing compound (D) may be mixed with a silane coupling agent (E) in advance and then mixed with other components, as mentioned later, from the viewpoint of improving compatibility with the other components.

When the curable resin composition of the present invention comprises the isocyanuric skeleton-containing compound (D), the content of the isocyanuric skeleton-containing compound (D) in the curable resin composition of the present invention is not particularly limited and is preferably 0.01 to 6% by weight, more preferably 0.05 to 4% by weight, further preferably 0.08 to 3% by weight, with respect to the curable resin composition (100% by weight). When the content of the isocyanuric skeleton-containing compound (D) is not less than 0.01% by weight, the resulting cured product tends to exhibit further improved barrier properties against corrosive gas and contact with an object. On the other hand, when the content of the isocyanuric skeleton-containing compound (D) is not more than 6% by weight, the curable resin composition tends to be prevented from depositing solids attributed to the isocyanuric skeleton-containing compound (D).

[Silane Coupling Agent (E)]

The curable resin composition of the present invention may comprise a silane coupling agent (E). Particularly, a cured product of the curable resin composition of the present invention comprising the silane coupling agent (E) tends to exhibit improved contact with an object. The silane coupling agent (E) further has favorable compatibility with the isocyanuric skeleton-containing compound (D) (particularly, a monoallyl diglycidyl isocyanurate compound), the ladder-type silsesquioxane (C2), and the like and therefore particularly achieves improvement in compatibility with other components such as the isocyanuric skeleton-containing compound (D). Specifically, in the case of using, for example, the isocyanuric skeleton-containing compound (D), a composition of the isocyanuric skeleton-containing compound (D) and the silane coupling agent (E) is formed in advance and then mixed with other components. This facilitates obtaining a homogeneous curable resin composition.

A silane coupling agent known in the art or routinely used can be used as the silane coupling agent (E). Examples thereof include, but are not particularly limited to: epoxy group-containing silane coupling agents such as 3-glycidoxypropyltrimethoxysilane, 2-(3,4-epoxycyclohexyl)ethyltrimethoxysilane, 3-glycidoxypropylmethyldiethoxysilane, and 3-glycidoxypropyltriethoxysilane; amino group-containing silane coupling agents such as N-2-(aminoethyl)-

3-aminopropylmethyldimethoxysilane, N-2-(aminoethyl)-3-aminopropyltrimethoxysilane, N-2-(aminoethyl)-3-aminopropyltriethoxysilane, 3-aminopropyltrimethoxysilane, 3-aminopropyltriethoxysilane, 3-triethoxysilyl-N-(1,3-dimethyl-butylidene)propylamine, N-phenyl-3-aminopropyltrimethoxysilane, hydrochloride of N-(vinylbenzyl)-2-aminoethyl-3-aminopropyltrimethoxysilane, and N-((3-aminoethyl)-γ-aminopropylmethyldiethoxysilane; and tetramethoxysilane, tetraethoxysilane, methyltriethoxysilane, dimethyldiethoxysilane, methyltriethoxysilane, vinyltriethoxysilane, vinyltrimethoxysilane, vinyltris(methoxyethoxysilane), phenyltrimethoxysilane, diphenyldimethoxysilane, vinyltriacetoxysilane, γ-(meth)acryloyloxypropyltriethoxysilane, γ-(meth)acryloyloxypropyltrimethoxysilane, γ-(meth)acryloyloxypropylmethyldimethoxysilane, γ-(meth)acryloyloxypropylmethyldiethoxysilane, mercaptopropylenetrimethoxysilane, mercaptopropylenetriethoxysilane, and alkoxy oligomers (e.g., trade names "KR-513", "X-41-1059A", "KR-516", "X-41-1085", "X-41-1818", "X-41-1810", "X-40-2651", "X-40-2665A", "KR-513", "KC-89S", "KR-500", "X-40-9225", "X-40-9246", "X-40-9250"; all manufactured by Shin-Etsu Chemical Co., Ltd.). Among them, an epoxy group-containing silane coupling agent (particularly, 3-glycidoxypropyltrimethoxysilane) can be preferably used.

In the curable resin composition of the present invention, one of these silane coupling agents (E) can be used alone, or not less than two thereof can be used in combination. Alternatively, a commercially available product can also be used as the silane coupling agent (E).

When the curable resin composition of the present invention comprises the silane coupling agent (E), the content of the silane coupling agent (E) in the curable resin composition of the present invention is not particularly limited and is preferably 0.01 to 15% by weight, more preferably 0.1 to 10% by weight, further preferably 0.2 to 5% by weight, particularly preferably 0.3 to 0.5% by weight, with respect to the curable resin composition (100% by weight). When the content of the silane coupling agent (E) is not less than 0.01% by weight, the resulting cured product tends to exhibit improved contact with an object. Furthermore, since the solubility of the isocyanuric skeleton-containing compound (D) in the curable resin composition can be improved, the resulting cured product may be further improved in barrier properties against corrosive gas. On the other hand, when the content of the silane coupling agent (E) is not more than 15% by weight, the resulting cured product tends to be improved in tenacity, heat resistance, and barrier properties against corrosive gas because curing reaction proceeds sufficiently.

[Hydrosilylation Catalyst]

The curable resin composition of the present invention may comprise a hydrosilylation catalyst. The curable resin composition of the present invention comprising the hydrosilylation catalyst tends to be able to more efficiently accelerate hydrosilylation reaction between the aliphatic carbon-carbon double bonds (particularly, alkenyl groups) and the hydrosilyl groups in the curable resin composition by heating.

Examples of the hydrosilylation catalyst include well-known catalysts for hydrosilylation reaction such as platinum catalysts, rhodium catalysts, and palladium catalysts and specifically include platinum catalysts such as fine platinum powders, platinum black, platinum-supported fine silica powders, platinum-supported active carbon, chloroplatinic acid, complexes of chloroplatinic acid with alcohol, aldehyde, ketone, or the like, olefin complexes of platinum, carbonyl complexes of platinum such as a platinum-carbonylvinylmethyl complex, platinum-vinylmethylsiloxane complexes such as a platinum-divinyltetramethyldisiloxane complex and a platinum-cyclovinylmethylsiloxane complex, platinum-phosphine complexes, and platinum-phosphite complexes, and palladium or rhodium catalysts containing a palladium atom or a rhodium atom instead of the platinum atom in these platinum catalysts. Among others, the hydrosilylation catalyst is preferably a platinum-vinylmethylsiloxane complex, a platinum-carbonylvinylmethyl complex, or a complex of chloroplatinic acid with alcohol or aldehyde because of a favorable reaction rate.

In the curable resin composition of the present invention, one of these hydrosilylation catalysts can be used alone, or not less than two thereof can be used in combination.

When the curable resin composition of the present invention comprises the hydrosilylation catalyst, the content of the hydrosilylation catalyst in the curable resin composition of the present invention is not particularly limited and is preferably $1\times10^{-8}$ to $1\times10^{-2}$ mol, more preferably $1.0\times10^{-6}$ to $1.0\times10^{-3}$ mol, with respect to 1 mol in total of aliphatic carbon-carbon double bonds (particularly, alkenyl groups) contained in the curable resin composition. When the content is not less than $1\times10^{-8}$ mol, a cured product tends to be able to be more efficiently formed. On the other hand, when the content is not more than $1\times10^{-2}$ mol, the resulting cured product tends to be able to have a better hue (less stained).

The content of the hydrosilylation catalyst in the curable resin composition of the present invention is not particularly limited and is preferably, for example, an amount that falls within the range of 0.01 to 1000 ppm, more preferably 0.1 to 500 ppm, of platinum, palladium, or rhodium in terms of weight unit in the hydrosilylation catalyst. When the content of the hydrosilylation catalyst is within such a range, a cured product can be more efficiently formed. Furthermore, the resulting cured product tends to be able to have a better hue.

The curable resin composition of the present invention may further comprise a component other than the components mentioned above (also referred to as an "additional component"). Examples of the additional component include, but are not particularly limited to, siloxane compounds other than the polysiloxanes (A) and (B) (e.g., cyclic siloxane compounds and low-molecular-weight linear or branched siloxane compounds), hydrosilylation reaction inhibitors, solvents, and various additives. Examples of the additives include fillers including inorganic fillers such as precipitated silica, wet silica, fumed silica, pyrogenic silica, titanium oxide, alumina, glass, quartz, aluminosilicic acid, iron oxide, zinc oxide, calcium carbonate, carbon black, silicon carbide, silicon nitride, and boron nitride, these inorganic fillers treated with an organic silicon compound such as organohalosilane, organoalkoxysilane, or organosilazane, fine powders of organic resins, such as silicone resins other than those mentioned above, epoxy resins, and fluorine resins, and conductive powders of metals such as silver and copper, solvents, stabilizers (antioxidants, ultraviolet absorbers, light stabilizers, heat stabilizers, etc.), flame retardants (phosphorus flame retardants, halogen flame retardants, inorganic flame retardants, etc.), flame retardant aids, reinforcing materials (other fillers, etc.), nucleating agents, coupling agents, lubricants, waxes, plasticizers, mold release agents, shock resistance improvers, hue improvers, fluidity improvers, colorants (dyes, pigments, etc.), dispersants, antifoaming agents, air-release agents, antimicrobial agents, antiseptics, viscosity adjusters, thickeners, and phosphors. One of these additional components can be used alone, or not less than two thereof can be used in combination. The content of the additional component can be appropriately selected without impairing the effects of the present invention.

In the curable resin composition of the present invention, (i) the combination of the polysiloxane (A) comprising the branched polyorganosiloxane (A1) and the polysiloxane (B) comprising the polyorganosiloxane (B1), and/or (ii) the combination of the polysiloxane (A) comprising the polyorganosiloxysilalkylene (A2) having a phenyl group bonded to a silicon atom and the polysiloxane (B) comprising the polyorganosiloxysilalkylene (B2) is particularly preferred in which the total content of the polysiloxane (A) and the polysiloxane (B) in the curable resin composition of the present invention (100% by weight) is 60 to 99% by weight (more preferably 70 to 96% by weight, further preferably 80 to 90% by weight), the content of the ladder-type polyorganosilsesquioxane (C) is 0.1 to 50% by weight (more preferably 0.5 to 40% by weight, further preferably 0.5 to 30% by weight), the content of the isocyanuric skeleton-containing compound (D) is 0.01 to 6% by weight (more preferably 0.05 to 4% by weight, further preferably 0.08 to 3% by weight), and the content of the silane coupling agent (E) is 0.01 to 15% by weight (more preferably 0.1 to 10% by weight, further preferably 0.2 to 5% by weight, particularly preferably 0.3 to 0.5% by weight).

In the present specification, the content of each component (e.g., the polysiloxane (A), the polysiloxane (B), the ladder-type polyorganosilsesquioxane (C), the isocyanuric skeleton-containing compound (D), and the silane coupling agent (E)) contained in the curable resin composition of the present invention can be appropriately selected from within the described range such that the sum of respective contents is not more than 100% by weight.

The ratio of an aryl group (particularly, a phenyl group) bonded to a silicon atom to the total amount (100% by mol) of monovalent substituted or unsubstituted hydrocarbon groups bonded to silicon atoms in all polysiloxanes (the polysiloxane (A), the polysiloxane (B), the ladder-type polyorganosilsesquioxane (C), etc.) contained in the curable resin composition of the present invention is not particularly limited and is preferably not less than 1% by mol (e.g., 1 to 90% by mol), more preferably not less than 5% by mol (e.g., 5 to 80% by mol), further preferably not less than 10% by mol (e.g., 10 to 70% by mol), particularly preferably not less than 30% by mol (e.g., 30 to 50% by mol). When the ratio of an aryl group is not less than 1% by mol (particularly, not less than 10% by mol), the resulting cured product tends to have better sulfidation resistance. The ratio of an aryl group (particularly, a phenyl group) can be calculated on the basis of $^1$H-NMR spectrum measurement results of each polysiloxane contained in the curable resin composition and the content of each polysiloxane.

The curable resin composition of the present invention is not particularly limited and can be prepared by stirring and mixing the components described above at room temperature. The curable resin composition of the present invention can be used as a one-component composition which directly employs components mixed in advance, or can be used as a multi-component (e.g., two-component) composition which is used, for example, by mixing not less than 2 separately stored components at a predetermined ratio before use.

The curable resin composition of the present invention may have any of solid and liquid states. The curable resin composition of the present invention is not particularly limited and is usually liquid at ordinary temperature (approximately 25° C.).

The viscosity of the curable resin composition of the present invention at 23° C. is not particularly limited and is preferably 300 to 20000 mPa·s, more preferably 500 to 10000 mPa·s, further preferably 1000 to 8000 mPa·s. When the viscosity is not less than 300 mPa·s, the resulting cured product tends to exhibit improved heat resistance. On the other hand, when the viscosity is not more than 20000 mPa·s, the resulting curable resin composition is easy to prepare and is improved in its productivity and handleability. Furthermore, air bubbles are less likely to remain in a cured product. Therefore, the cured product (particularly, a sealing member) tends to have further improved productivity and quality. The viscosity of the curable resin composition is measured in the same way as in the viscosity of the ladder-type polyorganosilsesquioxane (C) mentioned above.

<Cured Product>

The curable resin composition of the present invention is cured (particularly, cured through hydrosilylation reaction) to obtain a cured product (also referred to as the "cured product of the present invention"). Conditions for the curing (particularly, curing through hydrosilylation reaction) are not particularly limited and can be appropriately selected from conditions heretofore known in the art. For example, the temperature (curing temperature) is preferably 25 to 180° C. (more preferably 60 to 150° C.), and the time (curing time) is preferably 1 to 720 minutes, from the viewpoint of a reaction rate. The curing can be carried out by one stage or can be carried out by multiple stages. The cured product of the present invention not only has high heat resistance and transparency unique to polysiloxane materials, but particularly has low tack properties and resists adhesion of garbage.

<Sealing Agent>

The curable resin composition of the present invention can be preferably used as a composition for sealing semiconductor devices in semiconductor apparatuses (sealing agent) (also referred to as the "sealing agent of the present invention"). Specifically, the sealing agent of the present invention can be particularly preferably used for the purpose of sealing optical semiconductor devices (LED devices) in optical semiconductor apparatuses (i.e., as a sealing agent for optical semiconductors). A sealing member (cured product) obtained by curing the sealing agent of the present invention not only has high heat resistance and transparency unique to polysiloxane materials, but particularly has low tack properties and resists adhesion of garbage. Therefore, the sealing agent of the present invention can be preferably used, particularly, as a sealing agent or the like for high-brightness and short-wavelength optical semiconductor devices.

<Semiconductor Apparatus>

A semiconductor apparatus (also referred to as the "semiconductor apparatus of the present invention") is obtained by sealing a semiconductor device using the sealing agent of the present invention. Specifically, the semiconductor apparatus of the present invention is a semiconductor apparatus having at least a semiconductor device and a sealing member which seals the semiconductor device, wherein the sealing member is a cured product of the sealing agent of the present invention. The semiconductor apparatus of the present invention can be produced by a method known in the art or routinely used. The production method is not particularly limited and involves, for example, injecting the sealing agent of the present invention into a predetermined mold, and curing the sealing agent by heating under predetermined conditions. The curing temperature and the curing time are not particularly limited and can be set to within the same ranges as in the preparation of the cured product. The sealing agent of the present invention can effectively exert the advantageous effects mentioned above, particularly, when the semiconductor apparatus is an optical semiconductor apparatus, i.e., when the sealing agent of the present invention is used as a sealing agent for optical semiconductor devices in optical semiconductor apparatuses (sealing agent for optical semiconductors). Use of the sealing agent of the present invention as a sealing agent for optical semiconductors produces an optical semiconductor apparatus (also referred to as the "optical semiconductor apparatus of the present invention"). One example of the optical semiconductor apparatus of the present invention is shown in FIG. 1. In FIG. 1, reference numeral 100 denotes a reflector (resin composition for light reflection), reference numeral 101 denotes a metallic wire (electrode), reference numeral 102 denotes an optical semiconductor device, reference numeral 103 denotes a bonding wire, and reference numeral 104 denotes a cured product (sealing member).

Particularly, the curable resin composition of the present invention can be preferably used for purposes such as a sealing agent for forming a sealing member that covers an optical semiconductor device in a high-brightness and short-wavelength optical semiconductor apparatus, and a sealing agent for forming a sealing member that covers a semiconductor device in a highly heat-resistant and highly voltage-resistant semiconductor apparatus (power semiconductor, etc.), which have been difficult to cope with using conventional resin materials.

The curable resin composition of the present invention is not limited by the sealing agent purposes mentioned above (particularly, sealing agent purposes for optical semiconductor devices) and can also be preferably used for optics-related and semiconductor-related purposes, for example, functional coating agents, heat-resistant plastic lenses, transparent instruments, adhesives (heat-resistant transparent adhesives, etc.), electric insulating materials (insulating films, etc.), laminates, coatings, inks, paints, sealing agents, resists, composite materials, transparent base materials, transparent sheets, transparent films, optical devices, optical lenses, optical members, rapid phototyping, electronic papers, touch panels, solar cell substrates, optical waveguides, light guide plates, and holographic memories.

[Method for Producing Curable Resin Composition According to Present Invention]

The method for producing a curable resin composition according to the present invention (also simply referred to as the "production method of the present invention") is a method for producing a curable resin composition comprising polysiloxane (A) and polysiloxane (B), wherein the curable resin composition comprises at least one polysiloxane selected from the group consisting of polyorganosiloxane represented by the average unit formula (a-1) and polyorganosiloxysilalkylene represented by the average unit formula (a-2) as the polysiloxane (A), and at least one polysiloxane selected from the group consisting of polyorganosiloxane represented by the average unit formula (b-1) and polyorganosiloxysilalkylene represented by the average unit formula (b-2) as the polysiloxane (B), satisfies $(T+Q)/D>0.3$ and $M+D+T+Q=1$, and contains 0.9 to 5.0 mol of hydrosilyl groups with respect to 1 mol of aliphatic carbon-carbon double bonds present in the composition.

The production method of the present invention comprises the step of determining the composition of the curable resin composition of interest by forming a cured product of a composition (I) and determining separation strength and/or a total separation load of the cured product by the separation load evaluation given below, the composition (I) comprising polysiloxane (A) and polysiloxane (B), wherein the composition (I) comprises at least one polysiloxane selected from the group consisting of polyorganosiloxane represented by the average unit formula (a-1) and polyorganosiloxysilalkylene represented by the average unit formula (a-2) as the polysiloxane (A), and at least one polysiloxane selected from the group consisting of polyorganosiloxane represented by the average unit formula (b-1) and polyorganosiloxysilalkylene represented by the average unit formula (b-2) as the polysiloxane (B), satisfies $(T+Q)/D>0.3$ and $M+D+T+Q=1$, and contains 0.9 to 5.0 mol of hydrosilyl groups with respect to 1 mol of aliphatic carbon-carbon double bonds present in the composition. The following separation load evaluation is also referred to as "separation load evaluation (Y)":

separation load evaluation: an object and the cured product are contacted with each other by moving at least one of the object and the cured product from perpendicularly distant positions so as to attain a contact area of not less than 50 mm$^2$, pressed against each other under a load, and then separated in a perpendicular direction; change in stress on the contact face in this operation is recorded; a value determined by dividing a maximum stress value from when the object and the cured product start to be separated to when the object and the cured product are completely separated by the contact area between the object and the cured product is used as the separation strength; and a value determined by dividing an area surrounded by a stress curve from when the object and the cured product start to be separated to when the object and the cured product are completely separated and a baseline by the contact area is used as the total separation load.

Specifically, in the production method of the present invention, before production of the curable resin composition, a cured product of a composition (also referred to as a "composition (I)") is formed by curing the composition (I), and separation strength and/or a total separation load of the cured product is determined by the separation load evaluation (Y). The composition (I) comprises polysiloxane (A) and polysiloxane (B), wherein the composition (I) comprises at least one polysiloxane selected from the group consisting of polyorganosiloxane represented by the average unit formula (a-1) and polyorganosiloxysilalkylene represented by the average unit formula (a-2) as the polysiloxane (A), and at least one polysiloxane selected from the group consisting of polyorganosiloxane represented by the average unit formula (b-1) and polyorganosiloxysilalkylene represented by the average unit formula (b-2) as the polysiloxane (B), satisfies $(T+Q)/D>0.3$ and $M+D+T+Q=1$, and contains 0.9 to 5.0 mol of hydrosilyl groups with respect to 1 mol of aliphatic carbon-carbon double bonds present in the composition. Then, the composition of a curable resin composition capable of forming a cured product that has desired tack properties and adherence of garbage is determined from the obtained separation strength and/or total separation load. The curable resin composition having the desired composition is produced.

The production method of the present invention comprising the step described above can produce a curable resin composition after estimation of the tack properties of a cured product of the curable resin composition to be obtained by the production method of the present invention, and the adherence of garbage to the cured product. Therefore, a curable resin composition whose product has low tack properties and resists adhesion of garbage can be produced without actually producing the product using the cured product of the curable resin composition.

The separation load evaluation (Y) corresponds to the measurement method of the present invention mentioned later. The curing of the curable resin composition for forming the cured product to be subjected to the separation load evaluation (Y) is not particularly limited and is preferably performed under at least one curing condition selected from among conditions involving 25 to 180° C. and 1 to 720 minutes. The curing can be carried out by one stage or can be carried out by multiple stages. Preferred curing conditions are the same as the curing conditions in the separation load evaluation (X).

The object in the separation load evaluation (Y) is not particularly limited and is preferably made of SUS. The contact area between the object and the cured product contacted with each other is not less than 50 $mm^2$ as mentioned above, preferably 50 to 800 $mm^2$. The load for the pressing is not particularly limited and is preferably 100 N. The pressing time is preferably 2 minutes.

In the separation load evaluation (Y), the rate at which the object and the cured product are separated is not particularly limited and is preferably at least arbitrary one point selected from 5 to 500 mm/min. Among others, the separation load evaluation is conducted at at least arbitrary 10 points selected from 5 to 500 mm/min, and the largest values among values obtained by measurement at the 10 points are preferably adopted as the separation strength and the total separation load, respectively. However, adjacent 2 points differ in rate by not less than 5 mm/min. The 10 points are preferably 10 points of 5 mm/min, 10 mm/min, 20 mm/min, 30 mm/min, 50 mm/min, 70 mm/min, 100 mm/min, 150 mm/min, 300 mm/min, and 500 mm/min.

More preferred evaluation conditions in the separation load evaluation (Y) are the same as the evaluation conditions in the separation load evaluation (X).

The curable resin composition before the separation load evaluation (Y) is produced in the same way as in the curable resin composition of the present invention.

[Method for Measuring Surface Tackiness of Viscoelastic Material According to Present Invention]

The method for measuring the surface tackiness of a viscoelastic material according to the present invention comprises: step A of contacting an object and the viscoelastic material with each other so as to attain a contact area of not less than 50 $mm^2$, applying a load thereto, and subsequently relaxing the stress (hereinafter, also simply referred to as "step A"); step B of separating the object and the viscoelastic material by the application of displacement in the direction of separation (hereinafter, also simply referred to as "step B"); and step C of recording change in stress on the contact face from the contact to the separation, obtaining a curve of displacement on the x-axis and stress on the y-axis, and quantifying tackiness from the obtained curve (hereinafter, also simply referred to as "step C"). In the present specification, the "method for measuring the surface tackiness of a viscoelastic material according to the present invention" is also referred to as the "measurement method of the present invention". The measurement method of the present invention is capable of quantitatively measuring, with high measurement accuracy, tack properties as to even viscoelastic materials having low tack properties, such as silicone sealing members. Therefore, the relative comparison of tack properties is easily conducted as to even viscoelastic materials having low tack properties. Thus, the relative comparison of tack properties is easily conducted consistently from a low-tack region to a high-tack region.

(Step A)

The measurement method of the present invention is a method for evaluating the tack properties of a viscoelastic material. The step A involves a unit of contacting an object and the viscoelastic material with each other so as to attain a contact area of not less than 50 $mm^2$, and applying a load thereto, and a unit of relaxing the stress. In the step A, the direction in which the object and the viscoelastic material are contacted with each other, and the direction in which a load is applied are preferably a perpendicular direction (vertical direction). The load may be applied from the object side or may be applied from the viscoelastic material side. Specifically, at least one of the object and the viscoelastic material is moved in the direction of contact, and in this case, any of them may be moved. When the direction of contact and the direction of load application are a vertical direction, the direction of contact may be vertically upward or may be vertically downward. The direction of movement for the contact in the step A is opposite to the direction of movement for the separation in the step B.

In the unit of relaxing the stress, the stress generated by the application of the load to the viscoelastic material after the contact between the object and the viscoelastic material is relaxed by keeping the load-applied state for a given time.

In the step A, the unit of contacting an object and the viscoelastic material with each other, and applying a load thereto preferably employs a stress detection mechanism having a mount and the object. In this case, the unit preferably places a flat-shaped viscoelastic material onto the mount, and continuously applies a load by pressing the object against the viscoelastic material such that the contact face between the viscoelastic material and the object is a plane.

In the step A, a value (pressure) determined by dividing the load applied after the contact of the object and the viscoelastic material by the contact area is not particularly limited and is preferably 0.1 to 4 MPa, more preferably 0.1 to 2 MPa, further preferably 0.2 to 2 MPa. The pressure that falls within the range described above tends to become pressurization force appropriate for the measurement of tack properties.

The time for which the load-applied state (pressurized state) is kept (pressurization time) is not particularly limited and is preferably 0.5 to 10 minutes, more preferably 1 to 3 minutes. The pressurization time that falls within the range described above can sufficiently secure a time for promoting stress relaxation after the contact between the viscoelastic material surface and the object surface and tends to decrease the influence of elastic force on the measurement of tack properties.

The viscoelastic material is not particularly limited by its shape and is preferably flat-shaped. The thickness of the viscoelastic material is not particularly limited and is preferably 0.5 to 5 mm, more preferably 1 to 3 mm.

The shape of the object is not particularly limited, and the face of the object contacted with the viscoelastic material is preferably a plane. In this case, the plane area of the object is preferably larger than the area of the contact portion between the viscoelastic material and the object. Specifically, the area of the face of the object contacted with the viscoelastic material is preferably larger than the contact area. Such an example is the case where, for example, reference numeral 300 shown in FIG. 3 is the viscoelastic material, and reference numeral 303 is the object. In the probe tack test, the area of the face of the object (probe) contacted with the viscoelastic material is smaller than the contact area between the viscoelastic material and the object. Therefore, the viscoelastic material is deformed due to stress localized to the contact face in the peripheral edge of apical surface of the probe. Furthermore, this causes variations in measurement results and reduces the quantitative performance and quality of the measurement results. By contrast, in the measurement method of the present invention, the plane area of the object can be larger than the area of the contact portion between the viscoelastic material and the object to thereby minimize the influence of the edge portion in the probe tack test.

The contact area between the viscoelastic material and the object is not less than 50 mm$^2$ as mentioned above, preferably 50 to 800 mm$^2$, more preferably 100 to 400 mm$^2$. When the contact area is not less than 50 mm$^2$, the measurement area of the viscoelastic material is a wide range in the measurement method of the present invention in contrast to a narrow and local measurement area in the conventional probe tack test. Therefore, the number of detection values in a low-tack region is increased, and an average measurement value of a wide range is obtained. As in the case where, for example, reference numeral 300 shown in FIG. 3 is the viscoelastic material and reference numeral 303 is the object, the area of the face of the flat-shaped viscoelastic material contacted with the object is preferably the same as the contact area described above.

A material for the object is not particularly limited, and a material for use in objects in the evaluation of tack properties known in the art or routinely used can be used. Among others, SUS is preferred.

(Step B)

In the step B, the object and the viscoelastic material are separated by the application of displacement in the direction of separation. The subject to which the displacement is applied may be any of the viscoelastic material and the object and is the same as the subject to which displacement is applied for contact and load application in the step A. The direction of separation is preferably a perpendicular direction (vertical direction).

In the step B, the rate at which the object and the viscoelastic material are separated is not particularly limited and is preferably 1 to 1000 mm/min, more preferably 5 to 30 mm/min. Particularly, the rate of the separation is preferably any of 10 points of 5 mm/min, 10 mm/min, 20 mm/min, 30 mm/min, 50 mm/min, 70 mm/min, 100 mm/min, 150 mm/min, 300 mm/min, and 500 mm/min, more preferably all of the 10 points (i.e., measurement at all of the 10 rates).

(Step C)

In the step C, change in stress on the contact face from the contact in the step A to the separation in the step B is recorded, and a curve of displacement (distance between the object and the viscoelastic material) on the x-axis and stress on the y-axis is obtained. Then, tackiness is quantified from the obtained curve. FIG. 2 shows one example of the curve of displacement on the x-axis and stress on the y-axis.

In the step C, a maximum stress value in the curve can be obtained as the tackiness value of the viscoelastic material. The maximum stress value is the difference between stress 0 at which compression turns to pulling and the largest value of stress (e.g., a value represented by 200 in FIG. 2) in the curve.

An area that is surrounded by the curve and a baseline (axis at which the stress is 0) and is on a side including the maximum stress value in the curve (e.g., the area of a region indicated by 201 in FIG. 2) can also be obtained as the tackiness value of the viscoelastic material. The area can be calculated as an integral value of a function with the curve as the function.

When the rate of the separation is set to all of 10 points of 5 mm/min, 10 mm/min, 20 mm/min, 30 mm/min, 50 mm/min, 70 mm/min, 100 mm/min, 150 mm/min, 300 mm/min, and 500 mm/min, the largest value among values obtained at the 10 points is particularly preferably obtained as the tackiness value. Specifically, preferably, the curve is obtained as to each of the 10 separation rates, and the largest value among maximum stress values in the obtained 10 curves is obtained as the tackiness value, or the largest value in areas on sides including the maximum stress values in the obtained 10 curves is obtained as the tackiness value.

The maximum stress value and the area serve as indexes for obtaining different tack properties. Therefore, both of the tack properties are preferably taken into consideration according to object of evaluation.

The measurement method of the present invention is not particularly limited and is preferably carried out in an environment involving a temperature of 10 to 30° C. and a humidity of 30 to 70% RH (preferably a temperature of 15 to 25° C. and a humidity of 40 to 60% RH).

The measurement method of the present invention can be performed using a commercially available universal tester. Each of the separation load evaluation (X) and the separation load evaluation (Y) is one example of an evaluation method adopting the measurement method of the present invention. Thus, FIG. 3 is also a schematic diagram showing specific one example of the measurement method of the present invention. More preferred evaluation conditions in the measurement method of the present invention can be appropriately adopted in consideration of each evaluation condition in the separation load evaluation (X) or the separation load evaluation (Y).

EXAMPLES

Hereinafter, the present invention will be described in more detail with reference to Examples. However, the present invention is not intended to be limited by these Examples.

The $^1$H-NMR analysis of products and merchandise was conducted with JEOL ECA500 (500 MHz). The $^{29}$Si-NMR analysis of products and merchandise was conducted with JEOL ECA500 (500 MHz). The number-average molecular weights and weight-average molecular weights of products and merchandise were measured using Alliance HPLC system 2695 (manufactured by Waters Corp.) and Refractive Index Detector 2414 (manufactured by Waters Corp.); column: Tskgel GMH$_{HR}$-M×2 (manufactured by Tosoh Corp.), guard column: Tskgel guard column H$_{HR}$L (manufactured by Tosoh Corp.), column oven: COLUMN HEATER U-620 (manufactured by Sugai Chemical Ind. Co., Ltd.), solvent: THF, and measurement conditions: 40° C.

Production Example 1

[Synthesis of Ladder-Type Polyorganosilsesquioxane Having Terminal Vinyl and Trimethylsilyl (TMS) Groups]

A 200-ml four-neck flask was charged with 42.61 g of methyltriethoxysilane (manufactured by Shin-Etsu Chemical Co., Ltd.), 6.76 g of phenyltriethoxysilane (manufactured by Shin-Etsu Chemical Co., Ltd.), and 17.69 g of methyl isobutyl ketone (MIBK), and the mixture was cooled to 10° C. To the mixture, 240 mmol (4.33 g) of water and 0.48 g (2.4 mmol as hydrogen chloride) of 5 N hydrochloric acid were added dropwise at the same time over 1 hour. After the dropwise addition, the mixture was kept at 10° C. for 1 hour. Then, the reaction solution was diluted by the addition of 80.0 g of MIBK.

Next, the temperature of the reaction container was raised to 70° C. At the point in time when the temperature reached 70° C., 606 mmol (10.91 g) of water was added thereto, and polycondensation reaction was performed at the same temperature as above for 9 hours in a nitrogen atmosphere. 2.08 g of vinyltriethoxysilane was further added thereto, and aging reaction was performed at the same temperature as above for 3 hours.

Subsequently, 15.0 g of hexamethyldisiloxane was added to the obtained reaction solution, and silylation reaction was performed at 70° C. for 3 hours. Then, the reaction solution was cooled and washed with water until the lower layer liquid became neutral, followed by the separation of the upper layer liquid. Next, the solvent was distilled off from the upper layer liquid under conditions of 1 mmHg and 60° C. to obtain 19.0 g of ladder-type polyorganosilsesquioxane having terminal vinyl and TMS groups as a clear colorless liquid product. The ladder-type polyorganosilsesquioxane obtained in Production Example 1 corresponds to the ladder-type silsesquioxane (C1) mentioned above.

The ladder-type polyorganosilsesquioxane having terminal vinyl and TMS groups had a weight-average molecular weight (Mw) of 2700, a phenyl group content (average content) of 4% by mol per molecule, and a vinyl group content (average content) of 2% by mol per molecule.

($^1$H-NMR spectrum of ladder-type polyorganosilsesquioxane having terminal vinyl and TMS groups)

$^1$H-NMR (JEOL ECA500 (500 MHz, CDCl$_3$)): δ-0.3-0.3 ppm (br), 5.7-6.2 ppm (br), 7.1-7.7 ppm (br)

Production Example 2

[Synthesis of Ladder-Type Polyorganosilsesquioxane Having Terminal Vinyl and TMS Groups]

A 200-ml four-neck flask was charged with 34.07 g of methyltriethoxysilane (manufactured by Shin-Etsu Chemical Co., Ltd.), 11.49 g of phenyltriethoxysilane (manufactured by Shin-Etsu Chemical Co., Ltd.), and 17.69 g of methyl isobutyl ketone (MIBK), and the mixture was cooled to 10° C. To the mixture, 240 mmol (4.33 g) of water and 0.48 g (2.4 mmol as hydrogen chloride) of 5 N hydrochloric acid were added dropwise at the same time over 1 hour. After the dropwise addition, the mixture was kept at 10° C. for 1 hour. Then, the reaction solution was diluted by the addition of 80.0 g of MIBK.

Next, the temperature of the reaction container was raised to 70° C. At the point in time when the temperature reached 70° C., 606 mmol (10.91 g) of water was added thereto, and polycondensation reaction was performed at the same temperature as above for 9 hours in a nitrogen atmosphere. 6.25 g of vinyltriethoxysilane was further added thereto, and aging reaction was performed at the same temperature as above for 3 hours.

Subsequently, 15.0 g of hexamethyldisiloxane was added to the obtained reaction solution, and silylation reaction was performed at 70° C. for 3 hours. Then, the reaction solution was cooled and washed with water until the lower layer liquid became neutral, followed by the separation of the upper layer liquid. Next, the solvent was distilled off from the upper layer liquid under conditions of 1 mmHg and 60° C. to obtain 36.8 g of ladder-type polyorganosilsesquioxane having terminal vinyl and TMS groups as a clear colorless liquid product. The ladder-type polyorganosilsesquioxane obtained in Production Example 2 corresponds to the ladder-type silsesquioxane (C1) mentioned above.

The ladder-type polyorganosilsesquioxane having terminal vinyl and TMS groups had a weight-average molecular weight (Mw) of 3400, a phenyl group content (average content) of 8% by mol per molecule, and a vinyl group content (average content) of 6% by mol per molecule.

($^1$H-NMR spectrum of ladder-type polyorganosilsesquioxane having terminal vinyl and TMS groups)

$^1$H-NMR (JEOL ECA500 (500 MHz, CDCl$_3$)): δ-0.3-0.3 ppm (br), 5.7-6.2 ppm (br), 7.1-7.7 ppm (br)

Production Example 3

[Synthesis of Ladder-Type Polyorganosilsesquioxane Having Terminal TMS Group]

A 200-ml four-neck flask was charged with 30.06 g of methyltriethoxysilane (manufactured by Shin-Etsu Chemical Co., Ltd.), 21.39 g of vinyltriethoxysilane (manufactured by Tokyo Chemical Industry Co., ltd.), and 17.69 g of methyl isobutyl ketone (MIBK), and the mixture was cooled to 10° C. To the mixture, 281 mmol (5.06 g) of water and 0.48 g (2.4 mmol as hydrogen chloride) of 5 N hydrochloric acid were added dropwise at the same time over 1 hour. After the dropwise addition, the mixture was kept at 10° C. for 1 hour. Then, the reaction solution was diluted by the addition of 80.0 g of MIBK.

Next, the temperature of the reaction container was raised to 70° C. At the point in time when the temperature reached 70° C., 703 mmol (12.64 g) of water was added thereto, and polycondensation reaction was performed at the same temperature as above for 12 hours in a nitrogen atmosphere.

Subsequently, 15.0 g of hexamethyldisiloxane was added to the obtained reaction solution, and silylation reaction was performed at 70° C. for 3 hours. Then, the reaction solution was cooled and washed with water until the lower layer liquid became neutral, followed by the separation of the upper layer liquid. Next, the solvent was distilled off from the upper layer liquid under conditions of 1 mmHg and 60° C. to obtain 22.0 g of ladder-type polyorganosilsesquioxane having a terminal TMS group as a clear colorless solid product. The ladder-type polyorganosilsesquioxane obtained in Production Example 3 corresponds to the ladder-type silsesquioxane (C1) mentioned above.

The ladder-type polyorganosilsesquioxane having a terminal TMS group had a weight-average molecular weight (Mw) of 5000, a vinyl group content (average content) of 16% by mol per molecule, and a phenyl group content (average content) of 0% by mol (not observed) per molecule.

($^1$H-NMR spectrum of ladder-type polyorganosilsesquioxane having terminal TMS group)

(JEOL ECA500 (500 MHz, CDCl$_3$)): δ 0-0.3 ppm (br), 5.8-6.1 ppm (br)

Production Example 4

[Synthesis of Ladder-Type Polyorganosilsesquioxane Having Terminal Vinyl Group]

A 200-ml four-neck flask was charged with 15.86 g of phenyltriethoxysilane (manufactured by Shin-Etsu Chemical Co., Ltd.) and 6.16 g of methyl isobutyl ketone (MIBK), and the mixture was cooled to 10° C. To the mixture, 4.32 g of water and 0.16 g (2.4 mmol as hydrogen chloride) of 5 N hydrochloric acid were added dropwise over 1 hour. After the dropwise addition, the mixture was kept at 10° C. for 1 hour. Then, the reaction solution was diluted by the addition of 26.67 g of MIBK.

Next, the temperature of the reaction container was raised to 70° C. At the point in time when the temperature reached 70° C., 0.16 g (25 mmol as hydrogen chloride) of 5 N hydrochloric acid was added thereto, and polycondensation reaction was performed for 4 hours in a nitrogen atmosphere.

Subsequently, 11.18 g of divinyltetramethyldisiloxane and 3.25 g of hexamethyldisiloxane were added to the obtained reaction solution, and silylation reaction was performed at 70° C. for 4 hours. Then, the reaction solution was cooled and washed with water until the lower layer liquid became neutral, followed by the separation of the upper layer liquid. Next, the solvent was distilled off from the upper layer liquid under conditions of 1 mmHg and 40° C. to obtain a clear colorless liquid reaction product (ladder-type silsesquioxane having a terminal vinyl group, 13.0 g). The ladder-type polyorganosilsesquioxane obtained in Production Example 4 corresponds to the ladder-type silsesquioxane (C1) mentioned above.

The ladder-type polyorganosilsesquioxane having a terminal vinyl group had a number-average molecular weight (Mn) of 840 and a molecular weight distribution of 1.06.

Each component described in Table 1 will be described below.

(Agent A)

AS-9070A: manufactured by Eternal Materials Co., Ltd., trade name "AS-9070A" (comprising polyorganosiloxane represented by the average unit formula (a-1)), vinyl group content with respect to the total amount (100% by weight) of the product: 1.20% by weight, phenyl group content: 0% by weight, hydrosilyl group content (based on hydride): 0% by weight, number-average molecular weight: 2517, weight-average molecular weight: 14505, comprising a hydrosilylation catalyst.

GS5145A: manufactured by Eternal Materials Co., Ltd., trade name "ETERLED GS5145A" (comprising polyorganosiloxysilalkylene represented by the average unit formula (a-2)), proportion of an aryl group (phenyl group): approximately 24% by mol, comprising a hydrosilylation catalyst.

KER-2500A: manufactured by Shin-Etsu Chemical Co., Ltd., trade name "KER-2500A" (comprising polyorganosiloxane represented by the average unit formula (a-1)), vinyl group content with respect to the total amount (100% by weight) of the product: 1.53% by weight, methyl group content: 94.29% by weight, phenyl group content: 0% by weight, hydrosilyl group content (based on hydride): 0.03% by weight, number-average molecular weight: 4453, weight-average molecular weight: 19355, comprising a hydrosilylation catalyst.

OE-6351A: manufactured by Dow Corning Toray Co., Ltd., trade name "OE-6351A" (comprising polyorganosiloxane represented by the average unit formula (a-1)), vinyl group content: 0.67% by weight, phenyl group content: 0% by weight, hydrosilyl group content (based on hydride): 0% by weight, number-average molecular weight: 4900, weight-average molecular weight: 20900, comprising a hydrosilylation catalyst.

OE-6630A: manufactured by Dow Corning Toray Co., Ltd., trade name "OE-6630A" (comprising polyorganosiloxane represented by the average unit formula (a-1)), vinyl group content: 2.17% by weight, phenyl group content: 51.94% by weight, hydrosilyl group content (based on hydride): 0% by weight, number-average molecular weight: 2532, weight-average molecular weight: 4490, comprising a hydrosilylation catalyst.

DMS-V35: manufactured by Gelest, Inc., trade name "DMS-V35", polydimethylsiloxane having vinyl groups at both ends MA-DGIC: manufactured by Shikoku Chemicals Corp., trade name "MA-DGIC", monoallyl diglycidyl isocyanurate OFS-6040: manufactured by Dow Corning Toray Co., Ltd., trade name "XIAMETER OFS-6040", 3-glycidoxy-propyltrimethoxysilane (Agent B)

AS-9070B: manufactured by Eternal Materials Co., Ltd., trade name "AS-9070B" (comprising polyorganosiloxane represented by the average unit formula (b-1)), vinyl group content with respect to the total amount (100% by weight) of the product: 1.15% by weight, phenyl group content: 0% by weight, hydrosilyl group content (based on hydride): 0.150% by weight, number-average molecular weight: 2371, weight-average molecular weight: 14526

GS5145B: trade name "ETERLED GS5145B" (comprising polyorganosiloxysilalkylene represented by the average unit formula (b-2)), manufactured by Eternal Materials Co., Ltd.

KER-2500B: manufactured by Shin-Etsu Chemical Co., Ltd., trade name "KER-2500B" (comprising polyorganosiloxane represented by the average unit formula (b-1)), vinyl group content with respect to the total amount (100% by weight) of the product: 1.08% by weight, methyl group content: 95.63% by weight, phenyl group content: 0% by weight, hydrosilyl group content (based on hydride): 0.13% by weight, number-average molecular weight: 4636, weight-average molecular weight: 18814

OE-6351B: manufactured by Dow Corning Toray Co., Ltd., trade name "OE-6351B" (comprising polyorganosiloxane represented by the average unit formula (b-1)), vinyl group content: 0.71% by weight, phenyl group content: 0% by weight, hydrosilyl group content (based on hydride): 0.08% by weight, number-average molecular weight: 6100, weight-average molecular weight: 20900

OE-6630B: manufactured by Dow Corning Toray Co., Ltd., trade name "OE-6630B" (comprising polyorganosiloxane represented by the average unit formula (b-1)), vinyl group content: 3.87% by weight, phenyl group content: 50.11% by weight, hydrosilyl group content (based on hydride): 0.17% by weight, number-average molecular weight: 783, weight-average molecular weight: 133

HMS-991: manufactured by Gelest, Inc., trade name "HMS-991", polymethylhydrosiloxane having TMS groups at both ends Example 1

[Production of Curable Resin Composition]

First, as shown in Table 1, AS-9070A (50 parts by weight), the ladder-type polyorganosilsesquioxane obtained in Production Example 3 (15 parts by weight), MA-DGIC (0.2 part by weight), and OFS-6040 (0.4 part by weight) were mixed and stirred at 80° C. for 1 hour to prepare agent A.

Next, the agent A thus obtained (65.6 parts by weight) was mixed with AS-9070B (45 parts by weight) and HMS-991 (5 parts by weight) as agent B, and stirred at room temperature for 10 minutes to obtain a curable resin composition as a homogeneous liquid.

[Production of Optical Semiconductor Apparatus]

The curable resin composition thus obtained was injected to a LED package having the form shown in FIG. 1 (InGaN device, 5.0 mm×5.0 mm), and heated at 100° C. for 1 hour and subsequently at 150° C. for 5 hours to produce an optical semiconductor apparatus in which the optical semiconductor device was sealed with a cured product of the curable resin composition.

Examples 2 to 7 and Comparative Examples 1 to 5

Each curable resin composition and each optical semiconductor apparatus were produced in the same way as in Example 1 except that the formulation of the curable resin composition was changed as shown in Table 1.
(Evaluation)
Each curable resin composition and each optical semiconductor apparatus thus obtained were subjected to the evaluation given below. The evaluation results are shown in Table 1.
[$^{29}$Si-NMR Spectrum Measurement and $^1$H-NMR Spectrum Measurement]
M, D, T, and Q were calculated by $^{29}$Si-NMR spectrum measurement as to the curable resin composition obtained in each of Examples and Comparative Examples, and (T+Q)/D was further calculated using the obtained values. The molar number of hydrosilyl groups with respect to 1 mol of aliphatic carbon-carbon double bonds was calculated by $^1$H-NMR spectrum measurement. The ratio of an aryl group to the total amount of monovalent substituted or unsubstituted hydrocarbon groups bonded to silicon atoms in all polysiloxanes in the curable resin composition was calculated from $^1$H-NMR spectrum measurement and the content of each polysiloxane used. In the $^1$H-NMR spectrum measurement, the presence of an aryl group other than a phenyl group was unable to be confirmed. The results are shown in Table 1.
[Separation Strength and Total Separation Load]
The curable resin composition obtained in each of Examples and Comparative Examples was injected to a square mold having a thickness of 3 mm, a width of 80 mm, and a length of 80 mm and heated at 100° C. for 1 hour and subsequently at 150° C. for 5 hours to produce a cured product (thickness: 3 mm) of the curable resin composition. This cured product was cut out using a round cutter of 16 mm in diameter and used as a test specimen for the measurement of separation strength and a total separation load.
The separation strength was evaluated using a universal tester (trade name "TENSILON universal material tester RTC-1310A", manufactured by A&D Co., Ltd.). The evaluation method will be described with reference to FIG. 3. Test specimen 300 for measurement was fixed onto crosshead 306 with double-faced adhesive tape 304, and object 303 (SUS plate having smooth surface) was further attached to load cell 302.
Next, the crosshead 306 was slowly moved upward (in a direction indicated by D) in a perpendicular direction so that the test specimen 300 for measurement was press against the object 303 under conditions involving a pressing load of 100 N and a pressing time of 2 minutes. Then, the test specimen and the object were separated by moving the crosshead 306 downward (in a direction opposite to the direction indicated by D) in a perpendicular direction at a separation rate of 5 mm/min to separate the test specimen 300 for measurement from the object 303. The stress generated in this operation was detected with the load cell 302 and recorded on a chart using a recorder to obtain a stress curve of separation strength (stress) (N) on the ordinate and displacement (mm) on the abscissa. Then, a value determined by dividing the largest stress value among the obtained measurement values by the contact area between the test specimen 300 for measurement and the object 303 (i.e., 201 mm$^2$) was used as the separation strength at the separation rate. A value determined by dividing an area surrounded by the stress curve from when the test specimen and the object started to be separated to when the test specimen and the object were completely separated and the baseline by the contact area between the test specimen 300 for measurement and the object 303 (i.e., 201 mm$^2$) was used as the total separation load at the separation rate.

Further, separation strength and a total separation load were obtained in the same way as above when the separation rate was set to 10 mm/min, 20 mm/min, 30 mm/min, 50 mm/min, 70 mm/min, 100 mm/min, 150 mm/min, 300 mm/min, and 500 mm/min. Then, the respective largest values of the obtained separation strength and total separation loads were used as the separation strength and total separation load values, respectively, of the cured product of the curable resin composition. The results are shown in Table 1. In Table 1, the unit of the separation strength is [N], and the unit of the total separation load is [N·mm].
[Adhesion Test]
The optical semiconductor apparatus produced in each of Examples and Comparative Examples was used as a sample.
The cured product surface in the optical semiconductor apparatus was rubbed in contact with a SUS plate (made of SUS304; thickness: 1 mm, mirrored surface) washed with acetone in advance. Then, the sample was perpendicularly lifted by holding the SUS plate with the SUS plate positioned on the downside and turned upside down to confirm whether the optical semiconductor apparatus was spontaneously separated therefrom by gravity within 10 seconds. Then, the sample was evaluated as lacking tack properties when separated within 10 seconds, and as having tack properties when adhering for more than 10 seconds. The results are shown in Table 1.
[Garbage Adhesion Test]
The curable resin composition obtained in each of Examples and Comparative Examples was injected to a rectangular mold having a thickness of 3 mm, a width of 10 mm, and a length of 50 mm and heated at 100° C. for 1 hour and subsequently at 150° C. for 5 hours to produce a cured product (thickness: 3 mm) of the curable resin composition. This cured product was used as a test specimen for the garbage adhesion test.
The test specimen was attached to a pedestal (height: 1 m, slope: 45°) placed on the grounds of Daicel Corp. (Otake city, Hiroshima, Japan) and subjected to an exposure test for 2 weeks. The ease of adhesion of garbage was evaluated according to criteria given below. The results are shown in Table 1.

⊙: The adhesion of garbage was rarely observed.
○: The adhesion of garbage was slightly observed, but the garbage was easily removable by washing with running water.
x: A considerable amount of garbage adhered and was unable to be removed by washing with running water.

[Sulfur Corrosiveness Test (Sulfidation Resistance)]
The optical semiconductor apparatus produced in each of Examples and Comparative Examples was used as a sample.
First, the total luminous flux (unit: 1 m) of the sample under a current of 20 mA was measured using a total luminous flux measurement apparatus (manufactured by Optronic Laboratories, Inc., Multi-channel Spectroradiometric Measurement System "OL771") and used as a "total luminous flux before the corrosiveness test".
Next, the sample and 0.3 g of sulfur powders (manufactured by Kishida Chemical Co., Ltd.) were placed in a 450-ml glass bottle. The glass bottle was further placed in an aluminum box. Subsequently, the aluminum box was placed in an oven (manufactured by Yamato Scientific Co., Ltd., model: DN-64) of 80° C. and taken out after 8 hours. The total luminous flux of the sample thus heated was measured in the same way as above and used as a "total luminous flux after the corrosiveness test". Then, the maintenance ratio of the total luminous flux between before and after the corrosiveness test (%) [=100×(Total luminous flux after the corrosiveness test (lm))/(Total luminous flux before the corrosiveness test (lm))] was calculated.

A higher light intensity maintenance ratio means that the cured product (sealing member) has better barrier properties against corrosive gas. The light intensity maintenance ratios of 10 optical semiconductor apparatuses were measured and calculated per curable resin composition (per Example or Comparative Example), and an average value of these light intensity maintenance ratios (N=10) is shown in Table 1.

TABLE 1

| | | | Example 1 | Example 2 | Example 3 | Example 4 | Example 5 | Example 6 | Example 7 | Comparative Example 1 | Comparative Example 2 | Comparative Example 3 | Comparative Example 4 | Comparative Example 5 |
|---|---|---|---|---|---|---|---|---|---|---|---|---|---|---|
| Curable resin composition | Agent A | Mixture of polysiloxane (A) and platinum catalyst | AS-9070A | part by weight | 25 | 25 | 40 | 35 | — | — | — | 15 | 45 | — | — | — |
| | | | GS5145A | part by weight | — | — | — | — | 19 | 18 | — | — | — | — | — | 20 |
| | | | KER-2500A | part by weight | — | — | — | — | — | — | 50 | — | — | — | — | — |
| | | | OE-6351A | part by weight | — | — | — | — | — | — | — | — | — | 50 | — | — |
| | | | OE-6630A | part by weight | — | — | — | — | — | — | — | — | — | — | 20 | — |
| | | Polysiloxane (A) | DMS-V35 | part by weight | 15 | 15 | — | 10 | — | — | — | 55 | — | — | — | — |
| | | Ladder-type polyorganosilsesquioxane (C) | Production Example 1 | part by weight | — | 10 | 15 | 15 | — | — | — | 15 | — | — | — | 3 |
| | | | Production Example 2 | part by weight | 10 | — | — | — | — | — | — | — | 20 | — | — | — |
| | | | Production Example 3 | part by weight | — | — | — | — | — | 1 | — | — | — | — | — | 2 |
| | | | Production Example 4 | part by weight | — | — | — | — | 1 | 1 | — | — | — | — | — | — |
| | | Isocyanuric skeleton-containing compound (D) | MA-DGIC | part by weight | 0.2 | 0.2 | 0.2 | 0.2 | 0.2 | 0.2 | — | 0.2 | 0.2 | — | — | 0.2 |
| | | Silane coupling agent (E) | OFS-6040 | part by weight | 0.4 | 0.4 | 0.4 | 0.4 | 0.4 | 0.4 | — | 0.4 | 0.4 | — | — | 0.4 |
| | Agent B | Mixture of polysiloxane (A) and polysiloxane (B) | AS-9070B | part by weight | 47 | 47 | 44 | 39 | — | — | — | 14 | 35 | — | — | — |
| | | | GS5145B | part by weight | — | — | — | — | 80 | 80 | — | — | — | — | — | 75 |
| | | | KER-2500B | part by weight | — | — | — | — | — | — | 50 | — | — | — | — | — |
| | | | OE-6351B | part by weight | — | — | — | — | — | — | — | — | — | 50 | — | — |
| | | | OE-6630B | part by weight | — | — | — | — | — | — | — | — | — | — | 80 | — |
| | | Polysiloxane (B) | HMS-991 | part by weight | 3 | 3 | 1 | 1 | — | — | — | 1 | — | — | — | — |
| | Phenyl group content (% by mol) | | | | 0 | 0.8 | 0.6 | 0.6 | 36 | 36 | 0 | 0.6 | 1.5 | 0 | 41 | 35 |
| | Hydrosilyl group/aliphatic carbon-carbon double bond (molar ratio) | | | | 1.52 | 1.84 | 2.02 | 2.02 | 0.97 | 0.97 | 1.37 | 1.75 | 0.83 | 1.57 | 1.01 | 0.83 |
| | D | | | | 0.53 | 0.53 | 0.42 | 0.47 | 0.23 | 0.23 | 0.57 | 0.74 | 0.39 | 0.76 | 0.24 | 0.15 |
| | T | | | | 0.00 | 0.00 | 0.00 | 0.00 | 0.48 | 0.48 | 0.00 | 0.00 | 0.00 | 0.00 | 0.46 | 0.47 |
| | Q | | | | 0.20 | 0.20 | 0.22 | 0.20 | 0.00 | 0.00 | 0.22 | 0.08 | 0.21 | 0.12 | 0.00 | 0.00 |

TABLE 1-continued

| | | Example 1 | Example 2 | Example 3 | Example 4 | Example 5 | Example 6 | Example 7 | Comparative Example 1 | Comparative Example 2 | Comparative Example 3 | Comparative Example 4 | Comparative Example 5 |
|---|---|---|---|---|---|---|---|---|---|---|---|---|---|
| Cured product | (T + Q)/D | 0.38 | 0.38 | 0.53 | 0.42 | 3.15 | 3.15 | 0.39 | 0.11 | 0.54 | 0.15 | 1.87 | 3.04 |
| | Measurement results | Separation strength | 0.059 | 0.069 | 0.328 | 0.285 | 0.073 | 0.105 | 0.097 | 0.085 | 0.211 | 0.108 | 0.544 | 0.932 |
| | | Total separation load | 0.002 | 0.002 | 0.011 | 0.013 | 0.012 | 0.011 | 0.012 | 0.035 | 0.044 | 0.024 | 0.051 | 0.290 |
| | Evaluation results | Garbage adhesion test | ⊙ | ⊙ | ⊙ | ⊙ | ⊙ | ⊙ | ⊙ | X | X | X | ⊙ | ○ |
| | | Adhesion test of cured product to SUS plate | Lacking tack properties | Lacking tack properties | Lacking tack properties | Lacking tack properties | Lacking tack properties | Lacking tack properties | Lacking tack properties | Lacking tack properties | Having tack properties | Lacking tack properties | Having tack properties | Having tack properties |
| | | Sulfidation resistance (light intensity maintenance ratio [%]) | 77 | 76 | 74 | 73 | 95 | 93 | 63 | 71 | 75 | 62 | 88 | 90 |

Example 8

[Evaluation of Tack Properties]

Sheets of a silicone resin (trade name "OE6630", manufactured by Dow Corning Toray Co., Ltd.) and a silicone resin (trade name "OE7660", manufactured by Dow Corning Toray Co., Ltd.) having a thickness of 3 mm were each cut out into a round shape of 15 mm in diameter to obtain test specimens for measurement. Each of the obtained test specimens for measurement was laminated with double-faced tape to the center of the smooth face of 50 mm in diameter of a test specimen fixing tool of a measurement apparatus. Then, an object was moved downward in a perpendicular direction at a slow rate and thereby contacted with the measurement sample surface. Then, the sample was compressed at a load of 100 N (0.57 MPa) and kept at a load of 100±10 N for 120 seconds. Then, the object was moved at a rate of 20 mm/min and thereby separated therefrom. The stress generated in this operation was detected and recorded on a chart using a recorder to obtain a stress curve of separation strength (stress) (N) on the ordinate and displacement (mm) on the abscissa. The largest value of the stress was obtained from the obtained stress curve. This test was conducted 10 times (N=10), and the obtained largest value of the stress is shown in Table 2.

Comparative Example 6

The test specimens for measurement used in Example 8 were evaluated for their tack properties by the probe tack test (N=10). The results are shown in Table 2. The measurement apparatus used in the probe tack test was a probe tack tester "TAC-II" (probe: made of SUS, diameter: 5 mm) manufactured by Rhesca Co., Ltd. The preload was 200 gf. The time for which the compressed state was kept was 20 seconds. The rate of separation was 120 mm/min.

TABLE 2

| | | OE6630 | | OE7660 | |
|---|---|---|---|---|---|
| | | Example 8 (N) | Comparative Example 6 (N) | Example 8 (N) | Comparative Example 6 (N) |
| Peak value | run-1 | 104.1 | 5.2 | 2.6 | 0.1 |
| | run-2 | 98.3 | 6.0 | 2.5 | 0.1 |
| | run-3 | 99.9 | 3.7 | 5.5 | 0.1 |
| | run-4 | 107.4 | 5.4 | 3.6 | 0.2 |
| | run-5 | 104.1 | 5.6 | 2.7 | 0.4 |
| | run-6 | 94.8 | 5.2 | 2.2 | 0.1 |
| | run-7 | 103.1 | 5.3 | 2.1 | 0.1 |
| | run-8 | 104.5 | 4.9 | 2.2 | 0.1 |
| | run-9 | 104.8 | 4.4 | 3.4 | 0.3 |
| | run-10 | 107.0 | 4.1 | 3.2 | 0.2 |
| Collected from all data (N = 10) | average | 102.8 | 5.0 | 3.0 | 0.2 |
| | stdev | 4.0 | 0.7 | 1.0 | 0.1 |
| | max | 107.4 | 6.0 | 5.5 | 0.4 |
| | min | 94.8 | 3.7 | 2.1 | 0.1 |
| | Variation coefficient (stdev/average × 100) | 3.9 | 14.3 | 34.1 | 66.0 |

REFERENCE SIGNS LIST

100: reflector (resin composition for light reflection)
101: metallic wire (electrode)
102: optical semiconductor device
103: bonding wire
104: cured product (sealing member)
200: maximum stress value
201: area surrounded by a stress curve from when the object and the cured product start to be separated to when the object and the cured product are completely separated and a baseline
300: test specimen for measurement
301: universal tester
302: load cell
303: object
304: double-faced adhesive tape
305: SUS plate
306: crosshead
D: upward in a perpendicular direction

The invention claimed is:

1. A curable resin composition comprising at least one polysiloxane (A) selected from the group consisting of polyorganosiloxane (A1) having not less than 2 alkenyl groups in the molecule and polyorganosiloxysilalkylene (A2) having not less than 2 alkenyl groups in the molecule, and at least one polysiloxane (B) selected from the group consisting of polyorganosiloxane (B1) having not less than 2 hydrosilyl groups in the molecule and polyorganosiloxysilalkylene (B2) having not less than 2 hydrosilyl groups in the molecule, wherein each of the polyorganosiloxysilalkylene (A2) and the polyorganosiloxysilalkylene (B2) is polysiloxane containing —Si—O—Si— and —Si—$R^4$—Si—, where $R^4$ represents an alkylene group, in the backbone, wherein the curable resin composition comprises at least one polysiloxane selected from the group consisting of polyorganosiloxane represented by the following average unit formula (a-1) and polyorganosiloxysilalkylene represented by the following average unit formula (a-2) as the polysiloxane (A), and at least one polysiloxane selected from the group consisting of polyorganosiloxane represented by the following average unit formula (b-1) and polyorganosiloxysilalkylene represented by the following average unit formula (b-2) as the polysiloxane (B), wherein the polysiloxane (A) and the polysiloxane (B) satisfy (i) the combination of the polysiloxane (A) comprising the branched polyorganosiloxane (A1) and the polysiloxane (B) comprising the polyorganosiloxane (B1), and/or (ii) the combination of the polysiloxane (A) comprising the polyorganosiloxysilalkylene (A2) having a phenyl group bonded to a silicon atom and the polysiloxane (B) comprising the polyorganosiloxysilalkylene (B2), when the ratio of the number of a silicon atom in a siloxane unit represented by ($R_3SiO_{1/2}$) to all silicon atoms contained in the curable resin composition is defined as M, the ratio of the number of a silicon atom in a siloxane unit represented by ($R_2SiO_{2/2}$) thereto is defined as D, the ratio of the number of a silicon atom in a siloxane unit represented by ($RSiO_{3/2}$) thereto is defined as T, and the ratio of the number of a silicon atom in a siloxane unit represented by ($SiO_{4/2}$) thereto is defined as Q, the curable resin composition satisfies 0.53>(T+Q)/D>0.3, M+D+T+Q=1, 1>D>0, and 0.9>Q≥0.2 (wherein R represents a monovalent group), the amount of the hydrosilyl groups is 0.9 to 5.0 mol with respect to 1 mol of aliphatic carbon-carbon double bonds present in the curable resin composition, and a cured product obtained by curing the curable resin composition by heating under at least one curing condition 25 to 180° C. and 1 to 720 minutes exhibits a separation strength of not more than 0.40 N per mm² in the following separation load evaluation and/or a total separation load of not more than 0.018 N·mm per mm² in the following separation load evaluation:

separation load evaluation: an object made of stainless steel and the cured product are contacted with each other by moving at least one of the object and the cured product from perpendicularly distant positions so as to attain a contact area of 50 to 800 mm² between the object and the cured product, pressed against each other at a load of 100 N for 2 minutes, and then separated in a perpendicular direction; change in stress on the contact face in this operation is recorded; a value determined by dividing a maximum stress value from when the object and the cured product start to be separated to when the object and the cured product are completely separated by the contact area is used as the separation strength; and a value determined by dividing an area surrounded by a stress curve from when the object and the cured product start to be separated to when the object and the cured product are completely separated and a baseline by the contact area is used as the total separation load, provided that the separation strength and the total separation load are each set to the largest value among values obtained by measurement with rates of the separation set to arbitrary 10 points (wherein adjacent 2 points differ in rate by not less than 5 mm/min) within the range of 5 to 500 mm/min,

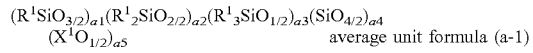
average unit formula (a-1)

wherein $R^1$ moieties are the same or different and each represent an alkyl group having 1 to 10 carbon atoms, an aryl group having 6 to 14 carbon atoms, or an alkenyl group having 2 to 8 carbon atoms, provided that a part of the $R^1$ moieties are alkenyl groups in the range of not less than 2 in the molecule; $X^1$ represents a hydrogen atom or an alkyl group having 1 to 6 carbon atoms; and a1, a2, a3, a4, and a5 represent numerical values satisfying $1>a1\geq 0$, $1>a2\geq 0$, $1>a3>0$, $1>a4>0$, $0.05>a5>0$, $a1+a2+a4>0$, and $a1+a2+a3+a4+a5=1$,

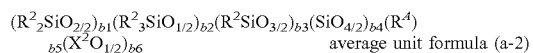
average unit formula (a-2)

wherein $R^2$ moieties are the same or different and each represent an alkyl group having 1 to 10 carbon atoms, an aryl group having 6 to 14 carbon atoms, or an alkenyl group having 2 to 8 carbon atoms, provided that a part of the $R^2$ moieties are alkenyl groups in the range of not less than 2 in the molecule; $R^A$ represents an alkylene group having 1 to 14 carbon atoms; $X^2$ represents a hydrogen atom or an alkyl group having 1 to 6 carbon atoms; and b1, b2, b3, b4, b5, and b6 represent numerical values satisfying $1>b1\geq 0$, $1>b2>0$, $1>b3\geq 0$, $1>b4\geq 0$, $0.7>b5>0$, $0.05>b6>0$, $b1+b3+b4>0$, and $b1+b2+b3+b4+b5+b6=1$,

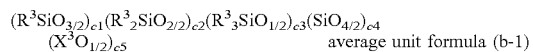
average unit formula (b-1)

wherein $R^3$ moieties are the same or different and each represent a hydrogen atom, an alkyl group having 1 to 10 carbon atoms, or an aryl group having 6 to 14 carbon atoms, provided that a part of the $R^3$ moieties are hydrogen atoms in the range of not less than 2 in the molecule; $X^3$ represents a hydrogen atom or an alkyl group having 1 to 6 carbon atoms; and c1, c2, c3, c4, and c5 represent numerical values satisfying $1>c1>0$, $1>c2>0$, $1>c3>0$, $1>c4\geq 0$, $0.05\geq c5>0$, $c1+c2+c4>0$, and $c1+c2+c3+c4+c5=1$, and

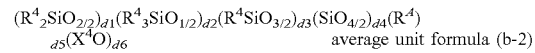
average unit formula (b-2)

wherein $R^4$ moieties are the same or different and each represent a hydrogen atom, an alkyl group having 1 to 10 carbon atoms, or an aryl group having 6 to 14 carbon atoms, provided that a part of the $R^4$ moieties are hydrogen atoms in the range of not less than 2 in the molecule; $R^A$ represents an alkylene group having 1 to 14 carbon atoms; $X^4$ represents a hydrogen atom or an alkyl group having 1 to 6 carbon atoms; and d1, d2, d3, d4, d5, and d6 represent numerical values satisfying $1>d1\geq 0$, $1>d2>0$, $1>d3>0$, $1>d4>0$, $0.5>d5>0$, $0.05>d6>0$, $d1+d3+d4>0$, and $d1+d2+d3+d4+d5+d6=1$.

2. The curable resin composition according to claim 1, further comprising ladder-type polyorganosilsesquioxane (C) having a ladder structure;

wherein the curable resin composition satisfies $0.53>(T+Q)/D>0.3$, $M+D+T+Q=1$, $1>D>0$, and $0.9>Q\geq 0.2$.

3. The curable resin composition according to claim 2, wherein the curable resin composition comprises, as the ladder-type polyorganosilsesquioxane (C), ladder-type silsesquioxane (C1) having a polyorganosilsesquioxane residue comprising a unit structure represented by the following formula (V):

[Formula 1]

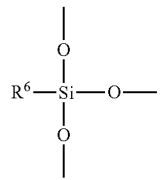
(V)

wherein $R^6$ represents a group having an aliphatic carbon-carbon double bond, and a unit structure represented by the following formula (VI):

[Formula 2]

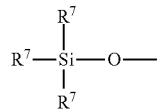
(VI)

wherein $R^7$ moieties are the same or different and each represent a hydrocarbon group at a portion or the whole of the molecular chain ends of the polyorganosilsesquioxane having a ladder structure.

4. The curable resin composition according to claim 2, wherein the curable resin composition comprises, as the ladder-type polyorganosilsesquioxane (C), ladder-type silsesquioxane (C2) having a polyorganosilsesquioxane residue comprising a unit structure represented by the following formula (VII):

[Formula 3]

-continued

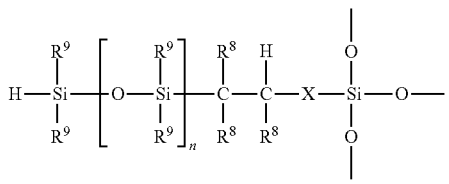
(VII)

wherein X represents a single bond, a divalent hydrocarbon group, a carbonyl group, an ether group, a thioether group, an ester group, a carbonate group, an amide group, or a group having a linkage of two or more of these groups; $R^8$ and $R^9$ moieties are the same or different and each represent a hydrogen atom, a halogen atom, a substituted or unsubstituted hydrocarbon group, an alkoxy group, an alkenyloxy group, an aryloxy group, an aralkyloxy group, an acyloxy group, an alkylthio group, an alkenylthio group, an arylthio group, an aralkylthio group, a carboxy group, an alkoxycarbonyl group, an aryloxycarbonyl group, an aralkyloxycarbonyl group, an epoxy group, a cyano group, an isocyanate group, a carbamoyl group, an isothiocyanate group, a hydroxy group, a hydroperoxy group, a sulfo group, an amino group or a substituted amino group, a mercapto group, a sulfo group, or a group represented by the following formula (s):

[Formula 4]

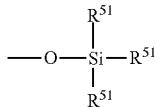
(s)

wherein $R^{51}$ moieties are the same or different and each represent a hydrogen atom, a halogen atom, a substituted or unsubstituted hydrocarbon group, an alkoxy group, an alkenyloxy group, an aryloxy group, an aralkyloxy group, an acyloxy group, an alkylthio group, an alkenylthio group, an arylthio group, an aralkylthio group, a carboxy group, an alkoxycarbonyl group, an aryloxycarbonyl group, an aralkyloxycarbonyl group, an epoxy group, a cyano group, an isocyanate group, a carbamoyl group, an isothiocyanate group, a hydroxy group, a hydroperoxy group, a sulfo group, an amino group or a substituted amino group, a mercapto group, or a sulfo group; and n represents an integer of 1 to 100, and a unit structure represented by the following formula (VIII):

[Formula 5]

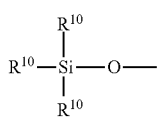
(VIII)

wherein $R^{10}$ moieties are the same or different and each represent a hydrocarbon group at a portion or the whole of the molecular chain ends of the polyorganosilsesquioxane having a ladder structure.

5. The curable resin composition according to claim 2, wherein the ladder-type polyorganosilsesquioxane (C) is ladder-type polyorganosilsesquioxane having a substituted or unsubstituted aryl group at a portion or the whole of side chains.

6. The curable resin composition according to claim 1, wherein R comprises a monovalent substituted or unsubstituted hydrocarbon group, and
the ratio of an aryl group to the total amount of the monovalent substituted or unsubstituted hydrocarbon groups bonded to silicon atom in all polysiloxanes contained in the curable resin composition is not less than 10% by mol.

7. The curable resin composition according to claim 1, further comprising an isocyanuric skeleton-containing compound (D).

8. The curable resin composition according to claim 7, wherein the isocyanuric skeleton-containing compound (D) is a compound represented by the following formula (1):

[Formula 6]

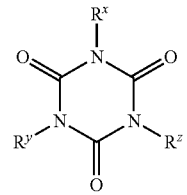
(1)

wherein $R^x$, $R^y$, and $R^z$ are the same or different and each represent a group represented by the formula (1a) or a group represented by the formula (1b):

[Formula 7]

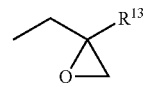
(1a)

wherein $R^{13}$ represents a hydrogen atom or a linear or branched alkyl group having 1 to 8 carbon atoms, and

[Formula 8]

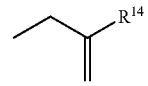
(1b)

wherein $R^{14}$ represents a hydrogen atom or a linear or branched alkyl group having 1 to 8 carbon atoms.

9. The curable resin composition according to claim 8, wherein not less than any one of $R^x$, $R^y$, and $R^z$ in the formula (1) is a group represented by the formula (1b).

10. The curable resin composition according to claim 1, further comprising a silane coupling agent (E).

11. A cured product of a curable resin composition according to claim 1.

12. A sealing agent comprising a curable resin composition according to claim 1.

13. A semiconductor apparatus having a semiconductor device and a sealing member which seals the semiconductor device, wherein
the sealing member is a cured product of a sealing agent according to claim 12.

14. A curable resin composition comprising
at least one polysiloxane (A) selected from the group consisting of polyorganosiloxane (A1) having not less than 2 alkenyl groups in the molecule and polyorganosiloxysilalkylene (A2) having not less than 2 alkenyl groups in the molecule,
at least one polysiloxane (B) selected from the group consisting of polyorganosiloxane (B1) having not less than 2 hydrosilyl groups in the molecule and polyorganosiloxysilalkylene (B2) having not less than 2 hydrosilyl groups in the molecule, and
ladder-type polyorganosilsesquioxane (C) having a ladder structure, wherein each of the polyorganosiloxysilalkylene (A2) and the polyorganosiloxysilalkylene (B2) is polysiloxane containing —Si—O—Si— and —Si—$R^A$—Si—, where $R^A$ represents an alkylene group, in the backbone,
wherein
the curable resin composition comprises
at least one polysiloxane selected from the group consisting of polyorganosiloxane represented by the following average unit formula (a-1) and polyorganosiloxysilalkylene represented by the following average unit formula (a-2) as the polysiloxane (A), and
at least one polysiloxane selected from the group consisting of polyorganosiloxane represented by the following average unit formula (b-1) and polyorganosiloxysilalkylene represented by the following average unit formula (b-2) as the polysiloxane (B),
wherein the polysiloxane (A) and the polysiloxane (B) satisfy (i) the combination of the polysiloxane (A) comprising the branched polyorganosiloxane (A1) and the polysiloxane (B) comprising the polyorganosiloxane (B1), and/or (ii) the combination of the polysiloxane (A) comprising the polyorganosiloxysilalkylene (A2) having a phenyl group bonded to a silicon atom and the polysiloxane (B) comprising the polyorganosiloxysilalkylene (B2),
when the ratio of the number of a silicon atom in a siloxane unit represented by $(R_3SiO_{1/2})$ to all silicon atoms contained in the curable resin composition is defined as M, the ratio of the number of a silicon atom in a siloxane unit represented by $(R_2SiO_{2/2})$ thereto is defined as D, the ratio of the number of a silicon atom in a siloxane unit represented by $(RSiO_{3/2})$ thereto is defined as T, and the ratio of the number of a silicon atom in a siloxane unit represented by $(SiO_{4/2})$ thereto is defined as Q, the curable resin composition satisfies $0.53 \geq (T+Q)/D > 0.3$, $M+D+T+Q=1$, and $0.9 > Q \geq 0.2$ (wherein R represents a monovalent group),
the amount of the hydrosilyl groups is 0.9 to 5.0 mol with respect to 1 mol of aliphatic carbon-carbon double bonds present in the curable resin composition, and
a cured product obtained by curing the curable resin composition by heating under at least one curing condition 25 to 180° C. and 1 to 720 minutes exhibits a separation strength of not more than 0.40 N per mm$^2$ in the following separation load evaluation and/or a total separation load of not more than 0.018 N·mm per mm$^2$ in the following separation load evaluation:

separation load evaluation: an object made of stainless steel and the cured product are contacted with each other by moving at least one of the object and the cured product from perpendicularly distant positions so as to attain a contact area of 50 to 800 mm$^2$ between the object and the cured product, pressed against each other at a load of 100 N for 2 minutes, and then separated in a perpendicular direction; change in stress on the contact face in this operation is recorded; a value determined by dividing a maximum stress value from when the object and the cured product start to be separated to when the object and the cured product are completely separated by the contact area is used as the separation strength; and a value determined by dividing an area surrounded by a stress curve from when the object and the cured product start to be separated to when the object and the cured product are completely separated and a baseline by the contact area is used as the total separation load, provided that the separation strength and the total separation load are each set to the largest value among values obtained by measurement with rates of the separation set to arbitrary 10 points (wherein adjacent 2 points differ in rate by not less than 5 mm/min) within the range of 5 to 500 mm/min,

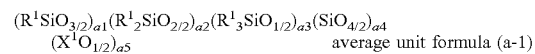
average unit formula (a-1)

wherein $R^1$ moieties are the same or different and each represent an alkyl group having 1 to 10 carbon atoms, an aryl group having 6 to 14 carbon atoms, or an alkenyl group having 2 to 8 carbon atoms, provided that a part of the $R^1$ moieties are alkenyl groups in the range of not less than 2 in the molecule; $X^1$ represents a hydrogen atom or an alkyl group having 1 to 6 carbon atoms; and a1, a2, a3, a4, and a5 represent numerical values satisfying $1 > a1 \geq 0$, $1 > a2 \geq 0$, $1 > a3 > 0$, $1 > a4 > 0$, $0.05 > a5 > 0$, $a1+a2+a4 > 0$, and $a1+a2+a3+a4+a5=1$,

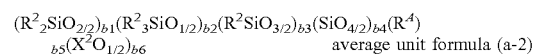
average unit formula (a-2)

wherein $R^2$ moieties are the same or different and each represent an alkyl group having 1 to 10 carbon atoms, an aryl group having 6 to 14 carbon atoms, or an alkenyl group having 2 to 8 carbon atoms, provided that a part of the $R^2$ moieties are alkenyl groups in the range of not less than 2 in the molecule; $R^A$ represents an alkylene group having 1 to 14 carbon atoms; $X^2$ represents a hydrogen atom or an alkyl group having 1 to 6 carbon atoms; and b1, b2, b3, b4, b5, and b6 represent numerical values satisfying $1 > b1 \geq 0$, $1 > b2 > 0$, $1 > b3 \geq 0$, $1 > b4 \geq 0$, $0.7 > b5 > 0$, $0.05 > b6 > 0$, $b1+b3+b4 > 0$, and $b1+b2+b3+b4+b5+b6=1$,

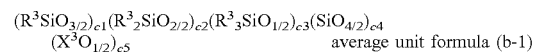
average unit formula (b-1)

wherein $R^3$ moieties are the same or different and each represent a hydrogen atom, an alkyl group having 1 to 10 carbon atoms, or an aryl group having 6 to 14 carbon atoms, provided that a part of the $R^3$ moieties are hydrogen atoms in the range of not less than 2 in the molecule; $X^3$ represents a hydrogen atom or an alkyl group having 1 to 6 carbon atoms; and c1, c2, c3, c4, and c5 represent numerical values satisfying $1 > c1 > 0$, $1 > c2 > 0$, $1 > c3 > 0$, $1 > c4 \geq 0$, $0.05 \geq c5 > 0$, $c1+c2+c4 > 0$, and $c1+c2+c3+c4+c5=1$, and

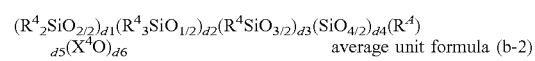
average unit formula (b-2)

wherein $R^4$ moieties are the same or different and each represent a hydrogen atom, an alkyl group having 1 to 10 carbon atoms, or an aryl group having 6 to 14 carbon atoms, provided that a part of the $R^4$ moieties are hydrogen atoms in the range of not less than 2 in the molecule; $R^4$ represents an alkylene group having 1 to 14 carbon atoms; $X^4$ represents a hydrogen atom or an alkyl group having 1 to 6 carbon atoms; and d1, d2, d3, d4, d5, and d6 represent numerical values satisfying 1>d1>0, 1>d2>0, 1>d3>0, 1>d4>0, 0.5>d5>0, 0.05≥d6≥0, d1+d3+d4>0, and d1+d2+d3+d4+d5+d6=1.

15. The curable resin composition according to claim 14, wherein the curable resin composition comprises, as the ladder-type polyorganosilsesquioxane (C), ladder-type silsesquioxane (C1) having a polyorganosilsesquioxane residue comprising a unit structure represented by the following formula (V):

[Formula 1]

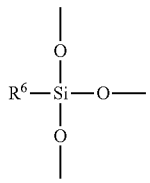
(V)

wherein $R^6$ represents a group having an aliphatic carbon-carbon double bond, and a unit structure represented by the following formula (VI):

[Formula 2]

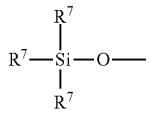
(VI)

wherein $R^7$ moieties are the same or different and each represent a hydrocarbon group at a portion or the whole of the molecular chain ends of the polyorganosilsesquioxane having a ladder structure.

16. The curable resin composition according to claim 14, wherein the curable resin composition comprises, as the ladder-type polyorganosilsesquioxane (C), ladder-type silsesquioxane (C2) having a polyorganosilsesquioxane residue comprising a unit structure represented by the following formula (VII):

[Formula 3]

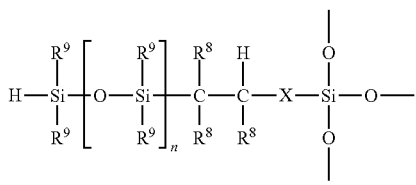
(VII)

wherein X represents a single bond, a divalent hydrocarbon group, a carbonyl group, an ether group, a thioether group, an ester group, a carbonate group, an amide group, or a group having a linkage of two or more of these groups; $R_8$ and $R_9$ moieties are the same or different and each represent a hydrogen atom, a halogen atom, a substituted or unsubstituted hydrocarbon group, an alkoxy group, an alkenyloxy group, an aryloxy group, an aralkyloxy group, an acyloxy group, an alkylthio group, an alkenylthio group, an arylthio group, an aralkylthio group, a carboxy group, an alkoxycarbonyl group, an aryloxycarbonyl group, an aralkyloxycarbonyl group, an epoxy group, a cyano group, an isocyanate group, a carbamoyl group, an isothiocyanate group, a hydroxy group, a hydroperoxy group, a sulfo group, an amino group or a substituted amino group, a mercapto group, a sulfo group, or a group represented by the following formula(s):

[Formula 4]

(s)

wherein $R^{51}$ moieties are the same or different and each represent a hydrogen atom, a halogen atom, a substituted or unsubstituted hydrocarbon group, an alkoxy group, an alkenyloxy group, an aryloxy group, an aralkyloxy group, an acyloxy group, an alkylthio group, an alkenylthio group, an arylthio group, an aralkylthio group, a carboxy group, an alkoxycarbonyl group, an aryloxycarbonyl group, an aralkyloxycarbonyl group, an epoxy group, a cyano group, an isocyanate group, a carbamoyl group, an isothiocyanate group, a hydroxy group, a hydroperoxy group, a sulfo group, an amino group or a substituted amino group, a mercapto group, or a sulfo group; and n represents an integer of 1 to 100, and a unit structure represented by the following formula (VIII):

[Formula 5]

(VIII)

wherein $R^{10}$ moieties are the same or different and each represent a hydrocarbon group at a portion or the whole of the molecular chain ends of the polyorganosilsesquioxane having a ladder structure.

17. The curable resin composition according to claim 14, wherein the ladder-type polyorganosilsesquioxane (C) is ladder-type polyorganosilsesquioxane having a substituted or unsubstituted aryl group at a portion or the whole of side chains.

18. The curable resin composition according to claim 14, wherein R comprises a monovalent substituted or unsubstituted hydrocarbon group, and the ratio of an aryl group to the total amount of the monovalent substituted or unsubstituted hydrocarbon groups bonded to silicon atom in all polysiloxanes contained in the curable resin composition is not less than 10% by mol.

19. The curable resin composition according to claim 14, further comprising
an isocyanuric skeleton-containing compound (D).

20. The curable resin composition according to claim 19, wherein the isocyanuric skeleton-containing compound (D) is a compound represented by the following formula (1):

[Formula 6]

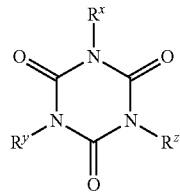

(1)

wherein $R^x$, $R^y$, and $R^z$ are the same or different and each represent a group represented by the formula (1a) or a group represented by the formula (1b):

[Formula 7]

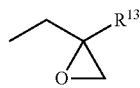

(1a)

wherein $R^{13}$ represents a hydrogen atom or a linear or branched alkyl group having 1 to 8 carbon atoms, and

[Formula 8]

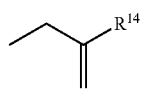

(1b)

wherein $R^{14}$ represents a hydrogen atom or a linear or branched alkyl group having 1 to 8 carbon atoms.

* * * * *